United States Patent
Singer et al.

(10) Patent No.: US 10,730,041 B2
(45) Date of Patent: Aug. 4, 2020

(54) INTEGRATED FLUIDIC DEVICES AND RELATED METHODS

(71) Applicant: HelixBind, Inc., Marlborough, MA (US)

(72) Inventors: Alon Singer, Concord, MA (US); Ranjit Prakash, Northborough, MA (US)

(73) Assignee: HelixBind, Inc., Marlborough, MA (US)

( * ) Notice: Subject to any disclaimer, the term of this patent is extended or adjusted under 35 U.S.C. 154(b) by 0 days.

(21) Appl. No.: 15/458,288

(22) Filed: Mar. 14, 2017

(65) Prior Publication Data

US 2017/0259257 A1 Sep. 14, 2017

Related U.S. Application Data

(60) Provisional application No. 62/308,031, filed on Mar. 14, 2016.

(51) Int. Cl.
*B01L 3/00* (2006.01)
*B01D 71/34* (2006.01)
(Continued)

(52) U.S. Cl.
CPC ............... *B01L 3/502* (2013.01); *B01D 71/34* (2013.01); *B01L 3/5027* (2013.01); *C12Q 1/686* (2013.01);
(Continued)

(58) Field of Classification Search
CPC .................. B01L 3/502; B01L 3/5027; B01L 2300/0867; B01L 2200/0684;
(Continued)

(56) References Cited

U.S. PATENT DOCUMENTS

| 5,786,528 A | 7/1998 | Dileo et al. |
| 6,664,045 B1 | 12/2003 | Hyldig-Nielsen et al. |

(Continued)

FOREIGN PATENT DOCUMENTS

| EP | 2 333 105 A1 | 6/2011 |
| WO | WO 2006/117557 A2 | 11/2006 |

(Continued)

OTHER PUBLICATIONS

International Search Report and Written Opinion for PCT/US2017/022280 dated Aug. 29, 2017.
(Continued)

*Primary Examiner* — Lore R Jarrett
(74) *Attorney, Agent, or Firm* — Wolf, Greenfield & Sacks, P.C.

(57) ABSTRACT

Fluidic devices and related methods are generally provided. The fluidic devices described herein may be useful, for example, for diagnostic purposes (e.g., detection of the presence of one or more disease causing bacteria in a patient sample). Unlike certain existing fluidic devices for diagnostic purposes, the fluidic devices and methods described herein may be useful for detecting the presence of numerous disease causing bacteria in a patient sample substantially simultaneously (e.g., in parallel). In some embodiments, the fluidic devices and methods described herein provide highly sensitive detection of microbes in relatively large fluidic samples (e.g., between 0.5 mL and about 5 mL), as compared to certain existing fluidic detection (e.g., microfluidic) devices and methods. In an exemplary embodiment, increased detection sensitivity of microbial pathogens present in a patient sample (e.g., blood) is performed by selectively removing human nucleic acid prior to sensitive detection of microbial infection. In some embodiments, the fluidic device allows for the identification of microbial pathogens
(Continued)

directly from unprocessed blood without having to conduct blood culturing processes.

35 Claims, 15 Drawing Sheets

Specification includes a Sequence Listing.

(51) Int. Cl.

| | | |
|---|---|---|
| *C12Q 1/686* | (2018.01) | |
| *B01L 7/00* | (2006.01) | |
| *B01D 63/08* | (2006.01) | |
| *B01D 69/02* | (2006.01) | |

(52) U.S. Cl.
CPC ............ *B01D 63/088* (2013.01); *B01D 69/02* (2013.01); *B01D 2325/20* (2013.01); *B01D 2325/38* (2013.01); *B01L 7/52* (2013.01); *B01L 2200/0673* (2013.01); *B01L 2200/0684* (2013.01); *B01L 2200/0689* (2013.01); *B01L 2200/16* (2013.01); *B01L 2300/0681* (2013.01); *B01L 2300/087* (2013.01); *B01L 2300/0816* (2013.01); *B01L 2300/0867* (2013.01); *B01L 2300/166* (2013.01); *B01L 2300/1827* (2013.01); *B01L 2400/049* (2013.01); *B01L 2400/0487* (2013.01); *B01L 2400/06* (2013.01)

(58) Field of Classification Search
CPC .............. B01L 2200/0673; B01L 7/52; B01L 2400/06; B01L 2200/16; B01L 2200/0689; B01L 2400/0487; B01L 2325/20; B01L 2300/1827; B01L 2300/0681; B01L 2300/087; B01L 2300/166; B01L 2400/049; B01D 71/34; B01D 69/02; B01D 63/088; B01D 2325/38; B01D 2325/20; C12Q 1/686
See application file for complete search history.

(56) References Cited

U.S. PATENT DOCUMENTS

| | | | |
|---|---|---|---|
| 7,893,251 B2 | 2/2011 | Lorenz | |
| 8,304,185 B2 | 11/2012 | Stone | |
| 9,663,830 B2 | 5/2017 | Singer | |
| 2005/0142570 A1 | 6/2005 | Parthasarathy et al. | |
| 2006/0205085 A1 | 9/2006 | Handique et al. | |
| 2007/0184547 A1* | 8/2007 | Handique ................ G01N 1/34 | |
| | | | 435/288.5 |
| 2007/0292941 A1* | 12/2007 | Handique ........... F16K 99/0001 | |
| | | | 435/288.7 |
| 2009/0081675 A1 | 3/2009 | Colston et al. | |
| 2009/0130766 A1* | 5/2009 | Weekamp ............ B01L 3/50273 | |
| | | | 436/63 |
| 2010/0021910 A1 | 1/2010 | Cao et al. | |
| 2011/0136179 A1 | 6/2011 | Bin/Lee et al. | |
| 2012/0142026 A1* | 6/2012 | Miller .................... B01L 3/502 | |
| | | | 435/7.9 |
| 2012/0276530 A1 | 11/2012 | Meller et al. | |
| 2013/0137172 A1* | 5/2013 | Ririe ................. B01L 3/502738 | |
| | | | 435/306.1 |
| 2013/0203610 A1 | 8/2013 | Meller et al. | |
| 2013/0256118 A1 | 10/2013 | Meller et al. | |
| 2013/0302787 A1* | 11/2013 | Agarwal ................... B01L 3/52 | |
| | | | 435/5 |
| 2013/0302791 A1* | 11/2013 | Cramer .............. C12N 15/1013 | |
| | | | 435/6.1 |
| 2013/0302809 A1* | 11/2013 | Bru Gibed ........... B01L 3/5027 | |
| | | | 435/6.12 |
| 2014/0206562 A1* | 7/2014 | McCormack ...... G01N 33/5302 | |
| | | | 506/9 |
| 2014/0283945 A1* | 9/2014 | Jones ...................... B01L 3/502 | |
| | | | 141/1 |
| 2014/0328733 A1 | 11/2014 | Prakash | |
| 2015/0099657 A1 | 4/2015 | Singer | |
| 2015/0259672 A1 | 9/2015 | Selden et al. | |
| 2017/0218434 A1 | 8/2017 | Singer | |
| 2017/0292146 A1 | 10/2017 | Singer et al. | |

FOREIGN PATENT DOCUMENTS

| | | |
|---|---|---|
| WO | WO 2010/132823 A2 | 11/2010 |
| WO | WO 2011/028494 A2 | 3/2011 |
| WO | WO 2011/070507 A1 | 6/2011 |
| WO | WO 2011/087789 A2 | 7/2011 |
| WO | WO 2013/176992 A1 | 11/2013 |
| WO | WO 2016/044621 A2 | 3/2016 |

OTHER PUBLICATIONS

Invitation to Pay Additional Fees for PCT/US2017/022280 dated Jun. 9, 2017.
[No Author Listed], Microfiltration Membranes—Microfiltration Membranes for Filtration and Venting Applications. Millipore Coporation. Billerica, MA. 2012. 8 pages.
He et al., Strand Invasion of Extended, Mixed-Sequence B-DNA by γPNAs. J. Am. Chem. Soc. 2009;131(34):12088-90.
Egholm et al., Efficient pH-independent sequence-specific DNA binding by pseudoisocytosine-containing bis-PNA. Nucleic Acids Res. Jan. 1995;23(2):217-22.
Rane et al., Droplet microfluidics for amplification-free genetic detection of single cells. Lab Chip. 2012;12:3341-7. Epub Jul. 4, 2012.
Xi et al., Use of molecular beacons for the detection of bacteria in microfluidic devices. Proc. SPIE 4982, Microfluidics, BioMEMS, and Medical Microsystems. Jan. 17, 2003:170-7.
Extended European Search Report for App. No. EP 17767322.5 dated Nov. 26, 2019.
EP 17767322.5, dated Nov. 26, 2019, Extended European Search Report.

\* cited by examiner

Side View

Top View

SEQUENCE LISTING

```
<160> NUMBER OF SEQ ID NOS: 45

<210> SEQ ID NO 1
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 1
tcgaagagca ggcaa                                                     15

<210> SEQ ID NO 2
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 2
tcgaggttta ccaatg                                                    16

<210> SEQ ID NO 3
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 3
gaggtattta ccaatg                                                    16

<210> SEQ ID NO 4
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 4
aagtcaatga ttgcagg                                                   17

<210> SEQ ID NO 5
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 5
ttgtcaatga gagtagg                                                          17

<210> SEQ ID NO 6
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 6
tacacaatta atgagaa                                                          17

<210> SEQ ID NO 7
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 7
gcaatcagag agaata                                                           16

<210> SEQ ID NO 8
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 8
aattcgttta cagtacg                                                          17

<210> SEQ ID NO 9
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 9
tcggatgata ccaatt                                                           16

<210> SEQ ID NO 10
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 10
acggtcatag tctacgg                                                          17

<210> SEQ ID NO 11
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 11
cgcggtgatt ctagagt                                                          17

<210> SEQ ID NO 12

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 12
cgcggtgata ctagagt                                                    17

<210> SEQ ID NO 13
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 13
aattcaagtg gtggaa                                                     16

<210> SEQ ID NO 14
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 14
aattcgagtg gtggaa                                                     16

<210> SEQ ID NO 15
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 15
ggtgatagag atccat                                                     16

<210> SEQ ID NO 16
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 16
ctcgttcgag agacac                                                     16

<210> SEQ ID NO 17
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 17
gtatttaccg atggg                                                      15

<210> SEQ ID NO 18
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 18
```
acgtaaggtc atgtgc                                               16

<210> SEQ ID NO 19
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 19
gatctaaaag gtgcc                                                15

<210> SEQ ID NO 20
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 20
tcaggcttct gtaac                                                15

<210> SEQ ID NO 21
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 21
agcggttttc cgatc                                                15

<210> SEQ ID NO 22
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 22
tgcgtagttt tttcta                                               16

<210> SEQ ID NO 23
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 23
cctgatggtc ccatagat                                             18

<210> SEQ ID NO 24
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 24
caggatcttt ggttgt                                               16

<210> SEQ ID NO 25
<211> LENGTH: 16
<212> TYPE: DNA

```
<213> ORGANISM: Artificial Sequence
<220> FEATURE:
<223> OTHER INFORMATION: Synthetic Polynucleotide

<400> SEQUENCE: 25
gcattgatag gagatc                                                     16

<210> SEQ ID NO 26
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 26
ccagggtaat tgagac                                                     16

<210> SEQ ID NO 27
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 27
cagtgttagc aactgc                                                     16

<210> SEQ ID NO 28
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 28
gtcctatcca tttgcat                                                    17

<210> SEQ ID NO 29
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 29
ctactcggac ttgcgc                                                     16

<210> SEQ ID NO 30
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 30
aaacgacagt ataacag                                                    17

<210> SEQ ID NO 31
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 31
tcgcaattca agaagg                                                     16
```

<210> SEQ ID NO 32
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 32
ttgtcccatc cattcg                                                     16

<210> SEQ ID NO 33
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 33
ggtttcctgc ttggac                                                     16

<210> SEQ ID NO 34
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 34
tggctggagt gtcgg                                                      15

<210> SEQ ID NO 35
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 35
ctgaaccaca agtagga                                                    17

<210> SEQ ID NO 36
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 36
accaagctgt tgcgtaac                                                   18

<210> SEQ ID NO 37
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 37
agtacggaca acagtct                                                    17

<210> SEQ ID NO 38
<211> LENGTH: 34
<212> TYPE: DNA
<213> ORGANISM: Artificial Sequence
<220> FEATURE:

<223> OTHER INFORMATION: Synthetic Polynucleotide

<400> SEQUENCE: 38
cccccccctc agttatcgtt tatttgatag tacc                                  34

<210> SEQ ID NO 39
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 39
cccccccctc agttatcgtt tatttgatag ttcc                                  34

<210> SEQ ID NO 40
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 40
cccttcccag agtttgatca tggctcag                                         28

<210> SEQ ID NO 41
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 41
cccttccaga gtttgatcct ggctcag                                          27

<210> SEQ ID NO 42
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 42 cccccggtt accttgttac gactt                                             25

<210> SEQ ID NO 43
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 43
cccccggcta ccttgttacg actt                                             24

<210> SEQ ID NO 44
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 44
cccttccctg atgactcgtg cctacta                                          27

```
<210> SEQ ID NO 45
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 45
ccctctccct gatgacttgc gcttacta                                    28
```

INTEGRATED FLUIDIC DEVICES AND RELATED METHODS

RELATED APPLICATIONS

The present application claims priority under 35 U.S.C. § 119(e) to U.S. Provisional Patent Application No. 62/308,031, filed Mar. 14, 2016, and entitled "FLUIDIC DEVICES AND RELATED METHODS," which is incorporated herein by reference in its entirety.

GOVERNMENT SPONSERSHIP

This invention was made with Government support under Contract Nos. AI109913 and AI124726 awarded by the U.S. National Institutes of Health. The Government has certain rights in this invention.

TECHNICAL FIELD

The present invention generally relates to fluidic devices and related methods.

BACKGROUND

Bloodstream infections (BSIs) have risen to become the 6th leading cause of death in the U.S. and the most expensive hospital-treated condition, at over $30B annually. BSIs account for 25% of all ICU usage and roughly 50% of all hospital deaths in the U.S. BSIs are typically caused by bacteria or fungi, and effective disease management requires their early and accurate identification. BSIs are typically identified through a series of blood-cultures that take up to several days to identify potential pathogens. Blood-cultures are widely considered the barrier to a hypothesis driven first-line antimicrobial intervention.

Modern molecular approaches have the potential to revolutionize this field, however limitations including lack of sensitivity, inaccurate performance, narrow coverage, and insufficient diagnostic detail have prevented these methods from making an impact. Indeed, in contrast to numerous infectious diseases, a clear capability gap remains despite the immense clinical need. It is the combined difficulty of immensely low pathogen loads (1-100 CFU/ml), the requirement for broad coverage with high levels of detail (20 pathogens are responsible for roughly 90% of cases where species level information is clinically required), a difficult specimen matrix (blood), and the need for a rapid turnaround; all of which when combined, have proven difficult to overcome.

Molecular diagnostic methods for identifying microbial pathogens can be performed by probing for conserved regions in their respective genomic material. Methods for genomic identification include isolation and detection of pathogenic DNA. It is further advantageous to develop an automated manner in which to conduct molecular processes.

Automated molecular processes have the advantage of being less likely to be compromised due to human error, contaminations, and are potentially faster. Furthermore, they hold the potential to provide more repeatable results; a highly sought after trait.

SUMMARY

The present invention generally relates to fluidic devices and related methods.

In one aspect, fluidic devices are provided. In some embodiments, the fluidic device comprises a sample inlet, a fluidic channel in fluidic communication with the sample inlet, wherein the fluidic channel has a length of at least 1 cm and a channel length-to-width ratio of at least 5:1, a first lysis region in fluidic communication with the fluidic channel, a first isolation region in fluidic communication with first lysis region, a second lysis region in fluidic communication with the first isolation region, a second isolation region in fluidic communication with the second lysis region, at least one reaction region in fluidic communication with the second isolation region, an amplification region in fluidic communication with at least one of the reaction regions, and a plurality of processing chambers, each in fluidic communication with at least one of the reaction regions and/or the amplification region.

In some embodiments, the fluidic device comprises a plurality of fluidic reservoirs, wherein each fluidic reservoir has a volume of at least 0.1 mL, a plurality of gas chambers, wherein each gas chamber is in fluidic communication with a fluidic reservoir, and wherein each gas chamber has a volume of at least 0.1 mL, and a plurality of fluidic channels, wherein each fluidic channel is in fluidic communication with one or more fluidic reservoirs and/or one or more gas chambers, and wherein each fluidic channel has a volume of less than 1000 µL, wherein a longitudinal axis of at least one fluidic reservoir is substantially perpendicular to a longitudinal axis of at least one fluidic channel having a length of at least 1 cm.

In some embodiments, the fluidic device comprises a fluidic hub comprising a hub channel having a length of at least 1 cm and a channel length-to-width ratio of at least 5:1, at least 10 branching channels branching from the fluidic hub, a plurality of valves, each valve positioned between the branching channels and the fluidic hub, and a plurality of fluidic reservoirs, each fluidic reservoir connected to a branching channel.

In some embodiments, the fluidic device comprises a fluidic hub comprising a hub channel having a length of at least 1 cm and a channel length-to-width ratio of at least 5:1, a first branching channel branching from the fluidic hub, a first fluidic reservoir in fluidic communication with the first branching channel, a first gas chamber in fluidic communication with the first fluidic reservoir, a second branching channel branching from the fluidic hub, a second fluidic reservoir in fluidic communication with the second branching channel, and a second gas chamber in fluidic communication with the second fluidic reservoir.

In some embodiments, the fluidic device comprises a first fluidic reservoir, a first channel in fluidic communication with the first fluidic reservoir, a first valve associated with the first channel, a second fluidic reservoir, a second channel in fluidic communication with the second fluidic reservoir, a second valve associated with the second channel, and a connecting channel positioned between the first fluidic reservoir and the second fluidic reservoir, wherein at least a portion of the connecting channel has a smaller cross-sectional area than a cross-sectional area of the first fluidic reservoir and a cross-sectional dimension of the second fluidic reservoir, and the connecting channel has a length of greater than or equal to 250 microns and less than or equal to 10 cm.

In some embodiments, the fluidic device comprises a channel, a fluidic reservoir connected to the channel, an outlet channel in fluidic communication with the fluidic reservoir, a valve associated with the outlet channel, and a cover adjacent to the fluidic reservoir, wherein the cover encloses the fluidic reservoir, wherein the cover is a semipermeable membrane, and wherein the semipermeable membrane is hydrophobic, has an air permeability of greater than or equal to 0.4 slpm at 1 psi and less than or equal to 5 slpm at 1 psi.

In another aspect, methods of transporting a fluid (e.g., in a fluidic device) are provided. In some embodiments, the method comprises, in a fluidic device comprising a fluidic reservoir, a gas chamber in fluidic communication with the fluidic reservoir, and a fluidic channel in fluidic communication with the fluidic reservoir, wherein a longitudinal axis of the fluidic reservoir is substantially perpendicular to a longitudinal axis of the fluidic channel, performing the steps of introducing a first fluid in the fluidic reservoir, wherein the first fluid is a liquid, introducing a second fluid in the gas chamber, wherein the second fluid is a gas, and applying a pressure to the second fluid such that the second fluid flows from the gas chamber to the fluidic reservoir and pushes the first fluid from the fluidic column into the fluidic channel.

In some embodiments, the method comprises, in a fluidic device comprising a fluidic hub comprising a hub channel having a length of at least 1 cm and a channel length-to-width ratio of at least 5:1, a first branching channel branching from the fluidic hub, and a second branching channel branching from the fluidic hub, performing the steps of introducing a first fluid in the first branching channel, wherein the first fluid is a liquid, introducing a second fluid in the first branching channel, wherein the second fluid is a gas, while the first branching channel is in in fluidic communication with the fluidic hub and the second branching channel is not in fluidic communication with the fluidic hub, applying a pressure to the second fluid such that the second fluid pushes the first fluid from the first branching channel into the fluidic hub, and introducing the second fluid into the fluidic hub.

In some embodiments, the method comprises, in a fluidic device comprising a fluidic hub comprising a hub channel having a length of at least 1 cm and a channel length-to-width ratio of at least 5:1, a first branching channel branching from the fluidic hub, a first fluidic reservoir connected to the first branching channel, a second branching channel branching from the fluidic hub, a second fluidic reservoir connected to the second branching channel, a third branching channel branching from the fluidic hub, and a third fluidic reservoir connected to the second branching channel, performing the steps of flowing a first fluid having a volume of at least 0.1 mL from the first fluidic reservoir to the fluidic hub via the first branching channel, flowing the first fluid from the fluidic hub to the second fluidic reservoir via the second branching channel, wherein the second fluidic reservoir contains a reagent, reacting the first fluid with the reagent to form a reacted fluid, flowing the reacted fluid from the second fluidic reservoir into the fluidic hub, and flowing the reacted fluid from the fluidic hub to a third fluidic reservoir via the third branching channel.

In some embodiments, the method comprises, in a fluidic device comprising a fluidic hub comprising a hub channel having a length of at least 1 cm and a channel length-to-width ratio of at least 5:1, a first branching channel branching from the fluidic hub, a first fluidic reservoir connected to the first branching channel, a first gas chamber in fluidic communication with the first fluidic reservoir, and a second branching channel branching from the fluidic hub, performing the steps of flowing a first fluid having a volume of at least 0.1 mL from the fluidic hub to the first fluidic reservoir via the first branching channel, reacting the first fluid with a reagent to form a reacted fluid in the first fluidic reservoir, and applying a pressure to the first gas chamber such that the reacted fluid flows into the fluidic hub and into the second branching channel.

In some embodiments, the method comprises, in a fluidic device comprising a fluidic reservoir containing a gas, an outlet channel in fluidic communication with the fluidic reservoir, a valve associated with the outlet channel, and a cover adjacent to the fluidic reservoir, wherein the cover encloses the fluidic reservoir, and wherein the cover is a semipermeable membrane, performing the steps of closing the valve, introducing a first fluid into the fluidic reservoir, wherein the first fluid is a liquid, causing the gas contained in the fluidic reservoir to pass across the semipermeable membrane, and substantially preventing the first fluid from passing across the semipermeable membrane.

In yet another aspect, methods of mixing a fluid in a fluidic device are provided. In some embodiments, the method comprises, in a fluidic device comprising a first fluidic reservoir, a second fluidic reservoir, and a connecting channel positioned between the first fluidic reservoir and the second fluidic reservoir, wherein at least a portion of the connecting channel has a smaller cross-sectional area than a cross-sectional area of the first fluidic reservoir and a cross-sectional dimension of the second fluidic reservoir, performing the steps of flowing, in a first direction, a first fluid from the first fluidic reservoir to the second fluidic reservoir via the connecting channel, wherein the first fluid is a liquid, flowing, in a second direction, the first fluid from the second fluidic reservoir to the first fluidic reservoir via the connecting channel, wherein the second direction is different from the first direction, and causing mixing within the first fluid.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
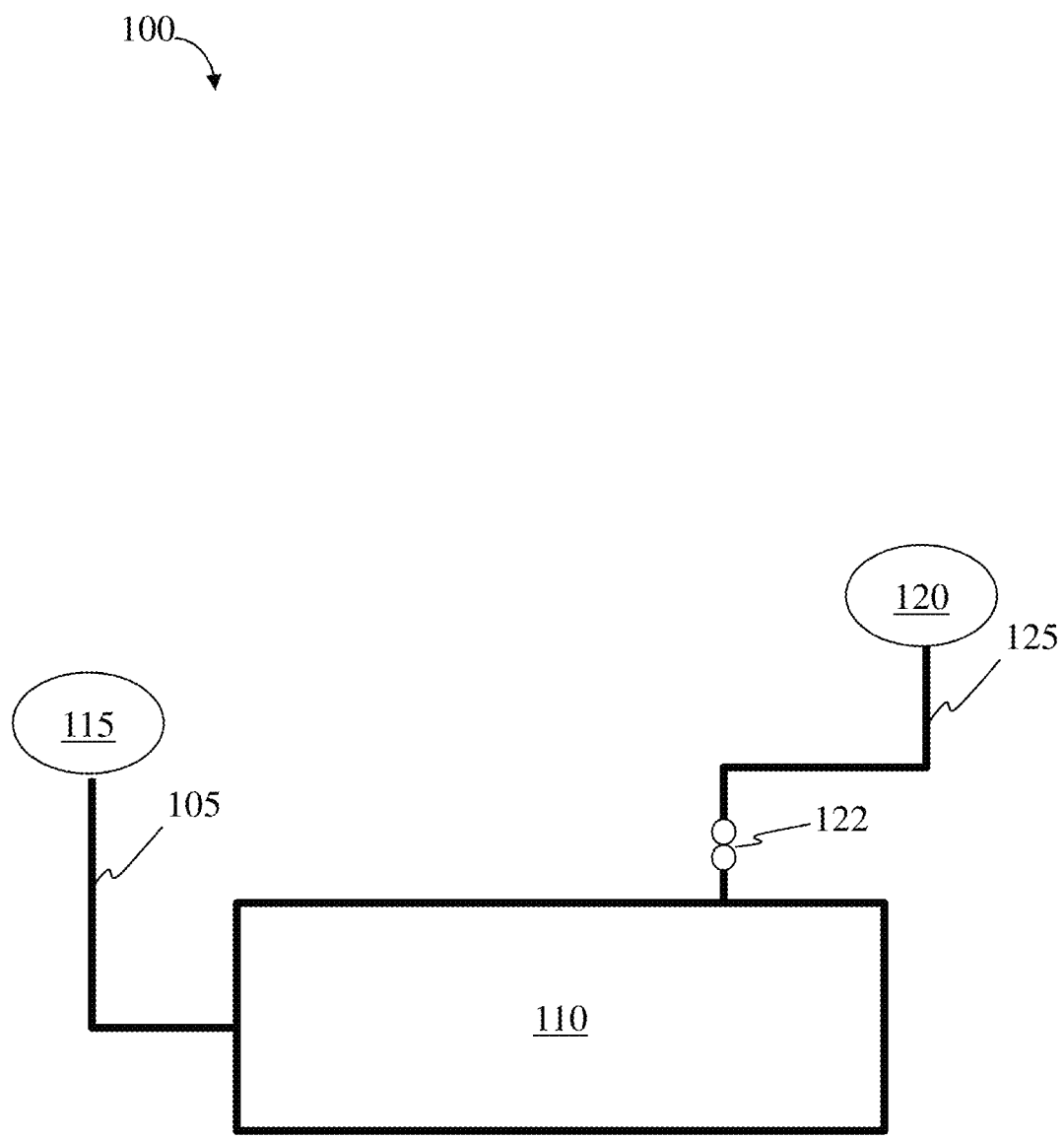
FIG. 1 is a schematic illustration of a fluidic device, according to one set of embodiments.

Fluidic devices and related methods are generally provided. The fluidic devices described herein may be useful, for example, for diagnostic purposes (e.g., detection of the presence of one or more disease causing bacteria in a patient sample). Unlike certain existing fluidic devices for diagnostic purposes, the fluidic devices and methods described herein may be useful for detecting the presence of numerous disease causing bacteria in a patient sample substantially simultaneously (e.g., in parallel). In addition, and beyond detection, the fluidic devices and methods described herein may be useful for monitoring microbial load, for example, monitoring changes in microbial loads from samples originating from multiple sources (e.g., bodily locations) and/or for monitoring changes in microbial load over time and/or in response to an applied treatment. The fluidic devices and methods described herein may be useful for determining quantitative effects of microbial load (e.g., as well as qualitative ones). In some embodiments, the fluidic devices and methods described herein, provide highly sensitive detection of microbes in relatively large fluidic samples (e.g., between 0.5 mL and about 5 mL), as compared to certain existing fluidic detection (e.g., microfluidic) devices and methods. In an exemplary embodiment, increased detection sensitivity of microbial pathogens present in a patient sample (e.g., blood) is performed by selectively removing human nucleic acid prior to sensitive detection of a microbial infection. In some embodiments, the fluidic device allows for the identification of microbial pathogens directly from unprocessed blood without having to conduct blood culturing processes. In some embodiments, the fluidic device allows for the identification of microbial pathogens directly from unprocessed blood without having to first centrifuge the blood.

In certain embodiments, the fluidic devices and methods described herein involve a unique approach to interfacing relatively large volumes (e.g., milliliters) of fluid with micro- or millimeter-scale fluidic channels. For instance, in some embodiments, a device described herein includes a series of fluidic reservoirs, which may be adapted and arranged to contain relatively large amounts (e.g., milliliters) of fluid such as reagents. Each fluidic reservoir may be connected to one or more fluidic channels. The device may also include one or more gas chambers in fluidic communication with a fluidic reservoir. The gas chambers may be used, for example, to pressurize the fluid in the reservoirs to promote fluid flow into and/or out of the fluidic channels. The fluidic channels may be connected to a fluidic hub, which may facilitate the flow of one or more fluids between two or more fluidic reservoirs. For instance, the fluidic hub may include a series of valves and/or channels that direct fluid flow to a particular reservoir for a particular operation (e.g., lysing, reaction, isolation, amplification, detection) to take place. A subsequent operation can then be performed by transporting the fluid back to the fluidic hub, via the fluidic channels, and into a different reservoir. In some cases, the fluidic hub may facilitate the transport of a gas to one or more reservoirs and, subsequently, to one or more gas chambers. The use of a fluidic device as described herein may facilitate the transport of a fluid between two or more reservoirs, without the use of multiple pumps and/or pressure sources. For example, in some cases, a constant pressure may be applied to the fluidic device and the plurality of valves may be opened in sequence such that the fluid is transported between two or more fluidic reservoirs (e.g., without the need to adjust, change, or redirect the pressure).

Advantageously, the devices and methods described herein may be useful for conducting a particular combinations of reactions and/or steps without the need for user intervention (e.g., automatically or semi-automatically), pipetting of individual reagents, or large-scale laboratory processes (e.g., centrifugation). As compared to fluidic devices for sample detection and analysis, the devices described herein may be, in some cases, stand-alone (e.g., do not require dedicated instrumentation).

In some embodiments, the fluidic device comprises a fluidic hub and a plurality of fluidic reservoirs. In certain embodiments, each fluidic reservoir is connected to a branching channel branching from the fluidic hub. For example, as illustrated in FIG. 1, fluidic device 100 comprises a fluidic hub 110 and a fluidic reservoir 120 connected to a branching channel 125 branching from, and in fluidic communication with, fluidic hub 110. In certain embodiments, a valve 122 may be positioned between branching channel 125 and fluidic hub 110. In alternative embodiments, however, no valve may be present between a branching channel and the fluidic hub.

In some cases, fluidic device 100 comprises fluidic reservoir 115 (e.g., a sample inlet reservoir) in fluidic communication with fluidic hub 110 via branching channel 105. In some such embodiments, a fluid may be introduced into the sample inlet reservoir and transported, via the fluidic hub, to a fluidic reservoir. For example, the fluid may be introduced to fluidic reservoir 115 and transported to the fluidic hub and subsequently, via opening of valve 122, to branching channel 125 and to fluidic reservoir 120. In some embodiments, a particular operation (e.g., lysing, reaction, isolation, amplification, detection) may be conducted in fluidic reservoir 120.

Figure 2:
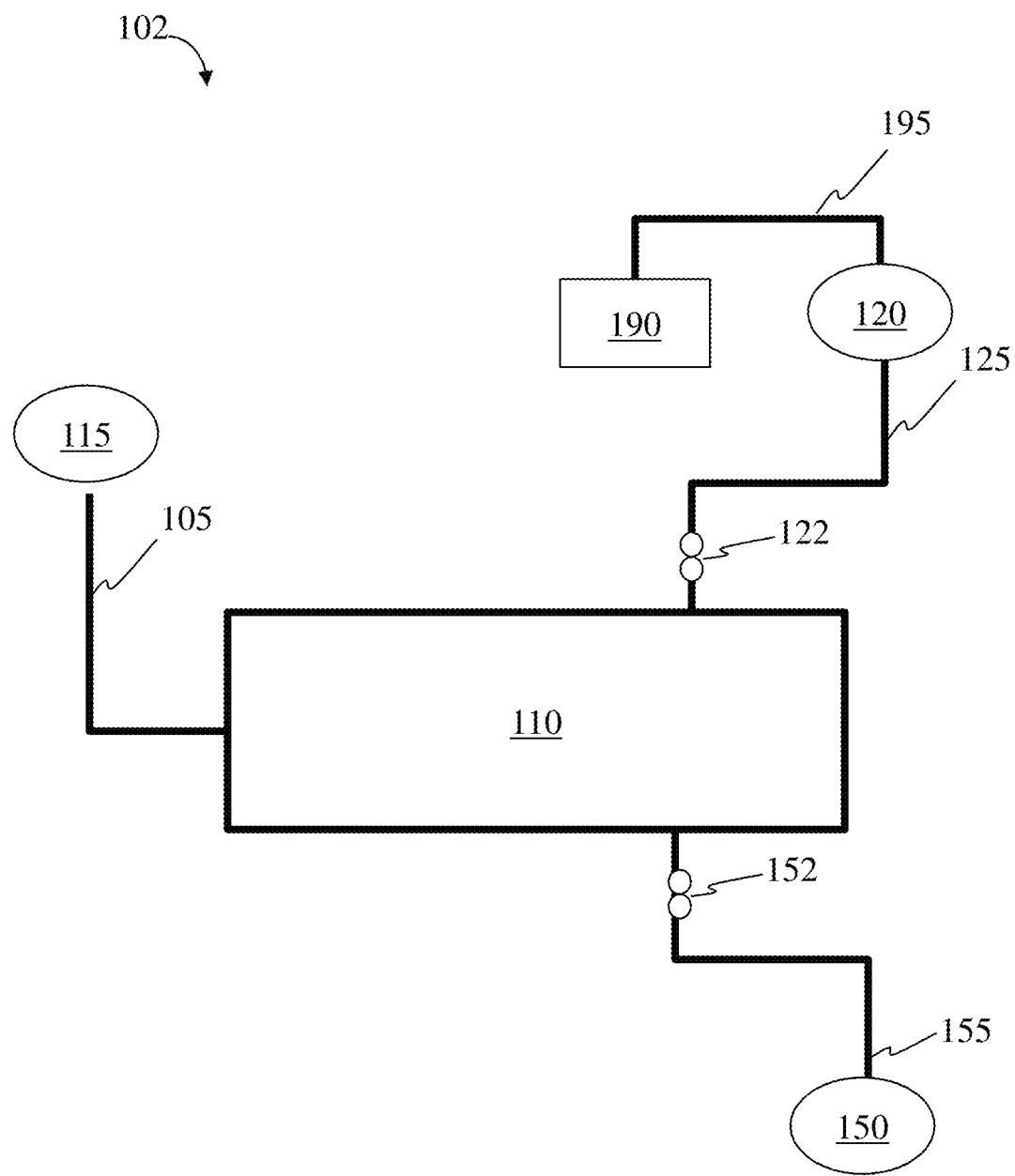
FIG. 2 is a schematic illustration of a fluidic device, according to one set of embodiments.

In some embodiments, a gas chamber may be in fluidic communication with the fluidic reservoir. For example, as illustrated in FIG. 2, fluidic device 102 comprises fluidic reservoir 120 in fluidic communication with a gas chamber 190. In some embodiments, a fluidic conduit (e.g., a fluidic channel) 195 facilitates the fluidic communication between gas chamber 190 and fluidic reservoir 120. In some embodiments, a gas may be flowed from gas chamber 190 to fluidic reservoir 120. In other embodiments, the gas may be flowed from fluidic reservoir 120 to gas chamber 190. In an exemplary embodiment, a gas may be introduced into fluidic hub 110 and transported to branching channel 125 via opening of valve 122, and subsequently transported to fluidic reservoir 120. In some such embodiments, the gas may then be transported from fluidic reservoir 120 to gas chamber 190. As described in more detail below, introducing a gas into the fluidic reservoir may aid in mixing of reagents in the fluidic reservoir.

Figure 3:
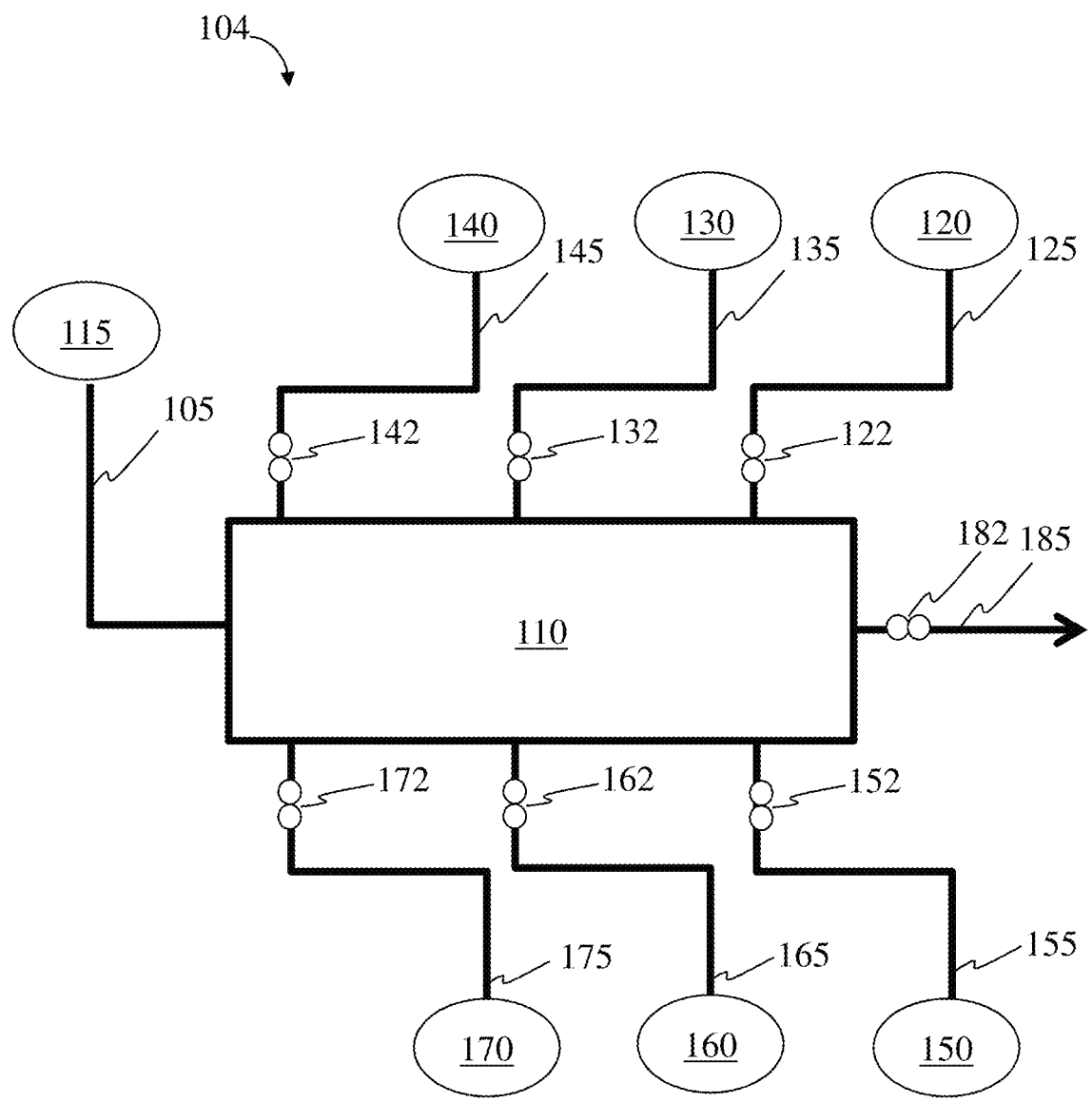
FIG. 3 is a schematic illustration of a fluidic device, according to one set of embodiments.

In certain embodiments, the fluidic device comprises a plurality of fluidic reservoirs and a plurality of branching channels branching from the fluidic hub. In some such embodiments, each fluidic reservoir may be in fluidic communication with the fluidic hub. In some embodiments, a branching channel may be in direct fluidic communication with the fluidic hub. In certain embodiments, one or more valves may be positioned between each branching channel and the fluidic hub. In an exemplary embodiment, as illustrated in FIG. 3, fluidic device 104 comprises a plurality of fluidic reservoirs including fluidic reservoir 115 (e.g., a sample inlet reservoir), fluidic reservoir 120, fluidic reservoir 130, fluidic reservoir 140, fluidic reservoir 150, fluidic reservoir 160, and fluidic reservoir 170. Each fluidic reservoir may be connected to fluidic hub 110 via branching channels 105, 125, 135, 145, 155, 165, and 175, respectively. In some cases, one or more fluidic reservoirs may contain a fluid (e.g., a reactant, a buffer). In certain embodiments, one or more fluidic reservoirs may be utilized for conducting a particular operation (e.g., lysing, isolation, amplification, and/or reacting). In some cases, a valve (e.g., valve 122, valve 132, valve 142, valve 152, valve 162, valve 172) may be positioned between a branching channel and the fluidic hub. In an exemplary embodiment, a fluid may be introduced into fluidic reservoir 115 and transported to fluidic hub 110 (via branching channel 105). In such embodiments, valve 122 may be opened (and several or all other valves closed) such that the fluid is transported from fluidic hub 110 to fluidic reservoir 120 (via branching channel 125). In certain embodiments, valve 132 may then be opened such that the fluid is transported from fluidic reservoir 120 (via branching channel 125) to fluidic hub 110 and into fluidic reservoir 130 (via branching channel 135).

The fluidic device may comprise any suitable number of branching channels. For example, in certain embodiments, the fluidic device comprises at least 2, at least 4, at least 5, at least 10, at least 20, at least 30, or at least 40 branching channels, each channel branching (e.g., extending) from the fluidic hub. In some embodiments, the fluidic device comprises less than or equal to 50, less than or equal to 40, less than or equal to 30, less than or equal to 20, less than or equal to 10, less than or equal to 5, or less than or equal to 4 branching channels, each channel branching from the fluidic hub. Combinations of the above-referenced ranges are also possible (e.g., at least 2 and less than or equal to 50). Other ranges are also possible.

In certain embodiments, the fluidic device comprises a plurality of fluidic reservoirs, each reservoir connected to a branching channel in fluidic communication with the fluidic hub. For example, in certain embodiments, the fluidic device comprises at least 2, at least 4, at least 5, at least 10, at least 20, at least 30, or at least 40 fluidic reservoirs, each reservoir in fluidic communication (e.g., connected to) a branching channel. In some embodiments, the fluidic device comprises less than or equal to 50, less than or equal to 40, less than or equal to 30, less than or equal to 20, less than or equal to 10, less than or equal to 5, or less than or equal to 4 fluidic reservoirs, each reservoir in fluidic communication (e.g., connected to) a branching channel. Combinations of the above-referenced ranges are also possible (e.g., at least 2 and less than or equal to 50). Other ranges are also possible.

In some cases, the fluidic device may comprise one or more additional chambers and/or regions in fluidic communication with the fluidic hub. For example, referring again to FIG. 3, in some embodiments (e.g., after conducting a series of operations in the plurality of fluidic reservoirs), a fluid may be transported from fluidic hub 110 to fluidic channel 185 (e.g., via opening of valve 182). Fluidic channel 185 may be in fluidic communication with, for example, one or more processing chambers and/or one or more detection regions, as described in more detail below.

In some cases, the gas chamber may be open to atmosphere (e.g., for venting of a gas). In certain embodiments, the gas chamber may be in fluidic communication with a pressure source, such that a pressure can be applied to a second fluid (e.g., a gas) within the gas chamber such that the second fluid pushes a first fluid contained within a fluidic reservoir in fluidic communication with the gas chamber.

As described above, in some embodiments, the fluidic device comprises a gas chamber in fluidic communication with a fluidic reservoir. In some embodiments, the gas chamber may have a particular volume. In certain embodiments, the gas chamber has a volume of at least 0.1 mL, at least 0.2 mL, at least 0.5 mL, at least 1 mL, at least 2 mL, or at least 5 mL. In certain embodiments, the gas chamber have a volume of less than or equal to 10 mL, less than or equal to 5 mL, less than or equal to 2 mL, less than or equal to 1 mL, less than or equal to 0.5 mL, or less than or equal to 0.2 mL. Combinations of the above referenced ranges are also possible (e.g., at least 0.1 mL and less than or equal to 10 mL). Other ranges are also possible.

As described above, in some embodiments, a fluid may be transported between the fluidic hub and one or more fluidic reservoirs. In some embodiments, the fluid may be reacted with a reagent present in the fluidic reservoir to form a reacted fluid in the fluidic reservoir. In some such embodiments, a pressure may be applied to the reacted fluid such that the reacted fluid flows into the fluidic hub. For example, in some embodiments, a pressure may be applied to a gas chamber in fluidic communication with the fluidic reservoirs such that the reacted fluid flows into the fluidic hub. In certain embodiments, the fluid may then be transported (e.g., by continuing to apply pressure) to one or more additional branching channels. For example, as illustrated in FIG. 2, a fluid may be flowed from fluidic hub 110 into fluidic reservoir 120 (via branching channel 125 upon opening of valve 122) and reacted with a reagent to form a reacted fluid. In some embodiments, a pressure may be applied to the reacted fluid via gas chamber 190 such that the reacted fluid flows from fluidic reservoir 120 and into fluidic hub 110. Upon opening of valve 152, the reacted fluid may flow from fluidic hub 110 and into branching channel 155. In some embodiments, the fluid may undergo a series of additional reactions and/or operations by flowing between one or more additional fluidic reservoirs. In an exemplary embodiment, the reacted fluid may be flowed from the second fluidic reservoir into the fluidic hub and subsequently flowed into a third fluidic reservoir (e.g., for reacting with one or more additional reagents).

In some embodiments, a constant differential pressure is applied to the various components (e.g., gas chambers, fluidic reservoirs, fluidic hub, and/or fluids contained therein) of the fluidic device. In certain embodiments, the opening and/or closing of one or more valves facilitates the flow of a fluid between one or more fluidic reservoirs and the fluidic hub. In some cases, the different pressure prohibits flow between one or more fluidic reservoirs. In some embodiments, the constant differential pressure is a positive pressure. In certain embodiments, the constant differential pressure is a negative pressure. In some cases, the constant differential pressure may be at least 0.1 psig, at least 0.2 psig, at least 0.3 psig, at least 0.5 psig, at least 0.8 psig, at least 1 psig, at least 2 psig, at least 5 psig, at least 10 psig, or at least 15 psig. In certain embodiments, the constant different pressure is less than or equal to 20 psig, less than or equal to 15 psig, less than or equal to 10 psig, less than or equal to 5 psig, 2 psig, less than or equal to 1 psig, less than or equal to 0.8 psig, less than or equal to 0.5 psig, less than or equal to 0.3 psig, or less than or equal to 0.2 psig. Combinations of the above-referenced ranges are also possible (e.g., at least 0.1 psig and less than or equal to 20 psig). Other ranges are also possible.

In some embodiments, a first fluid (e.g., a liquid) may be transported by pushing (i.e., displacing) the first fluid with a second fluid, immiscible with the first fluid. In certain embodiments, the second fluid is a gas. For example, in some embodiments, a fluidic reservoir may comprise the first fluid (e.g., a stored reagent) and a second fluid may be introduced into the fluidic reservoir, displacing the first fluid from the fluidic reservoir (e.g, into the fluidic hub via a branching channel). In certain embodiments, a fluidic channel (e.g., a branching channel) may comprise the first fluid and the second fluid may be introduced into the fluidic channel, displacing the first fluid from the branching channel (e.g., into a fluidic reservoir, into the fluidic hub). In some embodiments, a constant differential pressure may be applied to the second fluid such that the second fluid contacts and pushes the first fluid.

In an exemplary embodiment, a first fluid may be introduced into a first branching channel, and a second fluid in the first branching channel, while the first branching channel is in in fluidic communication with the fluidic hub. Referring again to FIG. 2, in some embodiments, branching channel 125 may be in fluidic communication with fluidic hub 110 (e.g., via opening of valve 122) and branching channel 155 may not be in fluidic communication with the fluidic hub (e.g., via closing of valve 152). In some such embodiments, a fluid present in branching channel 125 may be pushed by a second fluid introduced into branching channel 125 (e.g., from gas chamber 190 via fluidic conduit 195), and the fluid is pushed into fluidic hub 110. In some embodiments, the second fluid enters the fluidic hub.

In some embodiments, a fluidic reservoir may comprise a cover adjacent (e.g., directly adjacent) to the fluidic reservoir. As used herein, when a component is referred to as being "adjacent" another component, it can be directly adjacent to the component, or one or more intervening component also may be present. A component that is "directly adjacent" another component means that no intervening component is present. The cover may enclose and/or seal at least a portion of the reservoir (e.g., such that at least a first liquid is contained within the fluidic reservoir). For example, the cover may form a "wall" of the fluidic reservoir. In certain embodiments, the cover may be semipermeable. For example, in some embodiments, the cover is configured to restrict/prevent the flow of a first fluid through the cover (e.g., preventing flow of the first fluid through the cover at less than or equal to a particular applied pressure) while permitting the flow of a second fluid through the cover. In some such embodiments, the cover may comprise a semipermeable membrane.

Figure 11A:
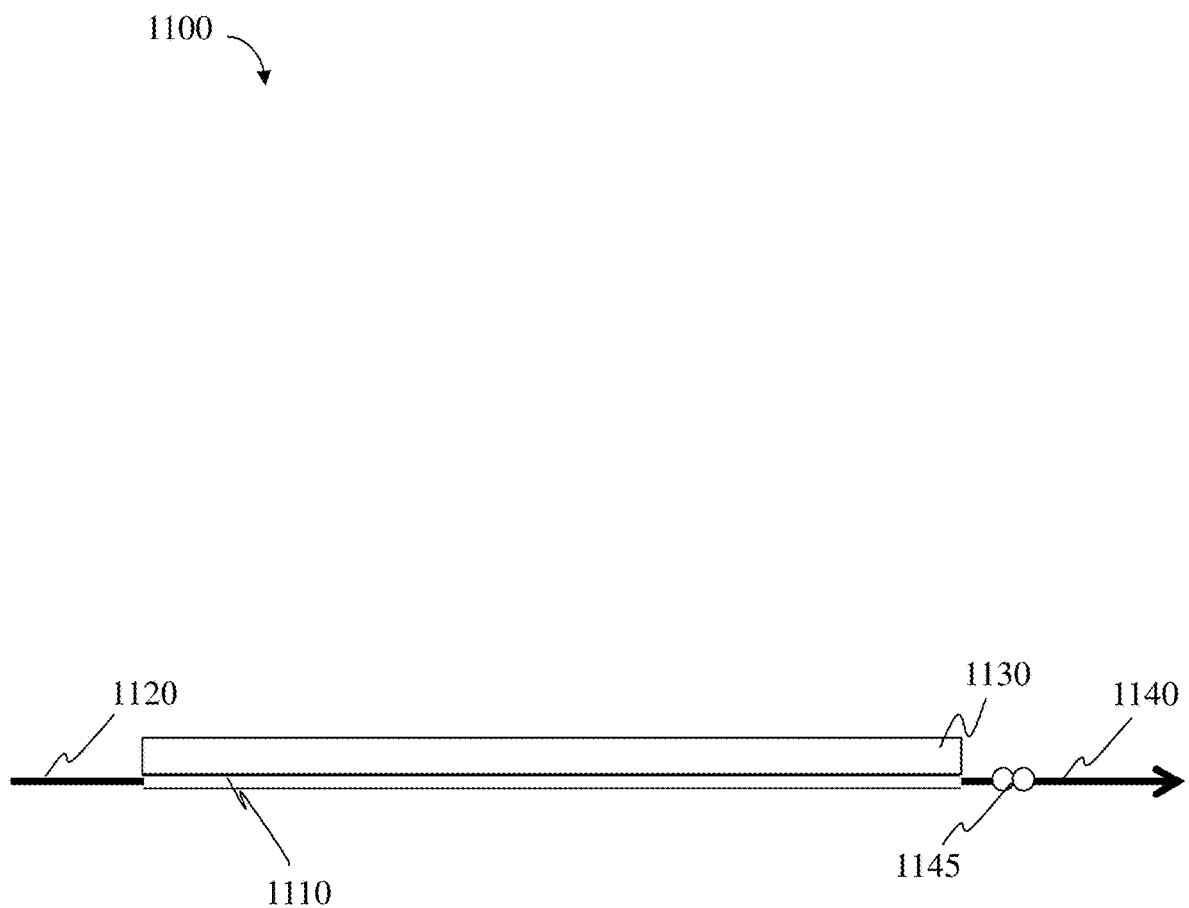
FIG. 11A is a schematic illustration of a portion of a fluidic device including a fluidic reservoir, according to one set of embodiments.

For example, as illustrated in FIG. 11A, a portion of a device 1100 may comprise a fluidic reservoir 1110 connected to a channel 1120 (e.g., an inlet channel) and a cover 1130 (e.g., a semipermeable membrane) adjacent to fluidic reservoir 1100. As shown illustratively in FIG. 11A, cover 1130 may enclose fluidic reservoir 1110. The cover may also enclose all or a portion of one or more channels (e.g., an inlet channel, an outlet channel) connected to the fluidic reservoir. In some embodiments, a channel 1140 (e.g., an outlet channel) may be in fluidic communication with fluidic reservoir 1110. In some cases, a valve 1145 may be associated with outlet channel 1145. Optionally, a valve may be associated with inlet channel 1120 (not shown).

In an exemplary embodiment, the cover adjacent the fluidic reservoir is semipermeable and, during use, permits the flow of a gas through the cover and prevents the flow of a liquid through the cover. For example, referring again to FIG. 11A, a gas (e.g., a second fluid) may be present in fluidic reservoir 1110. A first fluid (e.g., a liquid) may be introduced into the fluidic reservoir via channel 1120. In some embodiments, valve 1145 may be closed such that the first fluid does not enter outlet channel 1140. As the first fluid is introduced into the fluidic reservoir (e.g., via channel 1120), the cover may allow passage of the gas across the cover, e.g., the gas may flow through cover and exit fluidic the fluidic reservoir. In some such embodiments, the cover substantially prevents the first fluid from passing across the cover such that the first fluid is retained in the fluidic reservoir. Valve 1145 may be in a closed position to prevent the first fluid from entering channel 1140.

In some embodiments, the entire fluidic reservoir is filled with the first fluid. The closing of valve 1145 to prevent the first fluid from entering channel 1140 may enable only the fluidic reservoir to be filled with the first fluid. Advantageously, such a method may allow metering of fluids with good precision. For instance, by filling a fluidic reservoir having a known/particular volume with a fluid (e.g., a first fluid), the same volume of fluid may be measured in the fluidic system and used in a process described herein. After the desired amount of fluid enters the reservoir, the valve may be opened such that the first fluid is introduced into the outlet channel (e.g., for further processing). In some such embodiments, the second fluid (e.g., gas) that was previously in the fluidic reservoir does not enter channel 1140 since it was released from the fluidic reservoir through the cover.

In certain embodiments, a pressure may be applied to the first fluid such that the first fluid pushes the gas (e.g., the second fluid) through and across the cover (e.g., semipermeable membrane). In some embodiments, the applied pressure to the fluid may be greater than or equal to 0.2 psi, greater than or equal to 0.4 psi, greater than or equal to 0.6 psi, greater than or equal to 0.8 psi, greater than or equal to 1 psi, greater than or equal to 1.2 psi, greater than or equal to 1.4 psi, greater than or equal to 1.6 psi, greater than or equal to 1.8 psi, greater than or equal to 2 psi, greater than or equal to 2.5 psi, greater than or equal to 3 psi, greater than or equal to 3.5 psi, greater than or equal to 4 psi, or greater than or equal to 4.5 psi. In certain embodiments, applied pressure to the first fluid is less than or equal to 5 psi, less than or equal to 4.5 psi, less than or equal to 4 psi, less than or equal to 3.5 psi, less than or equal to 3 psi, less than or equal to 2.5 psi, less than or equal to 2 psi, less than or equal to 1.8 psi, less than or equal to 1.6 psi, less than or equal to 1.4 psi, less than or equal to 1.2 psi, less than or equal to 1 psi, less than or equal to 0.8 psi, less than or equal to 0.6 psi, or less than or equal to 0.4 psi. Combinations of the above-referenced ranges are also possible (e.g., greater than or equal to 0.4 psi and less than or equal to 5 psi, greater than or equal to 0.4 psi and less than or equal to 1 psi). Other ranges are also possible.

Figure 11B:
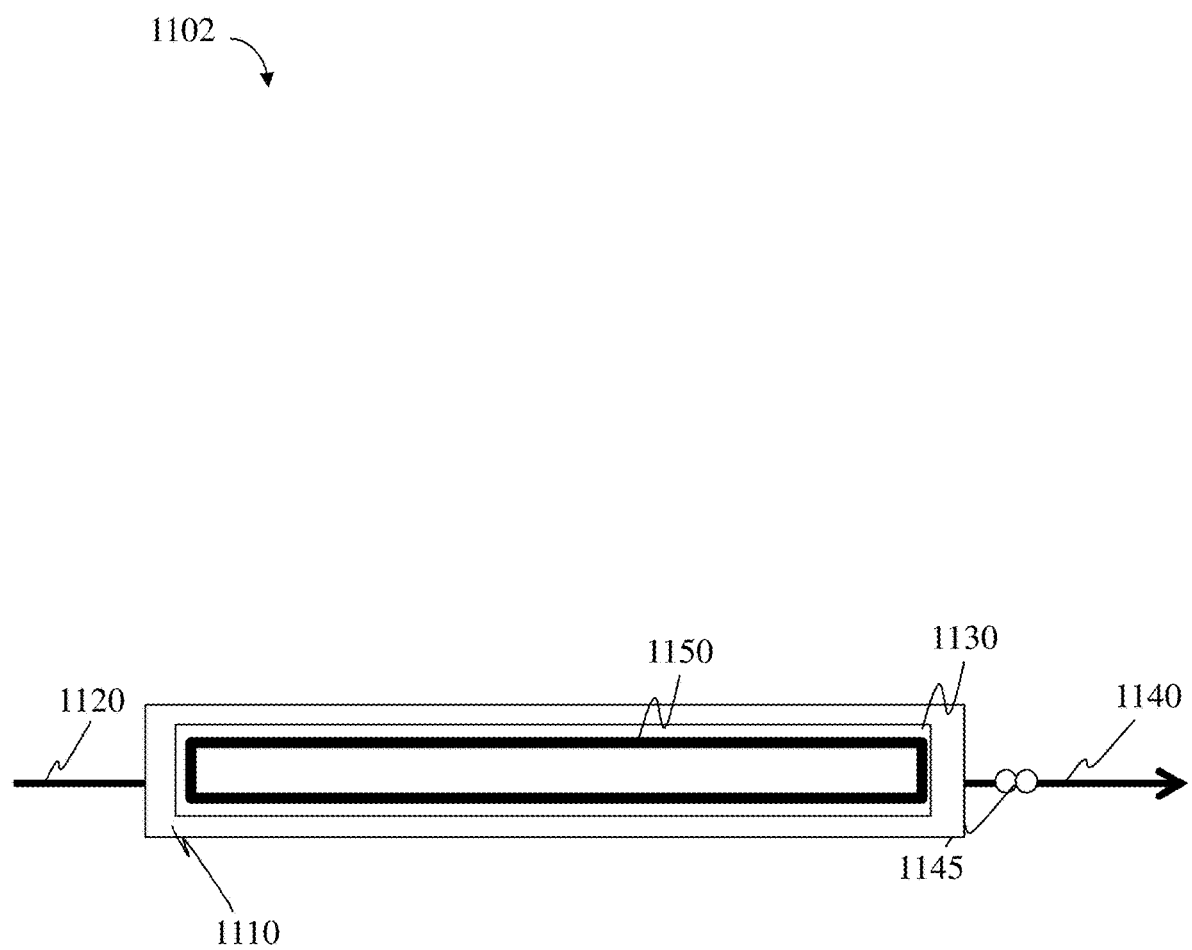
FIG. 11B is a schematic illustration of a portion of a fluidic device including a fluidic reservoir, according to one set of embodiments.

In some embodiments, the cover (e.g., semipermeable membrane) is configured to receive a sealing gasket. For example, the device may be inserted into an instrument comprising a sealing gasket. The sealing gasket may be, in some cases, brought into contact with at least a portion of the cover (e.g., semipermeable membrane) such that the cover (e.g., semipermeable membrane) maintains enclosure of the fluidic reservoir upon application of pressure to a fluid entering the fluidic reservoir (e.g., to prevent leakage of a fluid between the cover (e.g., semipermeable membrane) and the fluidic reservoir). For example, referring now to FIG. 11B showing a top view of a device portion 1102, a gasket 1150 may be brought into contact with cover (e.g., semipermeable membrane) 1130 adjacent fluidic reservoir 1110. In some embodiments, the gasket substantially circumvents the portion of the fluidic reservoir configured and designed to contain a fluid.

In some embodiments, at least a portion of the cover (e.g., semipermeable membrane) is adhered (e.g., via an adhesive and/or adhesive layer) to the fluidic reservoir. In certain embodiments, the adhesive and/or the sealing gasket maintains contact between the cover (e.g., semipermeable membrane) and the fluidic reservoir such that upon application of a pressure less than a liquid loss pressure of the device/assembly (e.g., less than or equal to 50 psi), at least a first fluid (e.g., a liquid) does not leak through or across the cover (e.g., semipermeable membrane) or between the cover (e.g., semipermeable membrane) and the fluidic reservoir.

Different liquid loss pressures of the device/assembly (e.g., at the fluidic reservoir, between the fluidic reservoir and the cover) may be possible. In some embodiments, the liquid loss pressure is less than or equal to 50 psi, less than or equal to 45 psi, less than or equal to 40 psi, less than or equal to 35 psi, less than or equal to 30 psi, less than or equal to 25 psi, less than or equal to 20 psi, less than or equal to 15 psi, less than or equal to 10 psi, less than or equal to 8 psi, less than or equal to 6 psi, or less than or equal to 4 psi. In certain embodiments, the liquid loss pressure is greater than or equal to 2 psi, greater than or equal to 4 psi, greater than or equal to 6 psi, greater than or equal to 8 psi, greater than or equal to 10 psi, greater than or equal to 15 psi, greater than or equal to 20 psi, greater than or equal to 25 psi, greater than or equal to 30 psi, greater than or equal to 35 psi, greater than or equal to 40 psi, or greater than or equal to 45 psi. Combinations of the above-referenced ranges are also possible (e.g., greater than or equal to 2 psi and less than or equal to 50 psi). Other ranges are also possible. The liquid loss pressure may be determined by contacting a gasket at a contact pressure of 5 psi with the cover (e.g., semipermeable membrane) adjacent the fluidic reservoir and introducing water into the fluidic reservoir under continuously increasing pressure until the fluid is observed to begin leaking from between the cover (e.g., semipermeable membrane) and the fluidic reservoir. The pressure at which the fluid is observed to leak is equal to the liquid loss pressure.

Advantageously, the use of covers such as semipermeable membranes as described herein may reduce or prevent the formation of bubbles in channels fluidically connected to the fluidic reservoir (e.g., during flow of a fluid from the fluidic reservoir into the channel(s)) and/or may enable the metering of a fluid (e.g., such that the fluid fills the fluidic reservoir without the presence of a gas in the fluidic reservoir).

In certain embodiments, the cover is a semipermeable membrane having a particular air permeability. In some embodiments, the air permeability of the cover (e.g., semipermeable membrane) is, at 1 psi, greater than or equal to 0.4 slpm, greater than or equal to 0.6 slpm, greater than or equal to 0.8 slpm, greater than or equal to 1 slpm, greater than or equal to 1.2 slpm, greater than or equal to 1.4 slpm, greater than or equal to 1.6 slpm, greater than or equal to 1.8 slpm, greater than or equal to 2 slpm, greater than or equal to 2.5 slpm, greater than or equal to 3 slpm, greater than or equal to 3.5 slpm, greater than or equal to 4 slpm, or greater than or equal to 4.5 slpm. In certain embodiments, the air permeability of the cover (e.g., semipermeable membrane), at 1 psi, is less than or equal to 5 slpm, less than or equal to 4.5 slpm, less than or equal to 4 slpm, less than or equal to 3.5 slpm, less than or equal to 3 slpm, less than or equal to 2.5 slpm, less than or equal to 2 slpm, less than or equal to 1.8 slpm, less than or equal to 1.6 slpm, less than or equal to 1.4 slpm, less than or equal to 1.2 slpm, less than or equal to 1 slpm, less than or equal to 0.8 slpm, or less than or equal to 0.6 slpm. Combinations of the above-referenced ranges are also possible (e.g., greater than or equal to 0.4 slpm and less than or equal to 5 slpm at 1 psi, greater than or equal to 0.4 slpm and less than or equal to 1 slpm at 1 psi). Other ranges are also possible. Air permeability may be determined according to ASTM standard F788-88 (2014) at 1 psi.

In some embodiments, the cover/semipermeable membrane may have a particular water intrusion pressure. In certain embodiments, the cover (e.g., semipermeable membrane) has a water intrusion pressure of greater than or equal to 2 psi, greater than or equal to 4 psi, greater than or equal to 6 psi, greater than or equal to 8 psi, greater than or equal to 10 psi, greater than or equal to 15 psi, greater than or equal to 20 psi, greater than or equal to 25 psi, greater than or equal to 30 psi, greater than or equal to 35 psi, greater than or equal to 40 psi, greater than or equal to 45 psi, greater than or equal to 50 psi, greater than or equal to 55 psi, greater than or equal to 60 psi, greater than or equal to 65 psi, greater than or equal to 70 psi, greater than or equal to 75 psi, greater than or equal to 80 psi, greater than or equal to 85 psi, greater than or equal to 90 psi, greater than or equal to 95 psi, greater than or equal to 100 psi, greater than or equal to 105 psi, greater than or equal to 110 psi, or greater than or equal to 115 psi. In some embodiments, the cover (e.g., semipermeable membrane) has a water intrusion pressure of less than or equal to 120 psi, less than or equal to 115 psi, less than or equal to 110 psi, less than or equal to 105 psi, less than or equal to 100 psi, less than or equal to 95 psi, less than or equal to 90 psi, less than or equal to 85 psi, less than or equal to 80 psi, less than or equal to 75 psi, less than or equal to 70 psi, less than or equal to 65 psi, less than or equal to 60 psi, less than or equal to 55 psi, less than or equal to 50 psi, less than or equal to 45 psi, less than or equal to 40 psi, less than or equal to 35 psi, less than or equal to 30 psi, less than or equal to 25 psi, less than or equal to 20 psi, less than or equal to 15 psi, less than or equal to 10 psi, less than or equal to 8 psi, less than or equal to 6 psi, or less than or equal to 4 psi. Combinations of the above-referenced ranges are also possible (e.g., greater than or equal to 2 psi and less than or equal to 120 psi, greater than or equal to 15 psi and less than or equal to 120 psi, greater than or equal to 25 psi and less than or equal to 120 psi greater than or equal to 45 psi and less than or equal to 120 psi, greater than or equal to 70 psi and less than or equal to 120 psi). Other ranges are also possible. Water intrusion pressure may be determined using the Millipore HydroCorr Water Flow Integrity Test according to, for example, U.S. Pat. No. 5,786,528, issued on Jul. 28, 1998, and entitled "Water Intrusion Test For Filters", which is incorporated herein by reference in its entirety for all purposes.

In some cases, the cover (e.g., semipermeable membrane) has a particular mean pore size. In some embodiments, the mean pore size of the cover (e.g., semipermeable membrane) is greater than or equal to 0.02 microns, greater than or equal to 0.04 microns, greater than or equal to 0.06 microns, greater than or equal to 0.08 microns, greater than or equal to 0.1 micron, greater than or equal to 0.15 microns, greater than or equal to 0.2 microns, greater than or equal to 0.25 microns, greater than or equal to 0.3 microns, greater than or equal to 0.3 microns, greater than or equal to 0.4 microns, or greater than or equal to 0.45 microns. In certain embodiments, the mean pore size of the cover (e.g., semipermeable membrane) is less than or equal to 0.5 microns, less than or equal to 0.45 microns, less than or equal to 0.4 microns, less than or equal to 0.35 microns, less than or equal to 0.3 microns, less than or equal to 0.25 microns, less than or equal to 0.2 microns, less than or equal to 0.15 microns, less than or equal to 0.1 microns, less than or equal to 0.08 microns, less than or equal to 0.06 microns, or less than or equal to 0.04 microns. Combinations of the above referenced ranges are also possible (e.g., greater than or equal to 0.02 microns and less than or equal to 0.5 microns). Other ranges are also possible.

The cover (e.g., semipermeable membrane) may comprise any suitable material. Non-limiting examples of suitable materials include fluorinated materials such as polyvinylidene fluoride (PVDF). In an exemplary embodiment, the semipermeable membrane is a commercially available membrane such as the SureVent® PVDF membranes (Millipore, Billerica, Mass.).

In some embodiments, the cover (e.g., semipermeable membrane) is hydrophobic. In certain embodiments, the semipermeable membrane is superhydrophobic. The term "superhydrophobic" refers to a material having an equilibrium water contact angle of greater than 150 degrees, as determined by contact angle goniometry.

In some embodiments, the first fluid (e.g., the first fluid pushed by the second fluid) may have a particular volume. For example, in some embodiments, the first fluid has a volume of at least 0.1 mL, at least 0.2 mL, at least 0.5 mL, at least 1 mL, at least 2 mL, or at least 5 mL. In certain embodiments, the first fluid may have a volume of less than or equal to 10 mL, less than or equal to 5 mL, less than or equal to 2 mL, less than or equal to 1 mL, less than or equal to 0.5 mL, or less than or equal to 0.2 mL. Combinations of the above referenced ranges are also possible (e.g., at least 0.1 mL and less than or equal to 10 mL). Other ranges are also possible.

In some embodiments, the second fluid is immiscible with the first fluid. In certain embodiments, the second fluid comprises a gas (e.g., a sterilized gas). In certain traditional fluidic (e.g., microfluidic) devices it is generally undesirable to flow gases in the system since they can introduce air bubbles that can inhibit flow of liquids. Advantageously, the use of gases in the fluidic devices described herein may be useful for facilitating the flow of one or more fluids within the system and/or to promote mixing of fluids as described in more detail herein.

As described above, in some embodiments, the fluidic device comprises at least one fluidic channel in fluidic communication with a fluidic reservoir. A fluidic channel described herein (e.g., a branching channel, a hub channel) can have a particular average cross-sectional dimension. The "cross-sectional dimension" (e.g., a diameter, a width) of the channel is measured perpendicular to the direction of fluid flow. In some embodiments, the average cross-sectional dimension of the at least one channel is less than or equal to about 3 mm, less than or equal to about 2 mm, less than or equal to about 1 mm, less than or equal to about 800 microns, less than or equal to about 600 microns, less than or equal to about 500 microns, less than or equal to about 400 microns, less than or equal to about 300 microns, less than or equal to about 200 microns, less than or equal to about 175 microns, less than or equal to about 150 microns, or less than or equal to about 125 microns. In certain embodiments, the average cross-sectional dimension of the at least one channel is greater than or equal to about 100 microns, greater than or equal to about 125 microns, greater than or equal to about 150 microns, greater than or equal to about 175 microns, greater than or equal to about 200 microns, greater than or equal to about 250 microns, greater than or equal to about 300 microns, greater than or equal to about 400 microns, greater than or equal to about 500 microns, greater than or equal to about 600 microns, greater than or equal to about 800 microns, greater than or equal to about 1 mm, or greater than or equal to about 2 mm. Combinations of the above-referenced ranges are also possible (e.g., between about 250 microns and about 2 mm, between about 400 microns and about 1 mm, between about 300 microns and about 600 microns). Other ranges are also possible. The dimensions of the channel may also be chosen, for example, to allow a certain volumetric or linear flowrate of fluid in the channel and/or to hold a certain volume of fluid in the channel. Of course, the number of channels and the shape of the channels can be varied by any method known to those of ordinary skill in the art. The fluidic channel can have any cross-sectional shape (circular, oval, triangular, irregular, trapezoidal, square or rectangular, or the like).

One or more fluidic channels may also have a channel length-to-width ratio (length to average cross sectional dimension) of at least 5:1, at least 6:1, at least 8:1, at least 10:1, at least 20:1, at least 50:1, or at least 100:1.

A fluidic channel can have any suitable volume. In some embodiments, the volume of a fluidic channel (e.g., a branching channel, a hub channel) may be at least 0.1 microliters, at least 0.5 microliters, at least 1 microliter, at least 2 microliters, at least 5 microliters, at least 10 microliters, at least 25 microliters, at least 50 microliters, at least 100 microliters, at least 200 microliters, at least 500 microliters, or at least 1000 microliters. In certain embodiments, the volume of one or more fluidic channels may be less than or equal to 2000 microliters, less than or equal to 1000 microliters, less than or equal to 500 microliters, less than or equal to 200 microliters, less than or equal to 100 microliters, less than or equal to 50 microliters, less than or equal to 25 microliters, less than or equal to 10 microliters, less than or equal to 5 microliters, less than or equal to 2 microliters, less than or equal to 1 microliter, or less than or equal to 0.5 microliters. Combinations of the above referenced ranges are also possible (e.g., at least 0.1 microliters and less than or equal to 2000 microliters, at least 0.1 microliters and less than or equal to 1000 microliters). Other ranges are also possible.

A fluidic channel (e.g., a branching channel, a hub channel) may also have any suitable length. In some embodiments, one or more fluidic channels have a length of at least 1 cm, at least 2 cm, at least 5 cm, at least 10 cm, or at least 20 cm. In certain embodiments, one or more fluidic channels may have a length of less than or equal to 30 cm, less than or equal to 10 cm, less than or equal to 5 cm, or less than or equal to 2 cm. Combinations of the above-referenced ranges are possible (e.g., at least 1 cm and less than or equal to 30 cm). Other ranges are also possible.

Figure 4:
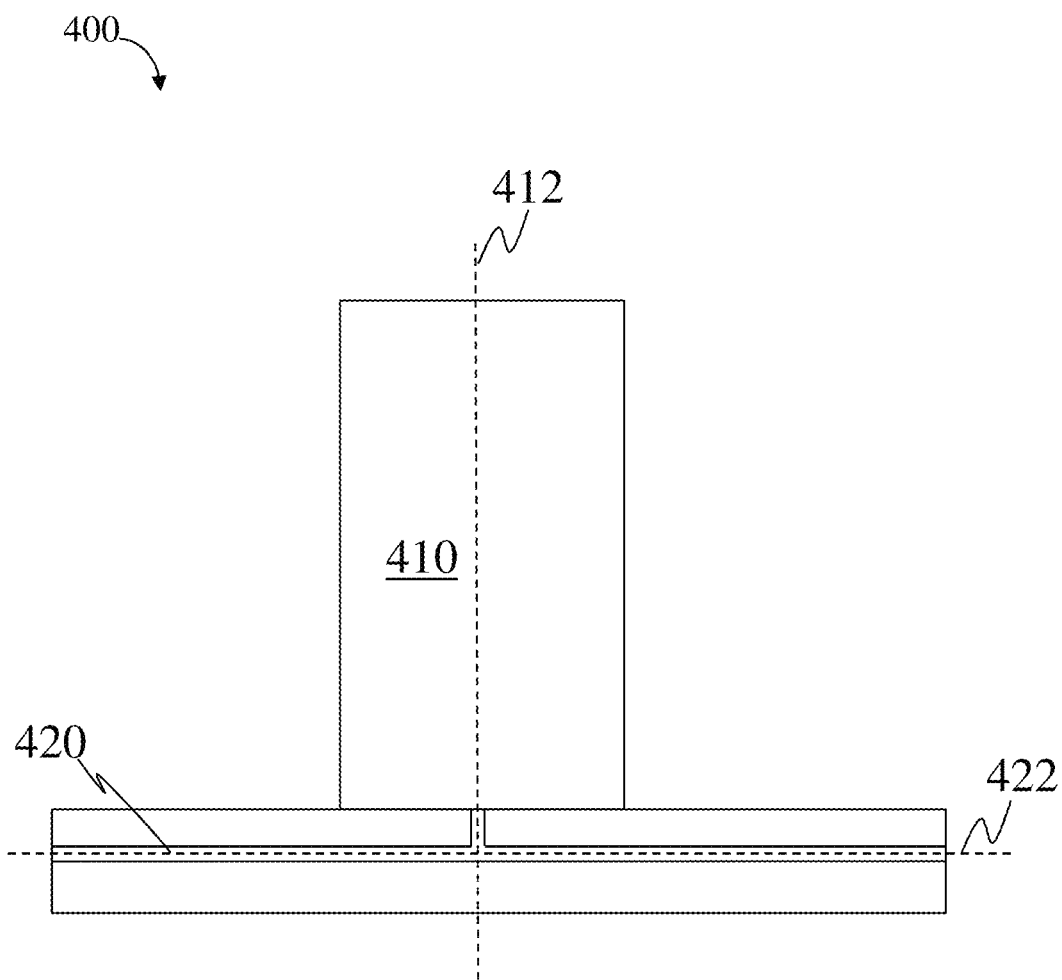
FIG. 4 is a schematic illustration of a fluidic device, according to one set of embodiments.

In some embodiments, a longitudinal axis of at least one fluidic channel is substantially perpendicular to a longitudinal axis (e.g., height) of at least one fluidic reservoir. For example, as illustrated in FIG. 4, fluidic device 400 comprises fluidic reservoir 410 and fluidic channel 420. In some embodiments, longitudinal axis 412 of fluidic reservoir 410 is substantially perpendicular to longitudinal axis 422 of fluidic channel 420. As shown illustratively in this figure, the longitudinal axis 412 of fluidic reservoir 412 lies on a different plane than longitudinal axis 422 of fluidic channel 420. By extending the longitudinal axis (e.g., height) of the reservoir, this configuration may allow the fluidic reservoir to hold a greater amount of volume compared to a configuration in which the longitudinal axes of the fluidic reservoir and the fluidic channel (connected to the fluidic reservoir) are on the same plane or are parallel to one another.

In some embodiments, at least one fluidic channel described above is a branching channel. In certain embodiments, the fluidic hub is a fluidic channel, as described herein (e.g., having a length of at least 1 cm).

In some embodiments, each fluidic reservoir may have a particular volume. For example, in some embodiments, each fluidic reservoir may have a volume of at least 0.1 mL, at least 0.2 mL, at least 0.5 mL, at least 1 mL, at least 2 mL, at least 5 mL, at least 10 mL, at least 25 mL, or at least 50 mL. In certain embodiments, each fluidic reservoir may have a volume of less than or equal to 100 mL, less than or equal to 50 mL, less than or equal to 25 mL, less than or equal to 10 mL, less than or equal to 5 mL, less than or equal to 2 mL, less than or equal to 1 mL, less than or equal to 0.5 mL, or less than or equal to 0.2 mL. Combinations of the above referenced ranges are also possible (e.g., at least 0.1 mL and less than or equal to 100 mL, at least 0.5 mL and less than or equal to 2 mL). Other ranges are also possible.

In some embodiments, a longitudinal axis of the fluidic reservoir may be oriented perpendicular to a longitudinal axis of at least one fluidic channel in fluidic communication with the fluidic reservoir (e.g., as shown illustratively in FIG. 4). In other embodiments, a longitudinal axis of the fluidic reservoir may be oriented parallel to a longitudinal axis of at least one fluidic channel in fluidic communication with the fluidic reservoir (e.g., as shown illustratively in FIGS. 11A-11B). In some cases, a longitudinal axis of the fluidic reservoir may reside in the same plane as a longitudinal axis of at least one fluidic channel in fluidic communication with the fluidic reservoir.

In certain embodiments, the fluidic reservoir may have a particular shape (e.g., when viewed from a top view). In some embodiments, the fluidic reservoir may have a cylindrical shape, a cubic shape, a cuboidal shape, a prismatic shape, or a conical shape. In an exemplary embodiment, the fluidic reservoir has a cylindrical shape. In another exemplary embodiment, the fluidic reservoir has a cuboidal shape. Other shapes are also possible.

In some embodiments, the fluidic reservoir may have a particular cross-sectional shape. For example, in some cases, at least one cross-section of the fluidic reservoir may be rectangular shaped, square shaped, triangular shaped, circular shaped, U-shaped, serpentine shaped, hexagonal shaped, or irregularly shaped. In an exemplary embodiment, the fluidic reservoir may have a U-shaped cross-sectional shape (e.g., when viewed from the top view of the fluidic channel). Other cross-sectional shapes are also possible.

In some embodiments, a fluidic reservoir may be a storage reservoir (e.g., for storing one or more reagents for conducting a particular operation). The reagent may be stored and sealed in the fluidic reservoir, e.g., prior to use of the fluidic device by the user and/or prior to insertion of a sample into the device. In some embodiments, one or more reagents contained within a fluidic reservoir may be a liquid reagent (e.g., a wash buffer, a lysis reagent, an isolation reagent). In certain embodiments, one or more reagents contained within a fluidic reservoir may be a dry, lyophilized, and/or pelleted reagent. In some such embodiments, the stored reagent may be suspended (e.g., upon introduction of a fluid into the fluidic reservoir containing the stored reagent).

In some cases, a fluidic reservoir may define a region for conducting a particular operation. In some embodiments, a fluidic reservoir may be reused and define a region for conducting more than one operation. In some cases, one or more operations may be conducted in parallel (e.g., in one or more fluidic reservoirs).

In some cases, a fluidic reservoir may be reused for two or more operations. In certain embodiments, a first fluidic reservoir may be used for a first reaction and, after the fluid has been flowed to one or more additional fluidic reservoirs, the fluid may be flowed again to the first fluidic reservoir for conducting a second reaction, the same or different than the first reaction. In an exemplary embodiment, a first operation such as lysing may be conducted in the first fluidic reservoir, and after the fluid has been flowed to one or more additional fluidic reservoirs (e.g., for conducting one or more particular operations), the fluid may be flowed to the first fluidic reservoir for a second operation such as mixing. Those skilled in the art would understand that using the fluidic reservoir for lysing and mixing operations are by way of example only, and that one or more operations described herein may be conducted in the same or different reservoirs. In some cases, the fluidic reservoir may be reused as a waste reservoir (e.g., for storing waste fluids remaining after a particular operation conducted in a different reservoir). Advantageously, the ability to reuse one or more fluidic reservoirs as a waste reservoir may, for example, reduce the size and cost of the fluidic device as compared to other fluidic devices for sample detection and analysis, and/or may remove the need to removal of waste products and/or fluids during operation of the fluidic device.

It should be appreciated although detection is primarily described herein, in some embodiments, the fluidic devices and methods described herein may be used for monitoring various processes, events or conditions such as microbial load. For example, a device or method may be used for monitoring changes in microbial loads from samples originating from multiple sources (e.g., bodily locations) and/or for monitoring changes in microbial load over time and/or in response to an applied treatment. The fluidic devices and methods described herein may be used for determining quantitative effects of microbial load (e.g., as well as qualitative ones) in some embodiments. Monitoring may occur in a single detection event, periodically or continuously.

In certain embodiments, one or more fluidic reservoirs and/or one or more fluidic channels may be heated. In some embodiments, the fluidic reservoirs and/or one or more fluidic channels may be heated by one or more heating elements proximate the fluidic reservoir including, for example, resistance heaters, thermo-electric heaters, optical heaters, or the like. In some embodiments, one or more fluidic reservoirs (or one or more fluids contained and/or stored therein) may be heated to a particular temperature (e.g., for a given operation such as lysing, isolation, amplification, detection). For example, in certain embodiments, one or more fluidic reservoirs and/or one or more fluidic channels may be heated to at least 5° C., at least 10° C., at least 15° C., at least 20° C., at least 25° C., at least 30° C., at least 35° C., at least 37° C., at least 40° C., at least 50° C., at least 60° C., at least 70° C., at least 75° C., at least 80° C., at least 85° C., at least 90° C., at least 95° C., at least 100° C., or at least 110° C. In certain embodiments, one or more fluidic reservoirs and/or one or more fluidic channels may be heated to a temperature of less than or equal to 120° C., less than or equal to 110° C., less than or equal to 100° C., less than or equal to 95° C., less than or equal to 90° C., less than or equal to 85° C., less than or equal to 80° C., less than or equal to 75° C., less than or equal to 70° C., less than or equal to 60° C., less than or equal to 50° C., less than or equal to 40° C., less than or equal to 37° C., less than or equal to 35° C., less than or equal to 30° C., less than or equal to 25° C., less than or equal to 20° C., less than or equal to 15° C., or less than or equal to 10° C. Combinations of the above-referenced ranges are possible (e.g., at least 5° C. and less than or equal to 100° C.). Other ranges are also possible. In some cases, the temperature may be cycled (e.g., during an amplification operation). For example, in some embodiments, the temperature may be cycled between 50° C. and 120° C., or between 70° C. and 120° C. and at about 25° C. and 75° C.

In some embodiments, a valve may be positioned between a branching channel and the fluidic hub. For example, referring again to FIG. 1, in certain embodiments, a valve 122 may be positioned between branching channel 125 and fluidic hub 110. In some embodiments, the valve is a flow-gate. In certain embodiments, the valve may be a membrane-based valve. For example, a piston may be disposed on the membrane-based valve such that the valve is closed. In certain embodiments, the piston may be raised such that the valve is opened. Other flow-restricting valves are also possible including, but not limited to, miniature solenoids, manifolds, deformable gels, and/or membranes to control the passage or flow of fluid from the fluidic hub to one or more branching channels. In some embodiments, the fluidic devices and/or methods described herein may comprise one or more valves (e.g., flow-gates) described in U.S. Pat. No. 9,132,426, issued Sep. 15, 2015, and entitled "Simplified gating method for sealing and flow control in micro and nano devices", which is incorporated herein by reference in its entirety for all purposes. Other valves are also possible.

In some cases, the fluidic conduit positioned between a gas chamber and a fluidic reservoir comprises a valve (e.g., a flow-gate).

In some embodiments, the fluidic device comprises one or more lysis regions. In some embodiments, one or more lysis regions are in fluidic communication with a fluidic channel (e.g., a fluidic hub). In certain embodiments, one or more lysis regions are in fluidic communication with an isolation region, as described herein. In some cases, one or more lysis regions may be in fluidic communication with one or more additional regions comprising one or more fluidic reservoirs described herein. In some embodiments, one or more lysis regions may be in fluidic communication with the fluidic hub. In certain embodiments, the lysing operation comprises chemical lysing, including, for example, exposing a patient's sample to a chemical lysing reagent that results in the opening or rupturing of a cell membrane of the select eukaryotic cell. In certain embodiments, the fluidic reservoir contains one or more lysing reagents (e.g., stored lysing reagents) prior to the flow of the sample to the fluidic reservoir. In other embodiments, one or more lysing reagents may be added to the fluidic reservoir after the flow of the sample to the fluidic reservoir. Referring again to FIG. 3, in an exemplary embodiment, fluidic device 104 comprises a first lysis region comprising fluidic reservoir 120 for conducting a first lysing operation and a second lysis region comprising fluidic reservoir 130 for conducting a second lysing operation. In some embodiments, the first lysis region comprises one or more stored lysing reagents. In certain embodiments, the second lysis region comprises one or more stored lysing reagents, which may be the same or different from the lysing reagents in the first lysis region. In some cases, the fluid (e.g., the sample) may be flowed to the first lysis region and one or more lysing reagents may be added to the first lysis region (e.g., a lysing reagent(s) flowed from one or more additional fluidic reservoirs including the lysing reagent(s)). In some cases, the fluid (e.g., the sample) may be flowed to the second lysis region and one or more lysing reagents may be added to the second lysis region (e.g., lysing reagent(s) flowed from one or more additional fluidic reservoirs including the lysing reagent(s)).

In some embodiments, one or more lysing operations comprises the lysing of select eukaryote cells (e.g., select eukaryote cells present in a patient's sample). In some embodiments, the lysing operation releases mammalian DNA from the sample (e.g., such that it may be isolated and/or removed from the sample). In certain embodiments released select eukaryote DNA may be isolated and/or removed from the sample after lysing thus depleting the select eukaryote genomic material from the sample.

In some embodiments, the lysing operation comprises the lysing of one or more microbial cells. In some embodiments, the lysing operation releases microbial genomic material from the microbial cells into the fluid (e.g., such that it may be isolated, amplified, and/or detected). In some cases, lysing of one or more microbial cells occurs after the lysing of select eukaryote cells. In some such embodiments, prior to lysing of one or more microbial cells, the sample has been substantially depleted of select eukaryote DNA. In alternative embodiments, lysing of one or more microbial cells in conducting without the lysing of select eukaryote cells. In certain embodiments, after lysing of select eukaryote cells, but prior to lysing of the microbial cells, at least a portion of the microbial cells may be intact (e.g., unlysed).

Non-limiting examples of suitable chemical lysing reagents include cationic detergents, non-ionic detergents, zwitterionic detergents, enzymes, and combinations thereof. In some embodiments, the chemical lysing reagent also includes one or more of enzymes, detergents, salts, buffering agents, metal chelators, and/or combinations thereof.

In some cases, the lysing operation comprises mechanical lysing including, for example, ultrasonic agitation and/or bead-beating. In some embodiments, the first lysing operation comprises thermal lysing including, for example, heat shock. Combinations of chemical, mechanical, or thermal lysing operations are also possible. Other processes for lysing of cells are known in the art.

In some embodiments, one or more lysing operations are conducted at a temperature of between about 15° C. to 50° C., about 20° C. to 45° C., about 25° C. to 40° C., or about 30° C. to 35° C. Other ranges are also possible. In some embodiments, one or more lysing operations are performed at room temperature.

In some embodiments, the microbial cell lysis methods disclosed herein, lead to the release of high molecular weight microbial DNA. Without wishing to be beyond by theory, in some embodiments, the microbial cell lysis methods disclosed herein lead to reduced shearing of microbial genomic materials during the microbial cell lysis and promote the presence of high molecular weight microbial DNA in the lysed fluid. In some embodiments, high molecular weight microbial DNA is between about 2 kbp to 200 kbp, about 10 kbp to 190 kbp, about 20 kbp to 180 kbp, about 30 kbp to 170 kbp, about 40 kbp to 160 kbp, about 50 kbp to 150 kbp, about 60 kbp to 140 kbp, about 70 kbp to 130 kbp, about 80 kbp to 120 kbp, or about 90 kbp to 110 kbp.

In some embodiments, the fluidic device comprises one or more isolation regions. In certain embodiments, one or more isolation regions are in fluidic communication with one or more lysis regions. In some embodiments, one or more isolation regions may be in fluidic communication with the fluidic hub. In some cases, one or more isolation regions may be in fluidic communication with one or more additional regions comprising one or more fluidic reservoirs described herein. In certain embodiments, after one or more lysing operations, lysed genomic material (e.g., select eukaryotic genomic material, microbial genomic material) may be isolated and/or separated from the fluid. In some cases, the genomic material is isolated by binding with a support substrate and separating the support substrate and genomic material from the fluid. Referring again to FIG. 3, in an exemplary embodiment, after the first lysing operation is performed, the fluid (e.g., containing the lysed material) is flowed to a first isolation region comprising fluidic reservoir 140 for conducting a first isolation operation (e.g., to remove/deplete select eukaryote genomic material from the fluid). In some such embodiments, the fluid (e.g., substantially depleted of select eukaryote genomic material) may then be transported to fluidic reservoir 130 for a second lysis operation. After the second lysing operation is performed, the fluid may be flowed to a second isolation region comprising fluidic reservoir 150 for conducting a second isolation operation (e.g., to remove/deplete select eukaryote genomic material from the fluid, to isolate microbial genomic material from the fluid). Those skilled in the art would understand, based upon the teachings of this specification, that two or more, three or more, four or more, or five or more lysing operations may be performed (e.g., in two or more fluidic reservoirs) prior to an isolation operation.

A support substrate may be added to, or contained within, one or more fluidic reservoirs (e.g., within one or more isolation regions) for performing an isolation operation. In certain embodiments, the genomic material (e.g., lysed genomic material) binds to at least a portion of a support substrate. The genomic material may attach or bind to a support substrate in any suitable manner. In some cases, a single type of genomic material attaches or binds to a single support substrate. In some embodiments, more than one type of genomic material may attach or bind to a single support substrate. In certain embodiments, the genomic material may attach or bind with the support substrate via formation of a non-specific bond (e.g., non-specific adsorption). In some cases, the genomic material may interact with a functional group present on the surface of the support substrate. For example, the genomic material may bind with the support substrate and/or a functional group present on the surface of the support substrate via a bond such as an ionic bond, a covalent bond (e.g., carbon-carbon, carbon-oxygen, oxygen-silicon, sulfur-sulfur, phosphorus-nitrogen, carbon-nitrogen, metal-oxygen, or other covalent bonds), a hydrogen bond (e.g., between hydroxyl, amine, carboxyl, thiol, and/or similar functional groups), a dative bond (e.g., complexation or chelation between metal ions and monodentate or multidentate ligands), and/or by Van der Waals interactions. In some embodiments, the support substrate comprises an anion exchanger (e.g., an anion exchanger resin) bound to the support substrate.

In some embodiments, at least one anion exchanger bound to the support substrate, is contacted and/or incubated with the fluid (e.g., the lysed fluid). In some embodiments, after contacting and/or incubation with the fluid, the anion exchanger is removed from the fluid. In another embodiment, after contacting and/or incubation with the fluid, the anion exchanger is immobilized and the fluid is removed.

In some embodiments, the support substrate comprises a bead, particle, or magnetic microparticle. Genomic material may be isolated from a fluid by, for example, applying a magnetic field to a fluidic reservoir containing the genomic material bound to the support substrate, such that the support substrate is attracted to the magnetic field source, and the fluid can be removed (e.g., flowed) out of the fluidic reservoir. The removed fluid can be flowed to, for example, a waste fluidic reservoir.

The support substrate may comprise any suitable magnetic (or magnetizable) material. In certain embodiments, the magnetic material comprises a ferromagnetic material. Non-limiting examples of suitable magnetic materials include iron, nickel, cobalt, and alloys thereof and combinations thereof. Additional non-limiting examples of suitable support substrates include a particle, a bead, a surface, or a sphere. In some embodiments, the support substrate is magnetic, e.g., a magnetic particle or bead. In some embodiments, an anion exchange resin is conjugated to the support substrate.

In some embodiments, contacting and/or incubating the fluid with the anion exchanger extracts and/or depletes select eukaryote DNA and/or RNA from the fluid. In some embodiments, contacting and/or incubating the fluid with the anion exchanger extracts/isolates microbial genomic material (e.g., gDNA). In some embodiments, the select eukaryote DNA (and/or RNA) binds to the anion exchanger. In some embodiments, the select m DNA (and/or RNA) binds to the anion exchanger. In certain embodiments, the microbial genomic material binds to the anion exchanger. In some embodiments, the anion exchanger extracts between about 5% to 100%, between about 10% to 99%, between about 15% to 85%, between about 20% to 80%, between about 25% to 75%, between about 30% to 70%, between about 35% to 65%, between about 40% to 60%, or between about 45% to 55% of the genomic material from the fluid. In some embodiments, the anion exchange resin extracts over 95% of the genomic material from the fluid.

In certain embodiments, during and/or after the isolation operation, the isolated genomic material may be eluted. For example, in some embodiments, competition of the isolation process is facilitated by eluting or removing the genomic material off of the anion-exchanger and/or support substrates. In some embodiments, the elution of the genomic material comprises adding an elution buffer (e.g., stored within a fluidic reservoir in fluidic communication with the fluidic hub, and transported to the isolation region). In certain embodiments, during and/or after the isolation operation, the isolated genomic material bound to the anion exchanger may be washed prior to elution.

In some embodiments, the isolation operation is conducted for a particular time. For example, the fluid comprising lysed components and the support substrates (e.g., support substrates comprising an anion exchanger bound to the support substrate) may be incubated (and/or agitated) for between about 0.1 to 10 minutes, between about 2 to 9 minute, between about 3 to 8 minutes, between about 4 to 7 minutes, or between about 5 to 6 minutes. In some embodiments, the microbial lysis reaction is incubated with the anion exchange resin between about 10 to 30 minutes, between about 12 to 28 minutes, between about 15 to 25 minutes, between about 18 to 23 minutes, or between about 19 to 22 minutes. In some embodiments, the fluid comprising lysed components and the support substrates (e.g., support substrates comprising an anion exchanger bound to the support substrate) may be incubated (and/or agitated) for less than 1 minute.

In some embodiments, the fluidic device comprises an amplification region. In certain embodiments, the amplification region is in fluidic communication with at least one reaction region. In some cases, the amplification region may be in fluidic communication with one or more additional regions comprising one or more fluidic reservoirs described herein. In some embodiments, the amplification region is in fluidic communication with the fluidic hub. In certain embodiments, after one or more lysing and/or isolation operations, microbial genomic material may be amplified. Referring again to FIG. 3, in an exemplary embodiment, fluidic device 104 may comprise an amplification region comprising fluidic reservoir 170. In some such embodiments, fluidic reservoir 170 may comprise one or more reagents for amplification of genomic material. In certain embodiments, one or more reagents (e.g., stored in one or more additional fluidic reservoirs) may be flowed to fluidic reservoir 170 to perform the amplification operation. In some embodiments, the genomic material amplified is RNA or DNA. In some embodiments, the DNA is single stranded DNA (ssDNA) and/or double stranded DNA (dDNA). In some embodiments, the DNA is ribosomal DNA (rDNA).

In certain embodiments, the amplification operation comprises isothermal amplification and/or thermal-cycling amplification processes. In an exemplary embodiment, the amplification operation comprises polymerase chain reaction (PCR). PCR in known in the art and generally comprises thermal-cycling based enzymatic amplification of genomic material (e.g., with a primer).

In some embodiments, the amplicon generated during the amplification operation may be diluted. In certain embodiments, an invasion buffer may be added to the fluid comprising the amplicon generated during the amplification operation. For example, in certain embodiments, referring again to FIG. 3, fluidic reservoir 170 may comprise the product of an amplification operation and an invasion buffer (e.g., an invasion buffer stored in one or more additional fluidic reservoirs) may be flowed into fluidic reservoir 170. Invasion buffers are described in more detail, below.

In some embodiments, the fluidic device comprises one or more reaction regions (e.g., comprising one or more fluidic reservoirs). In certain embodiments, one or more reaction regions are in fluidic communication with one or more isolation regions. In some cases, one or more lysis regions may be in fluidic communication with one or more additional regions comprising one or more fluidic reservoirs described herein. In some embodiments, one or more reaction regions may be in fluidic communication with the fluidic hub. In some embodiments, the reaction region comprises a washing operation. Referring again to FIG. 3, in an exemplary embodiment, fluidic reservoir 160 may comprise a washing region for conducting a washing operation. In some embodiments, the washing region comprises one or more wash buffers. The wash buffers may be stored and sealed in the fluidic reservoir, e.g., prior to use of the fluidic device by the user and/or prior to insertion of a sample into the device. In some cases, the fluid (e.g., the sample) may be flowed to the washing region and one or more wash buffers may be added to the washing region (e.g., a wash buffer(s) flowed from one or more additional fluidic reservoirs storing the wash buffer(s)). In certain embodiments, a fluidic reservoir comprises of an isolation region and a washing region. That is to say, in some embodiments, a fluid (e.g., a sample) may be present in a fluidic reservoir in which a particular operation has been performed (e.g., lysing, isolation) and a wash buffer may be added to the fluidic reservoir (e.g., a wash buffer(s) flowed from one or more additional fluidic reservoirs) to wash any unbound components and/or waste reagents.

In some embodiments, after binding the microbial genomic material to the anion-exchanger bound to the support substrate, the support substrates are washed using a wash buffer. In some such embodiments, and prior to the washing operation, the anion exchanger bound to microbial genomic material is immobilized such that and unbound material can be removed without the substantial loss of microbial genomic material.

In certain embodiments, the methods comprise one or more, two or more, three or more, or four or more washing operations (e.g., two or more washing operations between a lysing operation and an isolation operation).

In some embodiments, one or more reaction regions comprises neutralization (e.g., with a base or an acid) of the fluid. For example, in some embodiments, an acid may be added to the fluid in one or more fluidic reservoirs to alter the pH of the fluid. Acids and basis may be stored in one or more reservoirs as described herein.

In certain embodiments, one or more reaction regions comprises or contains stored duplex DNA Invading Artificial Nucleic Acids (DIANAs) (e.g., for detection of one or more microbial pathogens.) In some embodiments, one or more fluids (and optionally one or more additional components) contained within a fluidic reservoir may be mixed (e.g., a fluid and an additional component, a fluid and an analyte, a first fluid and a second fluid). In certain embodiments, mixing comprises agitation such as mechanical agitation (e.g., ultrasonic agitation).

In some embodiments, the devices and methods described herein may facilitate the mixing of two or more fluids (e.g., a sample and a reagent) without the use of a mixing component (e.g., propeller, etc.).

In some embodiments, the mixing of one or more fluids, and optionally one or more additional components (e.g., the mixing of two or more fluids, the mixing of one fluid and an additional component, etc.) may be conducted by flowing the one or more fluids into a first fluidic reservoir, flowing the one or more fluids into a second fluidic reservoir, and then flowing the one or more fluids back into the first fluidic reservoir. Optionally, the one or more fluids may flowed back and forth several times between the first and second fluidic reservoirs. The shuttling/transfer of one or more fluids (e.g., two or more fluids) between two (or more) fluidic reservoirs may facilitate the mixing of the fluids (and/or components) being transferred as described in more detail below. In some embodiments, the one or more additional components comprise a support substrate(s). In some such embodiments, the support substrate(s) may be resuspended in the fluid by mixing as described herein.

Figure 12A:
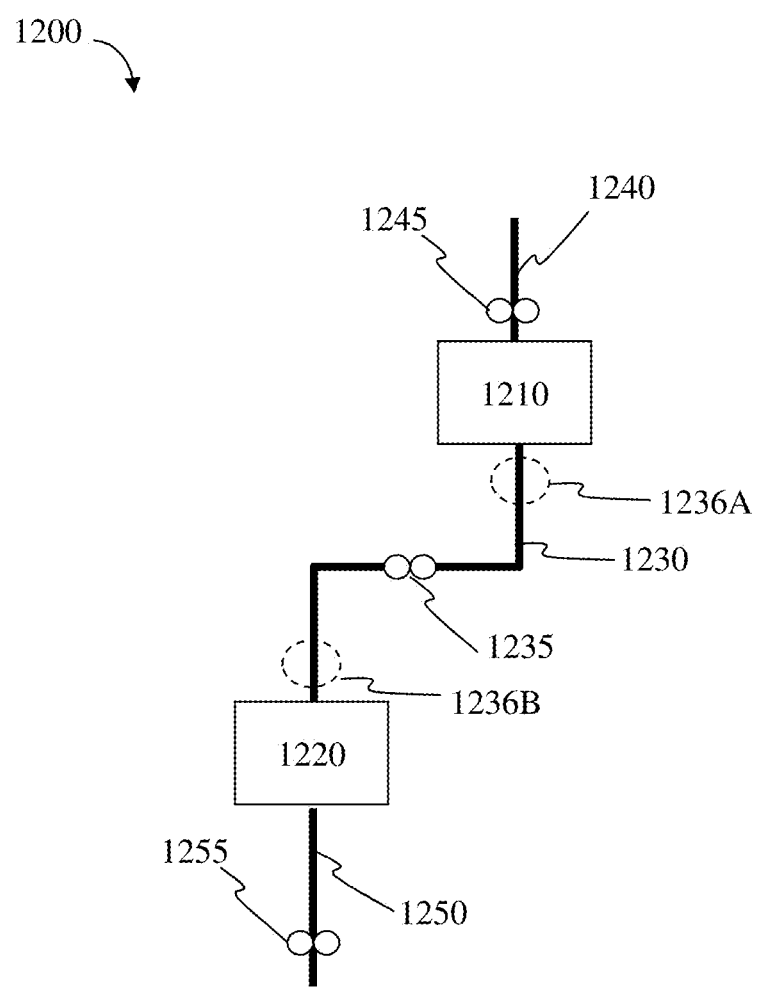
FIG. 12A is a schematic illustration of a portion of a fluidic device that can be used for mixing, according to one set of embodiments.

Referring now to FIG. 12A, in some embodiments, a portion of a device 1200 comprises a fluidic reservoir 1210 (e.g., a first fluidic reservoir) and a fluidic reservoir 1220 (e.g., a second fluidic reservoir), with a connecting channel 1230 (e.g., a fluidic channel as described herein) positioned between and/or in fluidic communication with fluidic reservoir 1210 and fluidic reservoir 1220. In some embodiments, a channel 1240 (e.g., an inlet channel, an outlet channel) is in fluidic communication with fluidic reservoir 1210. In some embodiments, a channel 1250 (e.g., an outlet channel, an inlet channel) is in fluidic communication with fluidic reservoir 1220. In some cases, a valve 1245 may be associated with channel 1240. In certain embodiments, a valve 1255 may be associated with channel 1250.

In some embodiments, at least a portion of the connecting channel has a cross-sectional dimension (e.g., width, height) that is smaller than a cross-sectional dimension of the first fluidic reservoir and a cross-sectional dimension (e.g., width, height) of the second fluidic reservoir (i.e., the first fluidic reservoir and the second fluidic reservoir between which the connecting channel is positioned and/or in fluidic communication with). Additionally or alternatively, in some embodiments, at least a portion of the connecting channel has a cross-sectional area that is smaller than a cross-sectional area of the first fluidic reservoir and a cross-sectional area of the second fluidic reservoir. In some embodiments, the connecting channel has a cross-sectional dimension (e.g., width, height) (or a cross-sectional area), that is less than or equal to 50%, less than or equal to 45%, less than or equal to 40%, less than or equal to 35%, less than or equal to 30%, less than or equal to 25%, less than or equal to 20%, less than or equal to 15%, less than or equal to 10%, less than or equal to 8%, less than or equal to 6%, less than or equal to 4%, or less than or equal to 2% of a cross-sectional dimension (or a cross-sectional area) of the first fluidic reservoir and/or a cross-sectional dimension (or a cross-sectional area) of the second fluidic reservoir. In certain embodiments, the connecting channel has a cross-sectional dimension (or a cross-sectional area) that is greater than or equal to 1%, greater than or equal to 2%, greater than or equal to 4%, greater than or equal to 6%, greater than or equal to 8%, greater than or equal to 10%, greater than or equal to 15%, greater than or equal to 20%, greater than or equal to 25%, greater than or equal to 30%, greater than or equal to 35%, greater than or equal to 40%, or greater than or equal to 45% of a cross-sectional dimension (or a cross-sectional area) of the first fluidic reservoir and/or a cross-sectional dimension (or a cross-sectional area) of the second fluidic reservoir. Combinations of the above-referenced ranges are also possible (e.g., less than or equal to 50% and greater than or equal to 1%). Other ranges are also possible.

It should be appreciated that each of the ranges above may be applied independently for comparison of the connecting channel to the first fluidic reservoir, and comparison of the connecting channel to the second fluidic reservoir. For instance, in some embodiments, the connecting channel has a cross-sectional dimension (e.g., width, height) (or a cross-sectional area) between 1% and 10% of that of the first fluidic reservoir, and between 1% and 25% of that of the second fluidic reservoir.

In certain embodiments, the connecting channel may have a particular length. For example, in some embodiments, the connecting channel has a length of greater than or equal to 250 microns, greater than or equal to 500 microns, greater than or equal to 750 microns, greater than or equal to 1 mm, greater than or equal to 2.5 mm, greater than or equal to 5 mm, greater than or equal to 7.5 mm, greater than or equal to 10 mm, greater than or equal to 25 mm, greater than or equal to 50 mm, greater than or equal to 75 mm, greater than or equal to 100 mm, greater than or equal to 250 mm, greater than or equal to 500 mm, greater than or equal to 750 mm, greater than or equal to 1 cm, greater than or equal to 2.5 cm, greater than or equal to 5 cm, or greater than or equal to 7.5 cm. In certain embodiments, the connecting channel has a length of less than or equal to 10 cm, less than or equal to 7.5 cm, less than or equal to 5 cm, less than or equal to 2.5 cm, less than or equal to 1 cm, less than or equal to 750 mm, less than or equal to 500 mm, less than or equal to 250 mm, less than or equal to 100 mm, less than or equal to 75 mm, less than or equal to 50 mm, less than or equal to 25 mm, less than or equal to 10 mm, less than or equal to 7.5 mm, less than or equal to 5 mm, less than or equal to 2.5 mm, less than or equal to 1 mm, less than or equal to 750 microns, or less than or equal to 500 microns.

Referring again to FIG. 12A, in some cases, one or more valves 1235 may be associated with connecting channel 1230. As shown illustratively in FIG. 12A, valve 1235 may be positioned between fluidic reservoirs 1210 and 1220. The valve may be located at any suitable position along the connecting channel. In some embodiments, the valve is located at a position 1236A adjacent the first fluidic reservoir (e.g., at an inlet or an outlet of the first fluidic reservoir). In other embodiments, the valve is located at a position 1236B adjacent the second fluidic reservoir (e.g., at an inlet or an outlet of the second fluidic reservoir). Other configurations are also possible.

In some embodiments, two or more valves may be associated with connecting channel 1230. For example, a valve may be positioned at both positions 1236A (adjacent the first fluidic reservoir) and 1236B (adjacent the second fluidic reservoir).

Figure 12B:
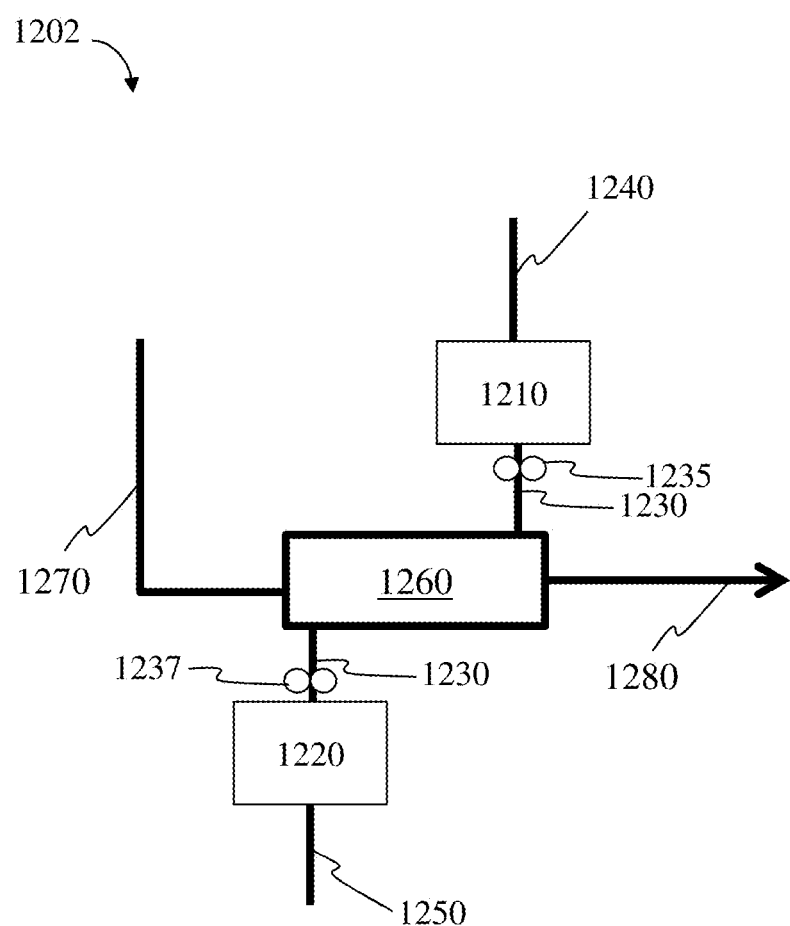
FIG. 12B is a schematic illustration of a portion of a fluidic device that can be used for mixing, according to one set of embodiments.

In some embodiments, a fluidic hub may be in fluidic communication with the connecting channel. For example, as illustrated in FIG. 12B, a portion of a device 1202 comprises fluidic hub 1260 in fluidic communication with connecting channel 1230. In some such embodiments, valve 1235 and valve 1237 may be associated with connecting channel 1230 (e.g., to facilitate flow between fluidic reservoir 1210, fluidic reservoir 1220, and/or fluidic hub 1260). However, in some such embodiments, valves 1235 and 1237 need not be present.

In some embodiments, one or more connecting channels (e.g., each connecting channel positioned between two fluidic reservoirs) may be used. For example, in some embodiments, mixing may be conducted between two or more pairs of fluidic reservoirs (e.g., comprising four or more, six or more, eight or more, ten or more, or twelve or more fluidic reservoirs), each pair associated with a connecting channel. In some embodiments, a fluidic hub may be associated with and in fluidic communication with the one or more connecting channels.

Two or more fluidic reservoirs (e.g., as illustrated in FIGS. 12A-12B) may be useful for facilitating the mixing of fluids and/or components. In an exemplary embodiment, a fluid (e.g., a first fluid) may be flowed, in a first direction, from a first fluidic reservoir (e.g., fluidic reservoir 1210 of FIG. 12A or FIG. 12B) to a second fluidic reservoir (e.g., fluidic reservoir 1220) via a connecting channel (e.g., connecting channel 1230). The fluid may then be flowed, in a second direction (different than the first direction), from the second fluidic reservoir to the first fluidic reservoir via the connecting channel. This process may cause mixing within at least portions of the fluid. In some instances the second direction is a direction opposite the first direction. In some embodiments, the fluid comprises two or more types of fluids such that, upon mixing, the two or more fluids are mixed together. In certain embodiments, the fluid comprises a first fluid and one or more additional components (e.g., a support substrate(s)), such that the first fluid and the additional components mix together. For example, a support substrate(s) may be resuspended and/or mixed within a first fluid by mixing as described herein. In some embodiments, a similar process can be used for washing support substrates (e.g., magnetic beads) in a reaction mixture (e.g., instead of, or in addition to, mixing).

In some embodiments, the mixing may be facilitated by choosing differences in cross-sectional dimensions (e.g., width, height) or cross-sectional areas between the first fluidic reservoir and the connecting channel, and the second fluidic reservoir and the connecting channel, as described herein. For example, the method described above may take place in a device including a connecting channel, at least a portion of which has a smaller cross-sectional area (e.g., less than or equal to 50%, less than or equal to 25%, or other ranges described herein) than a cross-sectional area of the first fluidic reservoir and a cross-sectional dimension of the second fluidic reservoir.

In some embodiments, a second fluid (e.g., a gas) may be utilized to facilitate the transfer of the first fluid (e.g., by pushing the first fluid) between two locations with a device. For example, in some embodiments, a second fluid (e.g., a first gas) may be introduced (e.g., via channel 1240 in FIG. 12A) into the first fluidic reservoir. A pressure (e.g., a positive pressure) may be applied to the second fluid such that the second fluid pushes the first fluid from the first fluidic reservoir through the connecting channel, and into the second fluidic reservoir (e.g., in a first direction). A third fluid (e.g., a second gas) may then be introduced (e.g., via channel 1250 in FIG. 12A) into the second fluidic reservoir. A pressure may then be applied to the third fluid such that the third fluid pushes the first fluid from the second fluidic reservoir, through the connecting channel, and into the first fluidic reservoir (e.g., in a second direction different/opposite the first direction).

The introduction and/or flow of one or more fluids between fluidic reservoirs may be facilitated by the opening and/or closing of one or more valves (or flow-gates). For example, referring again to FIG. 12A, in some embodiments, a fluid (e.g., a liquid) may be introduced into first fluidic reservoir 1210. In some such embodiments, valve 1235 may be closed and a cover (e.g., a semipermeable membrane) is associated with first fluidic reservoir 1210 such that, upon application of pressure to the fluid, any gas present within the first fluidic reservoir passes through the semipermeable membrane but the fluid (liquid) is retained within the first fluidic reservoir. Valve 1235 may then be opened and pressure applied to the fluid (e.g., via a second fluid such as a gas) such that the fluid flows to second fluidic reservoir 1220 via connecting channel 1230. In some such embodiments, valve 1255 may be closed. In some embodiments, a cover (e.g., a semipermeable membrane) may be associated with second fluidic reservoir 1220 such that any gas present within the second fluidic reservoir is passed through the cover but the fluid is retained within the second fluidic reservoir. In some embodiments, the cover over the first fluidic reservoir is the same cover over the second fluidic reservoir. In some cases, valve 1245 may then be closed and valve 1255 opened, and a pressure applied to the fluid such that the fluid is transferred, via connecting channel 1230, from second fluidic reservoir 1220 to first fluidic reservoir 1210, and any gas (e.g., a second fluid) present in first fluidic reservoir 1210 and/or second fluidic reservoir 1220 passes through the cover associated with first fluidic reservoir 1210. Performing such steps may be useful for the mixing of fluids without introducing bubbles (or reducing the amount of bubbles) into the channels and/or for mixing a particular amount of (metered) fluid (e.g., a volume of fluid substantially equal to the volume of the fluidic reservoir(s)).

In some cases, mixing may be performed by flowing a stream of gas (e.g., a sterilized gas) into a fluidic reservoir before, during, and/or after a particular operation. The stream of gas may be flowed for any suitable time (e.g., at least 1 s, 3 s, 5 s, 7 s, 10 s, 15 s, 20 s, 30 s, 45 s, 60 s; and/or less than 120 s, 60 s). In some such embodiments, the stream of gas need not be continuous, but can be pulsed. In some such embodiments, the stream of gas may cause mixing and/or homogenization of the one or more fluids and/or reagents within a fluidic reservoir. The gas may be flowed from, for example, the fluidic hub into the fluidic reservoir and, from the fluidic reservoir, to the gas chamber in fluidic communication with the fluidic reservoir. The flow of gas through the fluidic reservoir containing one or more fluids (and one or more reagents) and into the gas chamber may cause the one or more fluids and the one or more reagents to mix. In some embodiments, the flow of gas through the fluid contained within the fluidic reservoir results in turbulent flow within the fluid. Without wishing to be bound by theory, turbulent flow may result in mixing of the fluid(s) and/or reagent(s) within the fluidic reservoir. In some embodiments, a similar process can be used for washing support substrates (e.g., magnetic beads) in a reaction mixture.

Referring again to FIG. 2, a fluid may be introduced into fluidic reservoir 120. In some embodiments, a gas may be flowed from fluidic hub 110 into fluidic reservoir 120 (via valve 122 and branching channel 125) such that the gas flows into the fluidic reservoir through the fluid. In some such embodiments, the gas (but not the fluid) may flow into fluidic conduit 195 in fluidic communication gas chamber 190. In some embodiments, the gas chamber may be open to atmosphere and the gas vents to atmosphere.

In certain embodiments, the first fluid and/or reagents are substantially inhibited from flowing into the gas chamber. For example, in some embodiments, a valve (or flow-gate) positioned between the fluidic reservoir and the gas chamber may inhibit one or more fluids and/or reagents from flowing into the gas chamber, while selectively permitting the gas to flow into the gas chamber.

In certain embodiments, the fluidic reservoirs are constructed, arranged, and operated in order to perform a set of particular operations. In an exemplary embodiment, the set of operations includes selective depletion of select eukaryote DNA from a sample (e.g., via lysing of select eukaryote cells and/or isolating extracting their genomic material), lysing of one or more microbial cells in the same, isolation of microbial genomic material (e.g, DNA and/or RNA), amplification of the microbial genomic material, reaction with duplex DNA Invading Artificial Nucleic Acids (DIANAs), and detection of one or more microbial pathogen. In some such embodiments, one or more additional washing, isolation, reaction, mixing, or other operations may also be conducted.

Figure 5:
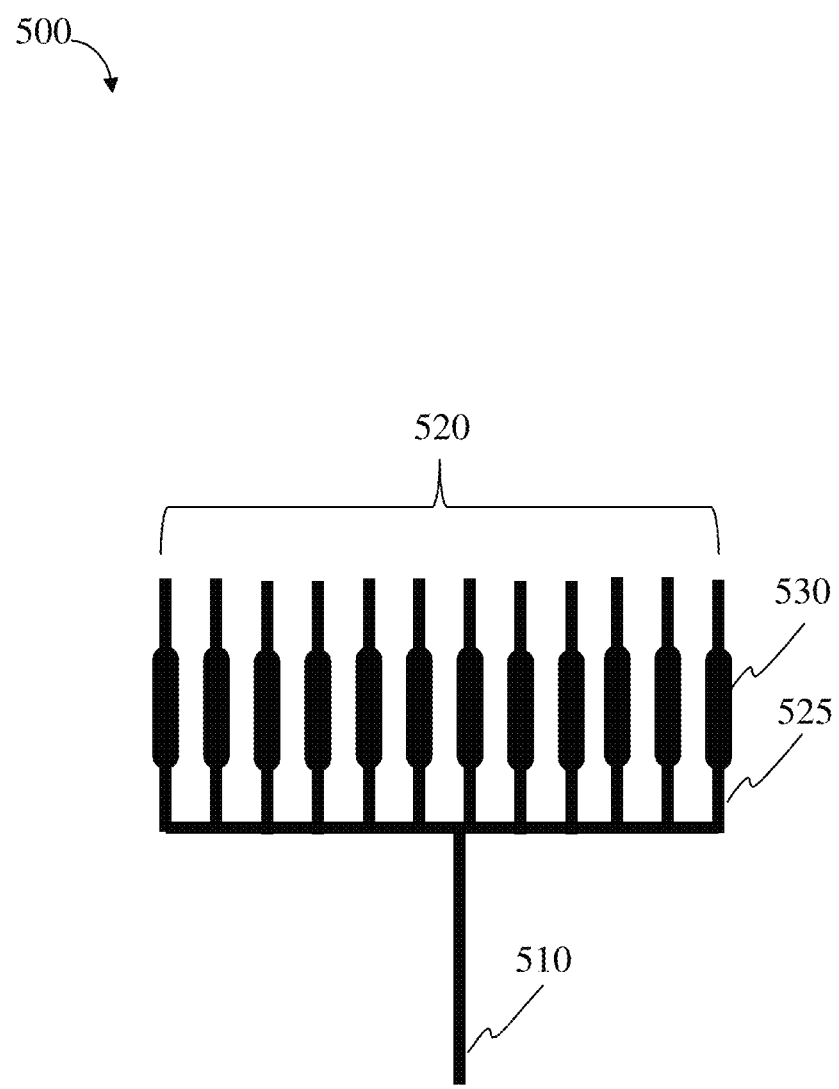
FIG. 5 is a schematic illustration of a fluidic device, according to one set of embodiments.

In some embodiments, after one or more operations described above, the fluid (e.g., the fluid including the amplicon(s) and/or an invasion buffer) may be divided into one or more processing chambers for metering, (e.g., in metering channels) DIANA binding/invasion, and/or detection (e.g., a detection region). In some embodiments, one or more processing chambers are each in fluidic communication with at least one reaction region and/or the amplification region. In some cases, one or more processing chambers may be in fluidic communication with one or more additional regions comprising one or more fluidic reservoirs described herein. In some embodiments, one or more processing chambers may be in fluidic communication with the fluidic hub. In some embodiments, the fluidic device comprises two or more, three or more, four or more, six or more, eight or more, ten or more, twelve or more, fourteen or more, or sixteen or more processing chambers. For example, as illustrated in FIG. 5, fluidic device 500 comprises fluidic channel 510 in fluidic communication with plurality of processing chambers 520 each comprising a metering channel 525. In certain embodiments, each metering channel as the same length, volume, length-to-width ratio, and or cross-sectional dimension as one another. In some cases, the use of metering channels divides a fluid flowing into each metering channel substantially equally. Advantageously, the use of metering channels may produce two or more volumes of fluid that are substantially equal (e.g., such that detection of one or more pathogens contained within the fluid are conducted at equal volumes and substantially simultaneously).

In certain embodiments, the processing chamber comprises a detection region. For example, referring again to FIG. 5, each processing chamber comprises detection region 530 in fluidic communication with metering channel 525. In some embodiments, each detection region may be in fluidic communication with one or more additional regions comprising one or more fluidic reservoirs described herein. In certain embodiments, each detection region is in fluidic communication with each processing chamber. In some cases, one or more detection regions may be in fluidic communication with the fluidic hub. In some embodiments, one or more probes targeting desired pathogens are contained within each detection region. In some such embodiments, the presence of one or more microbial pathogens may be detected by the binding of one or more probes with the pathogen and generating a signal. In some embodiments, the signal is detectable through optical, chemical, electrical, or mechanical detection methods.

In some embodiments, after an amplification operation, the amplicon which were developed/created during enzymatic amplification may be detected and/or identified (e.g., within a metering channel).

In some embodiments, DNA Invading Artificial Nucleic Acids (DIANAs) may be used detect and identify microbial genomic materials. For example, in some embodiments, DIANAs may be added to a fluidic reservoir containing the amplicons produced during the amplification operation. In certain embodiments, one or more DIANAs may be present in the detection region of one or more metering channels.

In some embodiments, the DIANA probes comprise the reverse complementary sequences of any one of SEQ ID NOS: 1-37, described herein. In some embodiments, the DIANA probes comprise a sequence with greater than 85% identity with any one of SEQ ID NOS: 1-37 or their reverse complementary counterparts.

In some embodiments, the DIANAs take the form of a specialized type or class of Peptide Nucleic Acids (PNAs).

In some embodiments, the DIANAs take the form of a specialized type or class of Locked or Bridged Nucleic Acids (LNAs and/or BNAs). In some embodiments, DIANAs that locally invades duplex DNA may be used in devices and methods disclosed herein.

In some embodiments, PNA oligomer based DIANAs having a chiral stereo-center at the gamma-position of the backbone (also known as γPNA). Without wishing to be bound by theory, a PNA oligomer that is pre-oriented structurally into a right-handed helix may be energetically favored to perform duplex DNA invasion, in some embodiments. In some embodiments, the microbial DNA is detected using γPNA as taught in WO 2013/176992, the contents of which are incorporated by reference in its entirety. In some embodiments, the microbial DNA is detected using γPNA as described in He et al., J. Am. Chem. Soc. 2009, 131, 12088-12090.

In some embodiments, the target genomic region of interest for detection in the amplified genomic material includes, but is not limited to, bacterial 16S, ITS, 23S, RPL gene, or TUF gene. In some embodiments, the target genomic region of interest for detection in the amplified genomic material includes, but is not limited to, fungal 18S, ITS, 5.8S, and 25/28S. In certain embodiments, the target genomic region of interest for detection in the amplified genomic material includes antibiotic resistance markers and/or genes, and/or plasmids. In some embodiments, each DIANA targets a specific microbial genomic material (e.g., DNA or RNA) from a single microbial species. In some embodiments, each DIANA targets a specific microbial genomic material (e.g., DNA or RNA) a group of microbes. In some embodiments, the specific microbial genomic material (e.g., DNA or RNA) is amplified microbial genomic material.

In some embodiments, one or more detectable markers are bound to the DIANAs. In some embodiments, the one or more detectable markers bound on the DNA amplicon. In some embodiments, one or more detectable markers are positioned on an oligomer, which is universal to some or all potential targets.

In some embodiments, detection of the binding of DIANAs to their respective target is through optical, chemical, electrical, or mechanical detection methods. In some embodiments, optical detection is through the use of fluorescence or luminesce.

A fluidic device, or portions thereof (e.g., a substrate, a fluidic channel, a fluidic reservoir, a gas chamber), can be fabricated of any material suitable for forming a channel or other component. Non-limiting examples of materials include polymers (e.g., polypropylene, polyethylene, polystyrene, poly(styrene-co-acrylonitrile), poly(styrene-co-butadiene), poly(acrylonitrile, butadiene, styrene), poly(styrene-co-maleic anhydride), poly(styrene-co-acrylate), poly (styrene-co-methyl methacrylate), poly(methyl methacrylate), polycarbonate, poly(dimethylsiloxane), PVC, PTFE, PET, cyclo-olefin copolymer, polyimide, cyclo-olefin polymers or co-polymers, or blends of two or more such polymers, or metals including nickel, copper, stainless steel, bulk metallic glass, or other metals or alloys, or ceramics including glass, quartz, silica, alumina, zirconia, tungsten carbide, silicon carbide, or non-metallic materials such as graphite, silicon, or others.

Figure 6A:
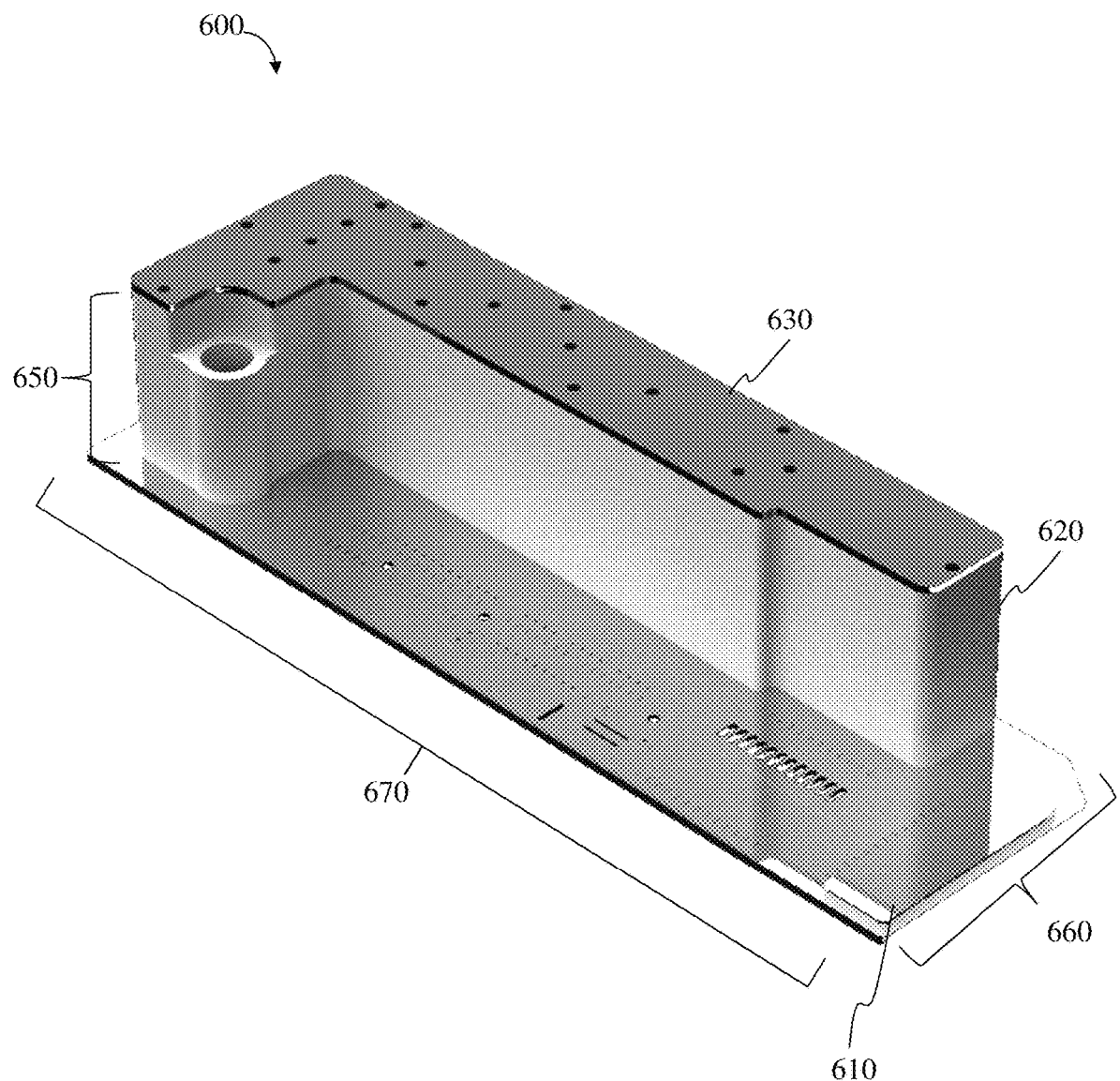
FIG. 6A is a schematic illustration of an exemplary fluidic device, according to one set of embodiments.

An exemplary perspective view of a fluidic device is shown in FIG. 6A. In some embodiments, fluidic device 600 comprises a first region 610 comprising a plurality of fluidic channels and a second region 620 comprising a plurality of fluidic reservoirs. In some cases, the fluidic device comprises cover 630 comprises a plurality of fluidic conduits (e.g., fluidic conduits positioned between one or more gas chambers and one or more fluidic reservoirs).

Figure 6B:
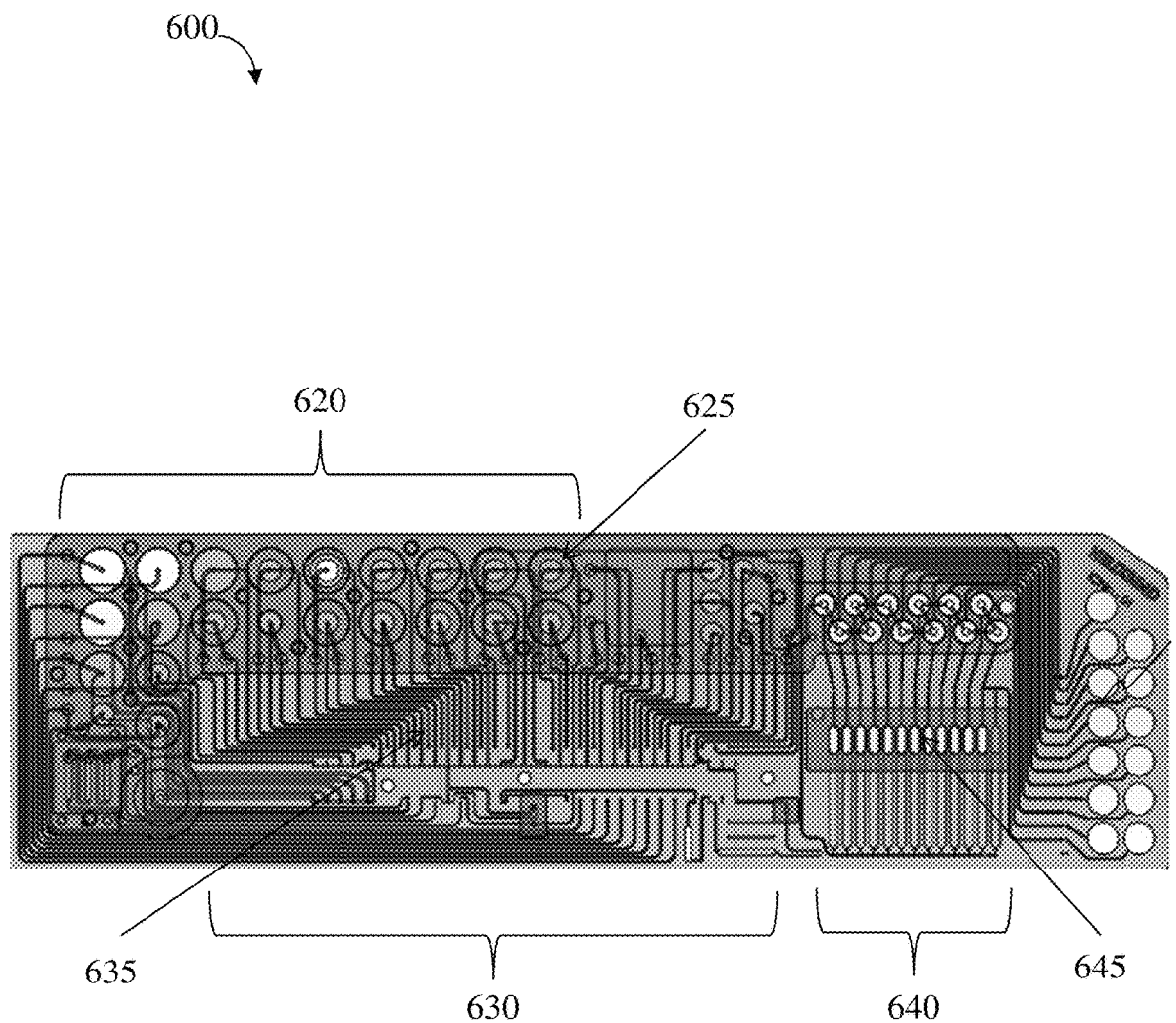
FIG. 6B is a schematic illustration of an exemplary fluidic device, according to one set of embodiments.

FIG. 6B is a top-down view of fluidic device 600. In some embodiments, second region 620 comprises one or more fluidic reservoirs including, for example, exemplary fluidic reservoir 625. In certain embodiments, first region 610 comprises a plurality of fluidic channels including, for example, exemplary fluidic channels 635. As illustrated in FIG. 6B, the fluidic device further comprises a plurality of metering channels 640 (each metering channel comprising detection region 645).

In some embodiments, first region 610 comprising the plurality of fluidic channels further comprises a thin-film (e.g., a thin film polymer) attached to the bottom of the fluidic device (e.g., to enclose the fluidic channels). In some cases, the thin-film attached to the bottom of the device has relatively high optical transparency (e.g., to facilitate efficient detection of any optical signal emitted from one or more detection regions).

In some embodiments, the fluidic device has an overall width, an overall height, and an overall length. For example, referring again to FIG. 6B, fluidic device 600 has an overall height 650, and overall width 660, and an overall length 670.

In certain embodiments, the fluidic device has a ratio of overall height to overall width of at least 1:1, at least 2:1, at least 3:1, at least 5:1, or at least 10:1. In some embodiments, the fluidic device has a ratio of overall height to overall length of at least 1:1, at least 2:1, at least 3:1, at least 5:1, or at least 10:1.

In certain embodiments, the fluidic device has a particular overall width. In some embodiments, the fluidic device has a width of about 2-5 inches, about 2.5-5 inches, 3-6 inches.

In certain embodiments, the fluidic device has a particular overall length. In some embodiments, the fluidic device has a length of about 5-12 inches, about 6-16 inches, or 8-20 inches.

In some embodiments, the fluidic device occupies a particular surface area. In some embodiments, the fluidic device occupies a surface area of about 10-63 inches squared, about 17-85 inches squared, about 23-115 inches squares, or about 28-120 inches squared. The surface area as described herein is measured on the largest cross-section of the fluidic device parallel to the plurality of fluidic channels (and perpendicular to at least one fluidic reservoir).

In some embodiments, the fluidic device includes an opening for adding the sample, e.g., injecting the sample into the sample inlet reservoir. In some embodiments, the opening has a re-sealable cover. In some embodiments, opening the cover requires mechanical force, wherein without mechanical force the cover remains closed. In some embodiments, the opening is covered with a membrane through which the sample is inserted.

In some embodiments, the fluid sample or specimen is flowed to the fluidic device via a receptacle in the fluidic device constructed and arranged to receive and extract a fluid samples from a vacuette or similar specimen tube or vial.

In some embodiments, the fluidic device comprises a receptacle constructed and arranged to receive a Monovette. By applying force/pressure on the plunger of the Monovette, the fluid specimen from the Monovette is flowed to the fluidic device via the receptacle. In some embodiments, the fluidic device comprises a receptacle constructed and arranged to receive a Vacuette. In some embodiments, the fluidic device comprises a receptacle constructed and arranged to receive any container capable and/or storing and/or transporting a fluid.

In some embodiments, the fluidic device is constructed and arranged to incorporate one or more tubes designed to flow the sample from a specimen vial or receptacle. In some embodiments, such tubes, each and individually, may provide positive pressure, negative pressure, and/or ambient pressure to facilitate the flow of the sample into the device. In some embodiments one or more tubes are designed to work in tandem, and/or in parallel, and or serially, to enable efficient flow of the sample into the device. In some embodiments, only a single tube is required.

In some embodiments, and in cases where more than a single tube may be used to flow the sample from the vial to the fluidic device may be placed in in close proximity, a non-limiting example would be 'side-by-side'. In another non-limiting example, one tube may be placed inside another tube.

In some embodiments, these tubes may serve to puncture the seal of the vial prior to enabling flow of the sample to the fluidic device.

In some embodiments, the sample is flowed from the vial to the fluidic device through pneumatic force, whereas in other cases it might be mechanical or electrical.

In some embodiments, the fluid (e.g., sample) introduced into the fluidic device is a fluid from a source (e.g., a patient, or a laboratory animal, or liquid media, or any organism). In some embodiments, the fluid is a bodily fluid, bodily secretion, or a bodily excretion. In some embodiments, the fluid includes, but is not limited to, stool, sputum, urine, blood, and/or combinations thereof. As described herein, the fluid may be introduced, for example, into the sample inlet reservoir of the fluidic device (e.g., fluidic reservoir 115 in FIG. 1).

In some embodiments, the fluid (e.g., sample) introduced into the fluid device is between about 100 µl to 2.5 ml, about 200 µl to 2 ml, about 300 µl to 1.5 ml, about 400 µl to 1 ml, or about 500 µl to 750 µl. In some embodiments, the sample is between about 0.5 ml to 10 ml, about 1 ml to 9 ml, about 2 ml to 8 ml, about 3 ml to 7 ml, or about 4 ml to 6 ml in volume. Other volumes are also possible.

In some embodiments, the lysing reagent includes one or more detergents or surfactants. In some embodiments, the detergents or surfactants are non-ionic, zwitterionic, or non-detergent sulfobetaines. Detergents and surfactants, include, but are not limited to BigCHAP, Deoxy BigCHAP, Brij 35, Brij 58P, Cymal-1, Cymal-2, Cymal-5, Cymal-6, Decyl-β-maltopyranoside, n-Dodecyl-β-D-maltoside, n-Hexadecyl-β-D-maltoside, Undecyl-β-D-maltoside, Decyl-β-D-1-thiomaltopyranoside, Octyl-β-D-glucopyranoside, Decyl-β-D-1-thioglucopyranoside, Octyl-β-Dthioglucopyranoside, Digitonin, Dimethyldecylphosphine oxide (APO-10), Dodecyldimethylphosphine oxide (APO-12), IGEPAL CO-520, IGEPAL CO-630, and IGEPAL CO-720, N-Octanoyl-N-methylglucamine(MEGA-8), N-nonanoyl-N-methylglucamine(MEGA-9), N-Decanoyl-N-methylglucamine(MEGA-10), nonidet P40-substitute, Pluronic F-68, saponin, thesit, Triton X-100, Triton X-114, TWEEN 20, TWEEN 40, TWEEN 80, ASB-14(amidosulfobetaine-14), ASB-16(amidosulfobetaine-16), C7BzO, CHAPS, CHAPSO, EMPIGEN BB, 3-(N,N-Dimethyloctylammonio) propanesulfonate inner salt (SB3-8), 3-(decyldimethylammonio)-propanesulfonate inner salt (SB3-10), 3-(dodecyldimethylammonio)-propanesulfonate inner salt (SB3-12), 3-(N,N-dimethylmyristylammonio)-propanesulfonate (SB3-14), 3-(N,N-dimethylpalmitylammonio)- propanesulfonate(SB3-16), 3-(N,N-dimethyloctadecylammonio)-propanesulfonate(SB3-18), 3-(1-pyridinio)-1-propanesulfonate (NDSB 201), and 3-(benzyldimethylammonio) propanesulfonate (NDSB 256).

In some embodiments, the lysing reagent (e.g., for select eukaryote cell lysing) has a concentration of surfactants between about 0.27% to 15% v/v, between about 0.39% to 13% v/v, between about 0.45% to 12% (v/v), or between about 0.60% to 10% (v/v) of a Tween surfactant and/or between about 0.22% to 10% (v/v), between about 0.16% to 8.25% (v/v), or between about 0.44% to 6.75% (v/v) of Triton or IGEPAL.

In some embodiments, the lysing reagent (e.g., for select eukaryote cell lysing) comprises a concentration of surfactants between about 0.25% to 1% (v/v), between about 0.35% to 0.85% (v/v), between about 0.45% to 0.75% (v/v), or between about 0.55% to 0.65% (v/v) of a Tween surfactant and/or between about 0.15% to 0.65% (v/v), between about 0.25% to 0.55% (v/v), or between about 0.35% to 0.45% (v/v) of Triton or IGEPAL. In some embodiments, the Tween surfactant is selected from the group consisting of Tween-20, Tween-40, and Tween-80. In some embodiments, the Triton is Triton X-100 or Triton X-114. In some embodiments, the IGEPAL is selected from the group consisting of IGEPAL CO-520, IGEPAL CO-630, and IGEPAL CO-720.

In some embodiments, the lysing reagent comprises at least one anti-foaming agent. Suitable anti-foaming agents include, but are not limited to, Antifoam A, Antifoam 204, Antifoam B, Antifoam C, Antifoam Y-30, Antifoam SE-15, and simethicone-based antifoams. Other anti-foaming agents are also possible.

In certain embodiments, the lysing reagent comprises between about 0.15 M to 0.75 M, about 0.2 M to 0.7 M, about 0.25 M to 0.65 M, about 0.3 M to 0.6 M, about 0.35 M to 0.55 M, or about 0.4 M to 0.5 M or monovalent salts. In some embodiments, the lysing reagent comprises contains less than about 0.15 M of monovalent salts (e.g., for inducing osmotic stress). In some embodiments the concentration of the monovalents salts in the lysing reagent is between about 50 mM and 6 M, about 150 mM and 5 M, about 350 mM and 4.5 M, about 550 mM and 4 M, about 900 mM and 3.75 M, or about 1 M and 3.5 M. In some embodiments, the salt concentration of the monovalent salts in the lysing reagent is between about 50 mM and 800 mM, about 100 mM and 700 mM, about 200 mM and 600 mM, about 300 mM and 500 mM, or about 350 mM and 450 mM.

Non-limiting examples of monovalent salts include, for example, NaCl, KCl, LiCl, and combinations thereof.

In some embodiments, the pH of the lysing reagent is between about 6 to 9. In some embodiments, the pH is at or about neutral pH. In some embodiments, performing the select eukaryote cell or microbial cell lysis reaction at a pH between about 6 to 9 or near neutral is advantageous over current methods known in the art due to an increase in the viability and/or structural integrity of microbial cells in the presence of some surfactants.

In some embodiments, the lysing operation is performed at room temperature. In certain embodiments, the lysing operation is performed at between about 5° C. to 20° C., about 9° C. to 16° C., about 25° C. to 75° C., about 30° C. to 70° C., or about 35° C. to 55° C.

In certain embodiments, the lysing operation is performed for about 0.01-20 minutes, between about 0.1-9.0 minutes, between about 1.0-8.0 minutes, between about 2.0-7.0 minutes, between about 3.0-6.0 minutes, or between about 4.0-5.0 minutes.

In some cases, the lysing operation may be terminated (e.g., lysing may be inhibited) by adding a lysis termination buffer. In some embodiments, the lysis termination buffer comprises at least one electrolyte. In some embodiments, the concentration of the electrolyte added to the lysing reagent is between about 100 mM to 750 mM, about 150 mM to 650 mM, about 200 mM to 550 mM, about 250 mM to 450 mM, or about 300 mM to 400 mM, versus the total lysing reagent concentration. Electrolytes that can be added to the lysis termination buffer include, but are not limited to, monovalent salts and divalent salts. Advantageously, in some embodiments, the termination of the lysing reagent using at least one electrolyte improves downstream processes that use anion-exchange resins (e.g., removal of select eukaryote DNA, isolation of microbial cells, lysis of microbial cells, or isolation of microbial genomic material).

In some embodiments, the lysis termination buffer has a pH below about 9. In some embodiments, the lysis termination buffer has a pH between about 6 to 9. In some embodiments, the lysis termination buffer has a pH at or about neutral pH. In some embodiments, maintaining the lysis termination buffer at a pH between about 6 to 9 or at about neutral improves downstream processing (e.g., removal of select eukaryote DNA, isolation of microbial cells, lysis of microbial cells, or amplification of microbial DNA) of the intact microbial cells.

In certain embodiments, the lysing reagent (e.g., for lysing of microbial cells) comprises an enzyme such as lysozyme, lyticase, zymolyase, mutanolysin, and lysostaphin.

In some embodiments, the lysozyme concentration in the lysing reagent is between about 5 to 200 mg/ml, about 1 to 150 mg/ml, 5 to 175 mg/ml, about 15 to 140 mg/ml, about 20 to 100 mg/ml, about 30 to 95 mg/ml, about 45 to 75 mg/ml, or about 50 to 62 mg/ml. Other ranges are also possible.

In some embodiments, the lysozyme concentration the lysing reagent may be diluted, after performing the lysing operation, to between about 0.01 to 1 mg/ml, about 0.1 to 10 mg/ml, 0.5 to 15 mg/ml, about 1 to 20 mg/ml, about 0.3 to 8 mg/ml, about 0.7 to 7 mg/ml, about 0.2 to 0.9 mg/ml, or about 0.05 to 0.35 mg/ml.

In some embodiments, the lyticase concentration in the lysing reagent is between about 500 to 50,000 U/ml, about 250 to 10,000 U/ml, 425 to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, or about 3,000 to 15,000 U/ml.

In some embodiments, the lyticase concentration in the lysing reagent may be diluted, after performing the lysing operation, between about 1 to 1000 U/ml, about 5 to 200 U/ml, 20 U to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the zymolyase concentration in the lysing reagent is between about 500 to 50,000 U/ml, about 250 to 10,000 U/ml, 425 U to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, or about 3,000 to 15,000 U/ml.

In some embodiments, the zymolyase concentration in the lysing reagent may be diluted, after performing the lysing operation, is between about 1 to 1000 U/ml, about 5 to 200 U/ml, 20 U to 800 U/ml, about 30 to 700 U/ml, about 40 to 600 U/ml, about 50 to 500 U/ml, about 60 to 400 U/ml, about 70 to 300 U/ml, about 80 to 200 U/ml, or about 90 to 100 U/ml.

In some embodiments, the mutanolysin concentration in the lysing reagent is between about 500 to 50,000 U/ml, about 250 to 10,000 U/ml, 425 to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, or about 3,000 to 15,000 U/ml.

In some embodiments, the mutanolysin concentration in the lysing reagent is between about 1 to 1000 U/ml, about 5 to 200 U/ml, 20 to 800 U/ml, about 30 to 700 U/ml, about 40 to 600 U/ml, about 50 to 500 U/ml, about 60 to 400 U/ml, about 70 to 300 U/ml, about 80 to 200 U/ml, or about 90 to 100 U/ml.

In some embodiments, the lysostaphin concentration in the lysing reagent is between about 500 to 50,000 U/ml, about 250 to 10,000 U/ml, 425 U to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, or about 3,000 to 15,000 U/ml.

In some embodiments, the lysostaphin concentration in the lysing reagent is between about 1 to 1000 U/ml, about 5 to 200 U/ml, 20 to 800 U/ml, about 30 to 700 U/ml, about 40 to 600 U/ml, about 50 to 500 U/ml, about 60 to 400 U/ml, about 70 to 300 U/ml, about 80 to 200 U/ml, or about 90 to 100 U/ml In some embodiments, the lysing reagent includes one or more detergents. In some embodiments, the detergent is a zwitterionic detergent. In some embodiments, the zwitterionic detergent is from the sulfobetaine families. Non-limiting example of suitable sulfobetaine detergents include, but are not limited to, N-Decyl-N,N-dimethyl-3-ammonio-1-propanesulfonate, N-Decyl-N,N-dimethyl-3-ammonio-1-propanesulfonate, N-Dodecyl-N,N-dimethyl-3-ammonio-1-propanesulfonate, N-Hexadecyl-N,N-dimethyl-3-ammonio-1-propanesulfonate, N-Octadecyl-N,N-dimethyl-3-ammonio-1-propanesulfonate, and 3-[N,N-Dimethyl(3-myristoylaminopropyl)ammonio]propanesulfonate.

In some embodiments, the detergents are a non-ionic detergent from the glucopyranoside family. Non-limiting examples of suitable non-ionic glucopyranoside detergents include, for example, 3-acetylumbelliferyl b-D-glucopyranoside, N-amyl b-D-glucopyranoside decyl b-D-thioglucopyranoside, n-dodecyl b-D-glucopyranoside, hexadecyl b-D-glucopyranoside, hexyl b-D-glucopyranoside, methyl a-D-glucopyranoside, octyl b-D-glucopyranoside, and phenyl-a-D-glucopyranoside.

In some embodiments, the detergent is a cationic detergent. Non-limiting examples of suitable cationic detergents include, for example, alkyltrimethylammonium bromide, amprolium hydrochloride, benzalkonium chloride, benzyldimethyldodecylammonium chloride, benzyldimethyltetradecylammonium chloride, benzyldodecyldimethylammonium bromide, cetylpyridinium chloride, cetyltrimethylammonium bromide, dimethyldioctadecylammonium bromide, dodecylethyldimethylammonium bromide, dodecyltrimethylammonium bromide, ethylhexadecyldimethylammonium bromide, hexadecylpyridinium bromide, hexadecylpyridinium chloride, hexadecyltrimethylammonium bromide, methylbenzethonium chloride, myristyltrimethylammonium bromide, oxyphenonium bromide, tetraheptylammonium bromide, tetrakis(decyl)ammonium bromide, tetrakis(decyl)ammonium bromide, and tricaprylylmethylammonium chloride. In some embodiments, the concentration of cationic detergents is between about 1-100× critical micelle concentration (CMC) of the cationic detergent.

In some embodiments, the concentration of the detergent is dependent on the critical micelle concentration (CMC) of the specific detergent in the lysing reagent. In some embodiments, each detergent concentration in the lysing reagent is between about 10 to 11,000, about 25 to 12,500, about 50 to 8,000, about 75 to 7,000, about 95 to 8,500, or about 98 to 6,750 times the CMC. In some embodiments, the detergent concentration in the lysing reagent is between about 100 to 5,000, about 125 to 9,000, about 200 to 8,000, about 400 to 7,000, or about 500 to 6,000 times the CMC. In some embodiments, the detergent concentration in the lysing reagent is between about 100 to 1000, about 200 to 900, about 300 to 800, about 400 to 700, or about 500 to 600 times the CMC. In some embodiments, each detergent concentration in the lysing reagent is between about 0.1 to 100, about 1.0 to 90, about 10 to 80, about 20 to 70, about 30 to 60, or about 40 to 50 times the CMC.

In some embodiments, the lysing reagent includes one or more metal chelators. Non-limiting examples of suitable metal chelators include, for example, ethyleneglycoltetraacetic acid (EGTA) and ethylenediaminetetraacetic acid (EDTA). In some embodiments, the concentration of the metal chelators in the lysing reagent is between about 50 mM to 1.0 M, about 100 mM to 0.75 M, about 110 mM to 500 mM, about 125 mM to 500 mM, or about 125 mM to 450 mM.

In some embodiments, the lysing reagent includes one or more reducing agents. Non-limiting examples of suitable reducing agents include, for example 2-mercaptoethanol or dithiothreitol. In some embodiments, the concentration of the reducing agent in the lysing reagent is between about 10 mM to 20 M, about 15 mM to 15 M, about 50 mM to 14 M, about 100 mM to 14 M, or about 110 mM to 15 M. In some embodiments, the concentration of the reducing agent in the lysing reagent is between about 1 mM to 100 mM, about 10 mM to 90 mM, about 20 mM to 80 mM, about 30 mM to 70 mM, about 40 mM to 60 mM, or about 45 mM to 55 mM.

In some embodiments, at least one DNA intercalating dye is added to the lysing reagent prior to use. In some embodiments, the DNA intercalating dyes are dyes that create a covalent bond to both DNA strands after activation with a light source of the appropriate wavelength and dosage. Without wishing to be bound by theory, in some embodiments, the covalent bond renders at least some of the DNA present in the sample unamplifiable. Non-limiting examples of suitable DNA intercalating dye include ethidium monoazide (EMA) and propidium monoazide (PMA).

In some embodiments, the primers used in the amplification region are labeled with a detectable marker or a binding moiety prior to beginning the amplification operation.

In some embodiments, modified nucleotides that either contain a tag or are modified to enable the downstream conjugation of tags are used in the amplification operation. By way of example, but not by way of limitation, tag-modified nucleotides include, but are not limited to, a nucleotide modified with a diethylaminocoumarin (DEAC), Cyanine 3 (Cy3), Cyanine 5 (Cy5), Fluorescein (FITC), Lissamine, R110, R6G, Tetramethylrhodamine (TAMRA), or Texas Red dye. Example for a modified nucleotides enabling subsequent tagging would be, but are not limited to, a nucleotide modified with an Amino-digoxigenin (DIG), Biotin, or Dinitrophenyl (DNP).

In some embodiments, the labeling of the DNA amplicon is achieved through subsequent incubation with an intercalating dye. Non-limiting examples of suitable intercalating dyes include, but are not limited to, PicoGreen, OliGreen, RiboGreen, SYBR Gold, SYBR Green I, SYBR Green II, SYBR Safe, TOTO-1, YOYO-1, YOYO-3, POPO-1, BOBO-1, JOJO-1, POPO-3, LOLO-1, BOBO-3, YOYO-3, TOTO-3, SYTOX—Blue, SYTOX—Green, SYTOX—Orange, SYTOX—Red, and EtBr.

In some embodiments, the concentration of the DNA intercalating dye in the lysing reagent is between about 0.01 µM to 1.0 µM, about 0.1 µM to 0.9 µM, 0.2 µM to 0.8 µM, about 0.3 µM to 0.7 µM, or about 0.4 µM to 0.6 µM.

In some embodiments, the lysing reagent may be pretreated with one or more nucleases prior to use. In some embodiments, the nucleases are neutralized prior to usage of the microbial lysis solution. Without wishing to be bound by theory, the nucleases used may depend on the downstream sequences of interest. By way of example, but not by way of limitation, in some embodiments, the nucleases are selected from, but not limited to, EcoRI, HindIII, SalI, HhaI, DdeI, RsaI, Sau3AI and MspI.

In some embodiments, the lysing reagent may have pretreated with elevated dosages of ultra-violet irradiation, specifically in the range of approximately 260 nm. Without wishing to be bound by theory, UV induces nicks in DNA backbone rendering it generally non-amplifiable.

In some embodiments, an anion exchanger (e.g., an anion exchanger resin) is used to capture/immobilize select eukaryote and/or microbial genomic material. The anion exchange resin may be positioned in one or more reservoirs or channels of the fluidic device. In some embodiments, an anion exchange resin is one or more weak anion-exchange resins (WAX). Examples of WAX include, but are not limited to, carboxymethyl (CM), diethylaminopropyl (ANX), diethylethanolamine (DEAE), Amberlite Ira67, Purolite A847, Amberlite Ira96, Amberlite IRA96SB, Dowex Marathon WBA, Dowex Upcore Mono WB-500, Purolite A835, Dowex Monosphere 77, and Dowex Monosphere 66.

In some embodiments, the WAX resin contains at least one tertiary amine functional group.

In some embodiments, an anion exchange resin is one or more strong anion-exchange resins (SAX). Examples of SAX include, but are not limited to, —O—CH$_2$—CHOH—CH$_2$—O—CH$_2$—CHOH—CH$_2$—N$^+$(CH$_3$)$_3$, Amberjet Up4000, Amberjet 9000 OH, Amberlite FPA40 Cl, and Dowex Upcore Mono MA-600.

In some embodiments, a SAX based resin contains at least one quaternary amine functional group.

In some embodiments, the anion exchange resin is a combination of at least one WAX and at least one SAX.

In some embodiments, the form of the anion exchange resin is selected from fibers, membranes, sorbents, gels, and filter paper. In some embodiments, the sample with the lysed select eukaryote cells and/or lysed microbial cells is passed through or contacted with the anion exchange resin. In some embodiments, the anion exchange resin is in a solution.

In some embodiments, a support substrate may be positioned in one or more reservoirs or channels of the fluidic device. In some embodiments, the support substrate comprises silica, glass, metal, polystyrene-based material, cellulose-based material, agarose-based material, dextran-based material, methacrylate-based material, sepharose-based material, or a combination thereof. In some embodiments the support substrate is porous.

In some embodiments, the support substrate comprises of a polymer such as, by way of example but not by way of limitation, polystyrene or poly(methyl methacrylate).

In some embodiments, in cases where the solid support substrate is porous, the anion exchange resin may be conjugated to the outer layer of the said substrate. In other embodiments, the anion exchange resin is conjugated to the inner portion of the solid support substrate. In further embodiments, no distinction is made as to where on the solid support resin the anion exchange resin is conjugated.

By way of a non-limiting example, and not wishing to be bound by theory, porous solid support substrates are beneficial as they facilitate an increased surface area for binding while having similar volumes to non-porous materials. Increased surface area may, in some embodiments be beneficial, for example, to increase the binding capacity of the system, or to increase the kinetics of the system, or two achieve both simultaneously.

In some embodiments, the solid support substrate is a bead or sphere has a largest cross-sectional dimension between about 10 to 100 µm, between about 20 to 90 µm, between about 30 to 80 µm, between about 40 to 70 µm, or between about 50 to 60 µm.

In another embodiment, the support substrate is a bead or sphere have a largest cross-sectional dimension between about 0.01 to 10 µm, about 0.1 to 9.0 µm, about 1.0 to 8.0 µm, about 2.0 to 7.0 µm, about 3.0 to 6.0 µm, or between about 4.0 to 5.0 µm.

In some embodiments, the support substrate has a particular outer surface area. In some embodiments, the outer surface area is between about $3\times10$ to $3\times10^2$ µm$^2$, between about $3\times10^{-2}$ to $2.5\times10^2$ µm$^2$, between about 1 to $2\times10^2$ µm$^2$, between about $1\times10^1$ to $1.5\times10^2$ µm$^2$, between about $3\times10^1$ to $1\times10^2$ µm$^2$, between about $5\times10^2$ to $1.0\times10^2$ µm$^2$, between about $3\times10^2$ to $3\times10^4$ µm$^2$, between about $1\times10^2$ to $2.5\times10^4$ µm$^2$, between about $3\times10^3$ to $2\times10^4$ µm$^2$, between about $5\times10^3$ to $1.5\times10^4$ µm$^2$, or between about $7\times10^3$ to $1.5\times10^4$ µm$^2$.

In some embodiments, a wash buffer may be positioned in one or more reservoirs or channels of the fluidic device.

In some embodiment, the pH of the wash buffer is between about 3.0 to 7.5, about 3.5 to 7.0, about 4.0 to 6.5, about 4.5 to 6.0, or about 5.0 to 5.5.

In some embodiments, the wash buffer has a salt concentration between about 0.5 M to 3.0 M, about 0.75 M to 2.75 M, about 1.0 M to 2.5 M, about 1.25 M to 2.25 M, or about 1.5 M to 2.0 M.

In some embodiments, the wash buffer comprises one or more surfactants, as described above. By way of example, but not by way of limitation, in some embodiments, surfactants include, but are not limited to, Tween and Triton-X. In some embodiments, the Tween and/or Triton-X concentration is between about 0.01% to 1.0% (v/v), about 0.1% to 0.9% (v/v), about 0.2% to 0.8% (v/v), about 0.3% to 0.7% (v/v), or about 0.4% to 0.6% (v/v).

In some embodiments, the wash buffer comprises one or more detergents. By way of example, but not by way of limitation, in some embodiments, detergents include, but are not limited to, zwitterionic detergents. In some embodiments, the zwitterionic detergent concentration is between about 0.1× to 350×CMC, about 1.0× to 300×CMC, about 10× to 250×CMC, about 50× to 200×CMC, or about 100× to 150×CMC.

In some embodiments, the wash buffer comprises one or more of the following: 1) monovalent salt, e.g., as NaCl or KCl, at between about 0 to 150 mM, about 10 to 250 mM, about 25 to 475 mM, about 50 to 525 mM, or about 75 to 750 mM; 2) buffered to a near neutral pH, for example between about 6-9; and 3) surfactants, e.g., Tween-20 or Triton X-100 at between about 0.01% to 1.0% (v/v), about 0.02% to 0.9% (v/v), about 0.03% to 0.8% (v/v), about 0.04% to 0.7% (v/v), or about 0.05% to 0.6% (v/v).

In some embodiments, an elution buffer may be positioned in one or more reservoirs or channels of the fluidic device.

In some embodiments, the pH of the elution buffer is between about 11.5 to 13.5. In some embodiments, the elution buffer comprises a buffering agent such as sodium phosphate or potassium phosphate. In some embodiments, the concentration of sodium phosphate or potassium phosphate in the elution buffer is between about 0.01 M to 1 M, about 0.1 M to 1.8 M, about 0.4 M to 1.6 M, about 0.8 M to 1.4 M, or about 1.0 M to 1.2 M.

In some embodiments, the elution buffer comprises sodium hydroxide or potassium hydroxide. In some embodiments, the concentration sodium hydroxide or potassium hydroxide is between about 10 to 500 mM, about 30 to 450 mM, about 50 to 400 mM, about 70 to 350 mM, about 90 to 300 mM, about 110 to 250 mM, or about 130 to 200 mM.

In some embodiments, the elution buffer comprises a monovalent salt. In some embodiments, the concentration of the one or more monovalent salts in the elution buffer in 305 is between about 0 mM to 200 mM, about 25 mM to 175 mM, about 50 mM, to 150 mM, about 75 mM to 125 mM, or about 90 mM to 110 mM. In some embodiments, the elution buffer does not contain any monovalent salts.

Additional non-limiting examples of suitable buffering agents include tris, sodium-phosphate, and potassium phosphate. In some embodiments, the concentration of the buffering agent is between about 1 mM to 500 mM, about 50 mM to 450 mM, about 100 mM to 400 mM, about 150 mM to 350 mM, or about 200 mM to 300 mM in the elution buffer.

In some embodiments, an invasion buffer may be positioned in one or more reservoirs or channels of the fluidic device.

In some embodiments, the invasion buffer includes one or more monovalent salts. In some embodiments, the monovalent salt is NaCl or KCl. In some embodiments, the concentration of monovalent salt in the invasion buffer is between about 1 mM to 150 mM, about 5 mM to 145 mM, about 15 mM to 130 mM, about 25 mM to 115 mM, about 35 mM to 100 mM, about 45 mM to 85 mM, or about 55 mM to 70 mM. In some embodiments, the invasion buffer contains no monovalent salts.

In some embodiments, the invasion buffer comprises one or more surfactants. In some embodiments, the surfactant reduces non-specific binding. In some embodiments, the concentration of the surfactant in the invasion buffer is between about 0.01% to 1.0% (v/v), about 0.1% to 0.9% (v/v), about 0.2% to 0.8% (v/v), about 0.3% to 0.7% (v/v), or about 0.4% to 0.6% (v/v).

In some embodiments, the invasion buffer includes components to vary the excluded volume (e.g., crowding agents). By way of example, but not by way of limitation, crowding agents include, but are not limited to, polyethylene glycol (EG), EG-200, EG-250, EG-300, EG-400, EG-500, EG-750, EG-1,000, EG-9,500, EG-2,000, EG-4,000, EG-5,000, EG-6,000, EG-8,000, EG-10,000, EG-12,000, EG-13,000, EG-20,000, dextrans (DX), polyvinyl-alcohols (PVA), Ficolls (FC), DX-1,000, DX-5,000, DX-12,000, DX-50,000, DX-80,000, PVA 89k-98k, PVA 85k-124k, PVA 130k, PVA 31k-50k, PVA 50k-80k, PVA 70k-100k, PVA 90k-120k, PVA 170k-250k, PVA 61k, PVA 31k, PVA 130k, PVA 67k, PVA 27k, PVA 25k, FC-400, FC-70, FC-40, glycerol, glucose, and sucrose. In some embodiments, the concentration range of the crowding agent in the invasion buffer is between about 1% to 20% (v/v), about 3% to 17% (v/v), about 6% to 14% (v/v), or about 9% to 11% (v/v) of the total volume of invasion buffer.

In some embodiments, the invasion buffer comprises one or more DNA denaturants. By way of example, but not by way of limitation, DNA denaturants include, but are not limited to, DMSO, formamide, and betaines. invasion buffer. In some embodiments, the DMSO and/or formamide are between about 1% to 30% (v/v), about 5% to 25% (v/v), about 10% to 20% (v/v), or about 14% to 16% (v/v) of the total volume of invasion buffer. In some embodiments, the concentration of the betaines in the invasion buffer is between about 0.1 M and 2.5 M, about 0.5 M and 2.0 M, or about 1.0 M and 1.5 M.

In some embodiments, a wash buffer, such as a DIANA wash buffer, serves as a wash buffer after the addition of DIANAs.

In some embodiments, the DIANA wash buffer comprises one or more of the following: 1) monovalent salt, e.g., as NaCl or KCl, at between about 50 to 650 mM, about 100 to 600 mM, about 150 to 550 mM, about 200 to 500 mM, about 250 to 450 mM, or about 300 to 400 mM; 2) buffered to a near neutral pH, for example between about 6-9; and 3) surfactants, e.g., Tween-20 or Triton X-100 at between about 0.1% to 1.0% (v/v), about 0.2% to 0.9% (v/v), about 0.3% to 0.8% (v/v), about 0.4% to 0.7% (v/v), or about 0.5% to 0.6% (v/v). In some embodiments, the wash buffer is heated.

In some embodiments, the DIANA wash buffer includes one or more DNA destabilizing or denaturing agents, e.g., DMSO, betaines, and formamide. In some embodiments, the DMSO and/or formamide are between about 10% to 30% (v/v), about 15% to 25% (v/v), about 10% to 20% (v/v), or about 14% to 16% (v/v) of the total volume of invasion buffer. In some embodiments, the concentration of the betaines in the invasion buffer is between about 0.1 M and 2.5 M, about 0.5 M and 2.0 M, or about 1.0 M and 1.5 M.

In some embodiments, the pH of the DIANA wash buffer is above 9.0 and includes between about 0 mM to 300 mM, about 50 mM to 250 mM, about 100 mM to 200 mM, or about 125 mM to 175 mM of monovalent salts and/or surfactants. In some embodiments, the pH of the wash buffer is below 6.0 and includes between about 0 mM to 800 mM, about 50 mM to 750 mM, about 100 mM to 700 mM, about 150 mM to 650 mM, or about 200 mM to 600 mM, about 250 mM to 550 mM, about 300 mM to 500 mM, or about 350 mM to 450 mM of monovalent salts and/or surfactants.

In some embodiments, the process of washing lasts between about 0.01 to 5 minutes, about 1 to 10 minutes, or about 5 to 30 minutes. In some embodiments, multiple wash steps are conducted, wherein between each wash step the solid substrates are immobilized. In some embodiments, nucleic acids, either dsDNA or ssDNA or both, are added to the wash buffer.

By way of example, but not by way of limitation, in some embodiments, the DIANA washing step comprises washing DIANA oligomers that are sized between about 14 to 18 bases, wherein the lower wash temperature is defined as about: TM(DNA)+20° C. and the upper wash temperature is 99° C.

By way of example, but not by way of limitation, in some embodiments, the DIANA washing step comprises washing DIANA oligomers that are larger than 18 bases, wherein the lower wash temperature is defined as about: TM(DNA)+0.9° C.×(number of bases) and the upper wash temperature is 99° C.

By way of example, but not by way of limitation, in some embodiments, the DIANA washing step comprises washing DIANA oligomers that are smaller/shorter than 14 bases, wherein the lower wash temperature is defined as about: TM(DNA)+1.25° C.×(number of bases) and the upper wash temperature is 99° C.

In some embodiments, a gas or liquid entering the device is sterilized by at least one porous membranes disposed in the device. In some embodiments, the surface of the porous membrane is hydrophilic in nature or hydrophobic in nature. In some embodiments, the porous membrane is oleophobic.

In some embodiments, the sterilizing porous membrane has pores between about 0.02 µm to 10 µm, between about 0.05 µm to 4 µm, between about 0.1 µm to 3 µm, or between about 1.0 µm to 50 µm.

In some embodiments, the gas is subjected to UV based decontamination processes.

By way of example, but not by way of limitation, in some embodiments, the detectable markers include, but are not limited to fluorescent dyes, horseradish peroxidase (HRP), luciferase, methoxycoumarin, dansyl, pyrene, Alexa Fluor 350, AMCA, Marina Blue dye, dapoxyl dye, dialkylaminocoumarin, bimane, hydroxycoumarin, cascade blue dye, Pacific Orange dye, Alexa Fluor 405, Cascade Yellow dye, Pacific Blue dye, PyMPO, Alexa Fluor 430, Fluorescein, Alexa Fluor 488, Oregon Green 488, BODIPY 493/503, Oregon Green 514, Alexa Fluor 514, Alexa Fluor 532, BODIPY TMR, Alexa Fluor 555, Alexa Fluor 546, BODIPY 558/568, Rhodamine Red dye, Alexa Fluor 568, BODIPY 581/591, Alexa Fluor 594, Texas Red dye, Alexa Fluor 610, Alexa Fluor 633, Alexa Fluor 635, Alexa Fluor 647, Alexa Fluor 660, Alexa Fluor 680, Alexa Fluor 700, Alexa Fluor 750, and Alexa Fluor 790.

By way of example, but not by way of limitation, detectable markers enabling indirect detection include, but are not limited to, digoxigenin (DIG), biotin, or dinitrophenyl.

In some embodiments, the detectable marker may produce an optical signal that is detectable, for example, by visual inspection by a user and/or fluorescence detection methods.

In some embodiments, the amplicon is greater than about 400 bp. In some embodiments, the amplicon is between about 400 to 4000 bp, about 700 to 3700 bp, about 1000 to 3400 bp, about 1300 to 3100 bp, about 1600 to 2700 bp, about 1900 to 2400 bp, or about 2100 to 2200 bp. In some embodiments, use of amplicons of the lengths disclosed above are advantageous for downstream processing (e.g., detection and identification of microbial genomic materials) in the methods disclosed herein.

In some embodiments, some or all of the following primers may be used:

```
                                              (SEQ ID NO: 38)
CCC CCC CCT CAG TTA TCG TTT ATT TGA TAG TAC C;

(SEQ ID NO: 39)
CCC CCC CCT CAG TTA TCG TTT ATT TGA TAG TTC C;

(SEQ ID NO: 40)
CCC TTC CCA GAG TTT GAT CAT GGC TCA G;

(SEQ ID NO: 41)
CCC TTC CAG AGT TTG ATC CTG GCT CAG;

(SEQ ID NO: 42)
CCC CCC GGT TAC CTT GTT ACG ACT T;

(SEQ ID NO: 43)
CCC CCGG CTA CCT TGT TAC GACT T;

(SEQ ID NO: 44)
CCC TTC CCT GAT GAC TCG TGC CTA CTA;

(SEQ ID NO: 45)
CCC TCT CCC TGA TGA CTT GCG CTT ACT A
```

In some embodiments, additional and/or alternative primer sequences may be used to amplify the microbial genomic material. Primer sequence development is well known to those skilled in the art.

In some embodiments, only bacterial genomic material is amplified. In some embodiments, only fungal genomic material is amplified. In some embodiments, both fungal and bacterial targets are amplified. In some embodiments, synthetic targets are amplified. In some embodiments, synthetic targets include, but are not limited to, plasmids and synthetic genes. By way of example, but not by way of limitation, in some embodiments, plasmids include DNA fragments, such as, e.g., M13mp18, pBR322, pCLIK, pCLus, pCMV-Cluc, pKLAC2, PMAL-p5×, pNEB206A, pSNAPf, pSV40-CLuc, pTK-GLuc, pTXB1, pTYB21, pUC19, and θX174.

In some embodiments, the DIANA probes are stored in a liquid form, whereas in preferred embodiments, the DIANA probes are stored dry.

In some embodiments, exemplary oligomer sequences for DIANAs used for microbial detection and identification are listed in Table 1.

TABLE 1

DIANA Probe Sequences

| Group | Target Microorganism | Sequence | SEQ ID NO. |
|---|---|---|---|
| Gram positive | Staphylococcus aureus | TCGAAGAGCAGGCAA | 1 |
| | Staphylococcus epidermidis | TCGAGGTTTACCAATG | 2 |
| | Staphylococcus lugdunensis | TCGAGGTTTACCAATG | 2 |
| | Staphylococcus warneri | GAGGTATTTACCAATG | 3 |
| | Enterococcus faecalis | AAGTCAATGATTGCAGG | 4 |
| | Enterococcus faecium | TTGTCAATGAGAGTAGG | 5 |
| | Streptococcus agalactiae | TACACAATTAATGAGAA | 6 |
| | Streptococcus pyogenes | GCAATCAGAGAGAATA | 7 |
| | Streptococcus mitis | AATTCGTTTACAGTACG | 8 |
| | Streptococcus oralis | AATTCGTTTACAGTACG | 8 |
| | Streptococcus pneumoniae | TCGGATGATACCAATT | 9 |
| | Escherichia coli | ACGGTCATAGTCTACG G | 10 |

TABLE 1-continued

DIANA Probe Sequences

| Group | Target Microorganism | Sequence | SEQ ID NO. |
|---|---|---|---|
| Gram Negative | Pseudomonas aeruginosa | CGCGGTGATTCTAGAGT | 11 |
| | | CGCGGTGATACTAGAGT | 12 |
| | Serratia marcescens | AATTCAAGTGGTGGAA | 13 |
| | | AATTCGAGTGGTGGAA | 14 |
| | Acinetobacter baumannii | GGTGATAGAGATCCAT | 15 |
| | Enterobacter aerogenes | CTCGTTCGAGAGACAC | 16 |
| | Enterobacter cloacae | CTCGTTCGAGAGACAC | 16 |
| | Klebsiella oxytoca | CTCGTTCGAGAGACAC | 16 |
| | Klebsiella pneumoniae | CTCGTTCGAGAGACAC | 16 |
| Fungal | Candida albicans | GTATTTACCGATGGG | 17 |
| | Candida glabrata | ACGTAAGGTCATGTGC | 18 |
| | Candida krusei | GATCTAAAAGGTGCC | 19 |
| | Candida tropicalis | TCAGGCTTCTGTAAC | 20 |
| | | AGCGGTTTTCCGATC | 21 |
| | Candida parapsilosis | TGCGTAGTTTTTCTA | 22 |
| Pan-Bacterial | Relevant to the majority of bacterial BSIs | CCTGATGGTCCCATAGAT | 23 |
| Pan-Candida | Relevant to the majority of fungal BSIs | CAGGATCTTTGGTTGT | 24 |

In some embodiments, the DIANA probes are used to detect and identify antibiotic resistance microbial cells. Non-limiting examples of sequences for identification of these nucleic acid biomarkers are listed in Table 2.

TABLE 2

DIANA Probes Sequences for Resistance Identification

| Target | Sequence | SEQ ID NO. |
|---|---|---|
| MecA | GCATTGATAGGAGATC | 25 |
| | CCAGGGTAATTGAGAC | 26 |
| | CAGTGTTAGCAACTGC | 27 |
| VanA | GTCCTATCCATTTGCAT | 28 |
| | CTACTCGGACTTGCGC | 29 |
| | AAACGACAGTATAACAG | 30 |
| VanB | TCGCAATTCAAGAAGG | 31 |
| | TTGTCCCATCCATTCG | 32 |
| | GGTTTCCTGCTTGGAC | 33 |
| VanA/VanB | TGGCTGGAGTGTCGG | 34 |
| OXA-48 | CTGAACCACAAGTAGGA | 35 |
| blaNDM-1 | ACCAAGCTGTTGCGTAAC | 36 |
| blaKPC | AGTACGGACAACAGTCT | 37 |

In some embodiments, the incubation of DIANAs and the microbial genomic material (e.g., amplified microbial DNA) is at a temperature between about 65° C. to 99° C., about 70° C. to 95° C., about 75° C. to 90° C., or about 80° C. to 85° C.

By way of example, but not by way of limitation, in some embodiments, the DIANA addition operation includes DIANA oligomers that have between about 14 to 18 bases, wherein the lower invasion temperature is defined as about: $T_M(DNA)+15°$ C. and the upper invasion temperature is 99° C. $T_M(DNA)$ is defined as the melting temperature of a DNA oligomer with identical composition and sequence to the DIANA oligomer when placed in nearly identical solution conditions (electrolytes strength, buffer, pH, other additives, etc.).

By way of example, but not by way of limitation, in some embodiments, the DIANA addition operation includes using DIANA oligomers that are larger than 18 bases, wherein the lower invasion temperature is defined as about: $T_M(DNA)+ 0.7°$ C.×(number of bases) and the upper invasion temperature is 99° C.

By way of example, but not by way of limitation, in some embodiments, the DIANA addition operation includes using DIANA oligomers that are smaller/shorter than 14 bases, wherein the lower invasion temperature is defined as about: $T_M(DNA)+1.1°$ C.×(number of bases) and the upper invasion temperature is 99° C.

In some embodiments, the DIANAs are modified to contain a binding moiety. In some embodiments, the binding moiety binds the DIANA to a solid substrate. In some embodiments, the binding DIANA to a solid substrate is useful for separation or washing steps downstream. By way of example, but not by way of limitation, in some embodiments, the binding moieties include, but are not limited to, non-covalent binding moieties (e.g., such as biotin, digoxin, digitoxin) or covalent binding moieties (e.g., COOH group, NHS-ester group, malemide chemistry, and Click chemistry).

In some embodiments, the binding moiety is spaced from the DIANA probe by one or more linkers. In some embodiments, the linker is a single molecule. In some embodiments the linker is comprised of a chain of multiple individual molecules, either linear or branched, that are combined to create a single linker molecule.

In some embodiments, the linker is selected from the group consisting of: (ethylene)glycol, di(ethylene)glycol, tri(ethylene)glycol, poly(ethylene)glycol, carbon linker, amino acids, a silane based linker, or any combination thereof. In some embodiments, the linker serves to distance the DIANA tagged DNA fragment from the surface of the solid phase substrate to which the DIANA is bound to.

In some embodiments, the linker is may be branched. By way of example but not by way of limitation, it may be beneficial to have a linker that leads off of the DIANA probe and after a certain distance branches off or divided into two or more linkers, where each branch or new linker contains one or more binding moieties.

In some embodiments, the linker length is between about 20 to 200, about 40 to 180, about 60 to 160, about 80 to 140, or about 100 to 120 atoms. In some embodiments, the linker length is at least 40 atoms. The disclosed linker lengths are not commonly used in the art.

In some embodiments, one or more binding moieties are used along a single linker. In some embodiments, two or more binding moieties along a single linker, wherein each linker has 1 or more binding moieties and wherein each binding moiety is attached to a different location along the oligomer. In some embodiments, multiple binding moieties increase the surface binding kinetics and/or yield and/or efficiently, and/or strength.

In some embodiments, the DNA amplicon is first tagged with one or more DIANAs and then the hybrid complex is captured onto the solid-phase surface.

In some embodiments, the DIANA is incubated with a solid surface prior to capturing the amplicon.

In some embodiments, the solid-phase surface is a bead, nanoparticle, microparticle or flat substrate. In some embodiments, the solid-phase surface is further chemically modified to facilitate binding of the DIANA to it.

In some embodiments, the methods and/or devices described herein may be utilized for the analysis (e.g., identification, and/or detection, and/or screening, and/or qualification) of more than 10 individual microbial pathogens from a single whole-blood sample. In some embodiments, the whole-blood sample introduced into the fluidic device has a volume of at least 1 mL. In some cases, the methods and/or fluidic devices described herein may be utilized for the analysis (e.g., identification, and/or detection, and/or screening, and/or quantification, and/or monitoring) of bacteria and/or fungi. In some embodiments, the analysis comprises high sensitivity chemiluminescent detection.

In some embodiments, the methods and/or devices lyse both bacteria and fungi in a single reaction, in parallel, though chemical reactions (e.g., without the use of mechanical or electrical forces). In certain embodiments, the methods and/or devices described herein comprise depletion of select eukaryote DNA from a whole-blood sample without the use of a centrifuge. In certain embodiments, the methods and/or devices described herein does not shear genomic material during the lysis process (e.g., thereby enabling the extraction and/or isolation of high molecular weight genomic material of which is typically over 5 kbp in length). In certain embodiments, the methods and/or devices described herein comprise enzymatically producing amplicons greater than 1000 bp in length. In some cases, the method and/or devices described herein comprise immobilizing DNA to a solid substrate in under 30 minutes wherein the DNA length is greater than 1 kbp.

In some embodiments, the methods and/or devices described herein do not require the use of any chaotropic salt for any of its processes.

In certain embodiments, the methods and/or devices described herein comprise DIANA probes to capture and immobilize DNA to a solid surface or substrate with sequence high sequence specificity. In some cases, the methods and/or devices described herein comprise combining a plurality of DIANA probes within one or more processing chambers such that a combination of one or more signals elucidates the identification of the pathogen (e.g., thereby reducing the number of processing chambers needed to elucidate the identification of the pathogen).

In some embodiments, one or more operations, or set of operations, described herein may be conducted semiautomatically or automatically.

In certain embodiments, one or more fluidic reservoirs may store one or more reagents and/or may be configured to receive a waste fluid.

In some embodiments, the methods and/or devices comprise the transfer (e.g., flow) of one or more fluids along three planes (X, Y, and Z) in both positive and negative directionality (e.g., through the use of flow restriction structures). In certain embodiments, the plurality of fluidic channels used for transferring fluids from a first fluidic reservoir to a second fluidic reservoir are located within a single plane. In certain embodiments, one or more fluids flowed in the fluidic device may have a relatively large volume (e.g., 0.5-10 ml) or a relatively reduced volume (e.g., 0.01 µl-500 µl).

In some cases, the methods and/or devices comprises mixing, agitation, and/or homogenization of a fluid (e.g., and one or more reagents) via the addition, either as a stream or as a pulsation, of a sterile gas to a chamber.

In some embodiments, the presence of a signal (e.g., an optical signal) in one or more of the detection regions indicates the presence of the genomic material of a particular microbial pathogen. In some embodiments, the detection of a particular analyte (e.g., pathogen) is provided through a combinatorics (e.g., multiplexing) method. In such an approach, the number of analytes detected may be larger than the number of active detection regions used for detection. In some embodiments, the fluidic device comprises two or more detection regions. In some embodiments, the particular combination of detection regions that detect one or more amplicons (e.g., by producing a detectable signal such as an optical signal) may indicate the presence of one or more particular pathogen.

In one example, a signal detected in a first detection region and a second detection region, but not a third detection region, indicates the presence of a first pathogen in the patient sample. A signal detected in the first detection region and the third detection region, but not the second detection region, indicates the presence of a second pathogen in the patient sample, different than the first pathogen.

The use of a combinatorics approach to detection may provide several advantages over traditional, 1-to-1 detection, methods (e.g., detection of a pathogen in a single well, and/or single pathogen detection across multiple wells) including, for example, simplified fluidic channel design, reduced footprint, reduced processing times, increased accuracy, and/or simplified detection.

In some embodiments, a single type of optical signal (e.g., an optical signal at a particular wavelength or frequency) may be used for the detection of a plurality of pathogens. For example, a single fluorescent tag may be used in the fluidic device and, in the presence of a pathogen, one or more detection regions produce a detectable optical signal from the fluorescent tag indicating the presence of the genomic material of a particular microbial pathogen.

By way of example, but not by way of limitation, if the pathogen panel that one wishes to use incorporates the following microbial pathogens: *Staphylococcus aureus, Enterococcus faecalis, Escherichia coli, Candida albicans, Candida glabrata*, and *Candida krusei*, one could use the following 4 chamber layout for DIANA-based processes:

Reaction Chamber (1): SEQ ID NO 23; Reaction Chamber (2): SEQ ID Nos 1 and 17; Reaction chamber (3): SEQ ID NOs 4 and 18; Reaction chamber (4): SEQ ID Nos 10 and 19. Thus, if by way of example but not by way of limitation, *Staphylococcus aureus* was detected then Reaction Chambers 1 and 2 would produce a detectable signal. Alternatively, if by way of example but not by way of limitation, *Candida glabrata* was detected then Reaction Chamber 3 would produce a detectable signal.

In the case of pathogen-specific genomic material, one could identify each different pathogenic genomic material (PGM) associated with a particular pathogen as $PGM_n$ wherein n=1, 2, 3, . . . , n. For example, in some embodiments, in a fluidic device design to identify one of fifteen potential pathogens, the fluidic device could identify $PGM_n$ wherein n=1, 2, 3, . . . , 15, where the fifteen potential pathogens could be detected using 8 detection regions. In an exemplary embodiment, shown in Table 3, the presence of particular capture oligomers in one or more detection regions would indicate the presence of a particular pathogen in the patient sample.

TABLE 3

| Detection Region | Capture Oligomers |
|---|---|
| 1 | $PGM_1 + PGM_2 + PGM_3 + PGM_4 + PGM_5$ |
| 2 | $PGM_6 + PGM_7 + PGM_8 + PGM_9 + PGM_{10}$ |
| 3 | $PGM_{11} + PGM_{12} + PGM_{13} + PGM_{14} + PGM_{15}$ |
| 4 | $PGM_1 + PGM_6 + PGM_{11}$ |
| 5 | $PGM_2 + PGM_7 + PGM_{12}$ |
| 6 | $PGM_3 + PGM_8 + PGM_{13}$ |
| 7 | $PGM_4 + PGM_9 + PGM_{14}$ |
| 8 | $PGM_5 + PGM_{10} + PGM_{15}$ |

For example, in a particular embodiment, if a detectable signal is generated in detection regions 1 and 4, the only common PGM is $PGM_1$, indicating the particular pathogen present in the patient sample corresponding to $PGM_1$. As another example, in another embodiment, if a detectable signal is generated in detection regions 1 and 7, the only common PGM is $PGM_4$, indicating the particular pathogen present in the patient sample corresponding to $PGM_4$.

Those skilled in the art would understand, based upon the teachings of this specification, that such a combinatorics approach is not limited to 15 potential pathogens and/or 8 detection regions, but that the fluidic device could be used to detect two or more, four or more, six or more, eight or more, ten or more, twelve or more, fifteen or more, or twenty or more pathogens using two or more (e.g., four or more, six or more, eight or more, ten or more, twelve or more, fifteen or more) detection regions.

In some embodiments, the detection of one or more pathogens does not use a combinatorics approach. For example, each detection region, in certain embodiments, corresponds to a single pathogen.

In another exemplary embodiment, the fluidic device comprises detection regions with capture oligomers for:
1. Five different fungal pathogens: $F_1$, $F_2$, $F_3$, $F_4$, and $F_5$
2. Five different Gram-positive pathogens: $GP_1$, $GP_2$, $GP_3$, $GP_4$, and $GP_5$
3. Five different Gram-negative pathogens: $GN_1$, $GN_2$, $GN_3$, $GN_4$, and $GN_5$
4. Three additional pathogens which are any combination of Gram positives, Gram negatives, or Fungi—$A_1$, $A_2$, and $A_3$, respectively.

In such an exemplary embodiment, the combinatorics based detection of one or more pathogens is shown in Table 4.

TABLE 4

| Detection Region | Capture Oligomers |
|---|---|
| 1 | $F_1 + F_2 + F_3 + F_4 + F_5$ |
| 2 | $GP_1 + GP_2 + GP_3 + GP_4 + GP_5$ |
| 3 | $GN_1 + GN_2 + GN_3 + GN_4 + GN_5$ |
| 4 | $A_1$ |
| 5 | $A_2$ |
| 6 | $A_3$ |
| 7 | $F_1 + GP_1 + GN_1$ |
| 8 | $F_2 + GP_2 + GN_{12}$ |
| 9 | $F_3 + GP_3 + GN_3$ |
| 10 | $F_4 + GP_4 + GN_4$ |
| 11 | $F_5 + GP_5 + GN_5$ |

For example, in such embodiments, 18 different pathogens with 11 detection regions. In an exemplary embodiment, the detection of a signal in detection regions 1 and 11 would indicate detection of $F_1$, whereas the detection of a signal in detection regions 2 and 8 would indicate detection of $GP_2$. Other combinations of signals and pathogens are also possible.

EXAMPLES

The following examples are intended to illustrate certain embodiments described herein, including certain aspects of the present invention, but do not exemplify the full scope of the invention.

Example 0

The following example demonstrates an exemplary set of operations using a fluidic device as described herein.

In some embodiments, the set of operations conducted in the fluidic device includes one or more of the following steps or processes: (1) Deplete, selectively, select eukaryote DNA from the sample; (2) Lyse one or more of the microbial cells in the inputted sample, wherein the lysing of one or more microbial cells releases a plurality of microbial genomic materials; (3) Isolate the plurality of microbial genomic materials (namely DNA and/or RNA); (4) Amplify the plurality of microbial genomic materials; (5) Contact and/or introduce the amplified microbial genomic materials (herein "amplicons") with a plurality of duplex DNA Invading Artificial Nucleic Acids (DIANAs), wherein each DIANA targets one or more amplicons originating from a specific pathogen or group of pathogens, and detecting binding of one or more DIANAs to their target amplicon, wherein the detection of binding indicates the presence of one or more specific microbial species in the original sample.

In some embodiments, the set of operations comprises: (1) Select eukaryote Cell Lysis and removal of released genomic material; (2) Pathogen Lysis; (3) Isolation of Microbial Genomic Material; (4) Enzymatic Amplification; and (5) DNA Invading Artificial Nucleic Acid (DIANA) based detection\classification\identification.

In some embodiments, the set of operations comprises: (1) Depletion of select eukaryote DNA from the sample; (2) Lysing one or more microbial cells in the sample, wherein the lysing of one or more microbial cells releases a plurality of microbial genomic materials; (3) Isolating the plurality of microbial genomic materials; (4) Amplifying the plurality of microbial genomic materials; (5) Contacting the amplified microbial genomic materials with a plurality of DNA Invading Artificial Nucleic Acids (DIANAs); and (6) Detecting binding of one or more DIANAs the microbial genomic material of its respective single species or group of microbes, wherein the detection of binding indicates the presence of one or more specific microbial species or groups of microbes in the original sample.

Example 1: Selective Removal of Select Eukaryote DNA from Whole-Blood

This example shows that hDNA was selectively removed from whole-blood using the methods and devices described herein.

An schematic of the device used for the selective removal of select eukaryote DNA from whole-blood is shown in FIGS. 6A-6B.

Methods 1.5 ml samples of unprocessed human-whole blood were added to an initial reservoir in the device. In order to initiate the reaction, the 1.5 ml blood sample was flowed via pneumatics to a reaction reservoir which contained 1.75 ml of a selective lysis solution containing about 0.5% (v/v) Tween 20 and Triton X-100. The combined blood—selective lysis solution mixture was incubated and agitated for about 1 minute at ambient temperature (about 21° C.). Agitation occurred with the addition of sterile air into the reservoir. The reaction was terminated with the addition of a lysis terminating solution containing 4M NaCl, with a pH equal to about 7.0, likewise at room temperature.

After terminating the lysis process, the combined blood—selective lysis solution mixture was flowed to new reservoir containing about 1 mg diethylethanolamine coupled magnetic beads (e.g., support substrates), diameter of about 500 nm-1 μm, i.e., The magnetic beads and solution were incubated with gentle agitation for 5 minutes at room temperature.

After the incubation and agitation period, a rare-earth magnet was introduced outside the reservoir to immobilize the beads to the wall of the reservoir. The supernatant was removed from the reservoir and flowed via pneumatics to a new reservoir.

The end result of this process is that the magnetic beads, now immobilized, contained select eukaryote DNA extracted from the blood sample, whereas the final mixture, or supernatant was largely depleted of select eukaryote DNA The hDNA output was quantified through absorption based assays.

All processing steps described above were conducted 5 times where the results indicated in Table 5 are displayed as Mean±S. dev.

TABLE 5

| | Study I | Study II | Study III | Study IV | Study V | Summary |
|---|---|---|---|---|---|---|
| hDNA Removal Efficiency: | 99.90% | 99.92% | 99.92% | 99.91% | 99.89% | 99.91 ± 0.01% |

Example 2: γPNA Detection of Fungal 18S

This example shows that fungal 18S amplicons, previously amplified with a broad-range PCR process, can be identified on an automated device specific for gamma-modified PNA-based detection. Further, this example highlights that target DNA can be generally discriminated down to the species level owing to low background and off-target binding.

Methods

*C. albicans*, full-length, 18S which was previously amplified with hapten-modified primers was used as the test molecule. Upon initialization of the study, 0.5 fmole of *C. albicans*, full-length, 18S, was divided equally into 5 reservoirs of the device's reservoirs, each loaded with a single biotinylated gamma-modified PNA probe type specific to *C. albicans, C. glabrata, C. krusei, C. tropicalis*, and *C. parapsilosis* with sequences identified in Table 1. An invasion buffer, containing Tween-20, NaCl, and poly-EG-12,000, was brought into each of the 5 reservoirs filling each reservoir to a volume of roughly 2000. Each of the reservoirs where heated, in parallel, to 75° C. for 5 minutes, after which into each reservoir 50 μl of MyOne C1 Streptavidin coated beads where brought in from a MyOne C1 Streptavidin storage reservoir. The combined DNA—γPNA—bead mixture was agitated for roughly 3 minutes through the flow of sterile air into each reservoir.

Post-immobilization of γPNA onto the beads, the beads were immobilized, the buffer removed, and then resuspended and washed in a solution containing between 150-550 mM NaCl at a temperature at least 75-95° C. Post washing, to each reservoir a solution containing a HRP-conjugate targeting the primer-hapten was added, which binds to the free hapten (if present) on the captured amplicon. After a number of wash steps with a neutral low salt wash, luminol was added to create a distinct optical signature only where the microbial DNA was captured. The optical signatures were read using a Promega GloMax plate reader with an integration time of 2.5 sec/well.

A similar study was completed "on bench" for comparison purposes.

Figure 7:
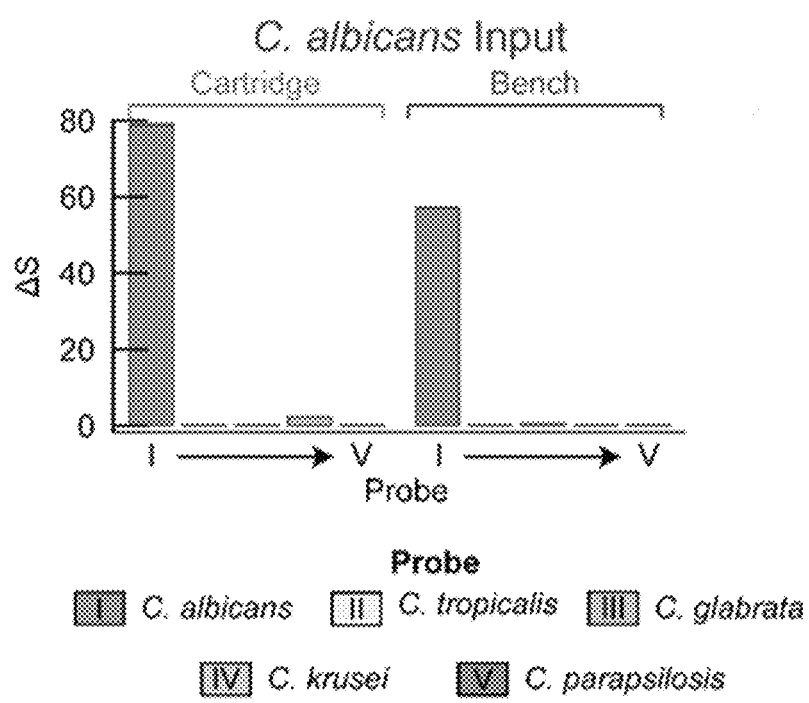
FIG. 7 are plots of an optical detection of 0.5 fmoles of *Candida albicans* using the fluidic device described herein, compared to on-bench, manual, processing, according to one set of embodiments.

Results: A clearly identifiable optical signature was only seen in the *C. albicans* channel (which came from the chamber activated with a gamma-modified PNA probe specific to *C. albicans*). See FIG. 7.

These results show that the compositions, methods, and devices disclosed herein can identify at least one specific pathogen amplicon. Accordingly, the compositions and methods disclosed herein are useful for the detection and identification of microbes.

Example 3: γPNA Detection of a Panel of Microbial 16S/18S

This example shows that microbial 16S/18S amplicons, previously amplified with a broad-range PCR process, can be identified on an automated device specific for gamma-modified PNA-based detection. Further, this example highlights that target DNA can be discriminated down to the species level owing to low background and off-target binding.

Methods

Full-length, 16S/18S from either *E. cloacae, E. faecium*, or *C. glabrata* which was previously amplified with hapten-modified primers was used as the test molecule. Upon initialization of the study, 0.5 fmole of the amplified, full-length, 16S/18S, was divided equally into 17 reservoirs of the device's fluidic reservoirs, each loaded with a single biotinylated gamma-modified PNA probe type specific to the list of pathogens highlighted in Table 1 with sequences as likewise identified in Table 1. An invasion buffer, containing Tween-20, NaCl, and poly-EG-12,000, was brought into each of the 17 reservoirs filling each reservoir to a volume of roughly 200 µl. Each of the reservoirs where heated, in parallel, to 75° C. for 5 minutes, after which into each reservoir 50 µl of MyOne C1 Streptavidin coated beads where brought in from a MyOne C1 Streptavidin storage reservoir. The combined DNA—γPNA—bead mixture was agitated for roughly 3 minutes through the flow of sterile air into each reservoir.

Post-immobilization of γPNA onto the beads, the beads were immobilized, the buffer removed, and then resuspended and washed in a solution containing between 150-550 mM NaCl at a temperature at least 75-95° C. Post washing, to each reservoir a solution containing a HRP-conjugate targeting the primer-hapten was added, which binds to the free hapten (if present) on the captured amplicon. After a number of wash steps with a neutral low salt wash, luminol was added to create a distinct optical signature only where the microbial DNA was captured. The optical signatures were read using a Promega GloMax plate reader with an integration time of 2.5 sec/well.

Figure 8:
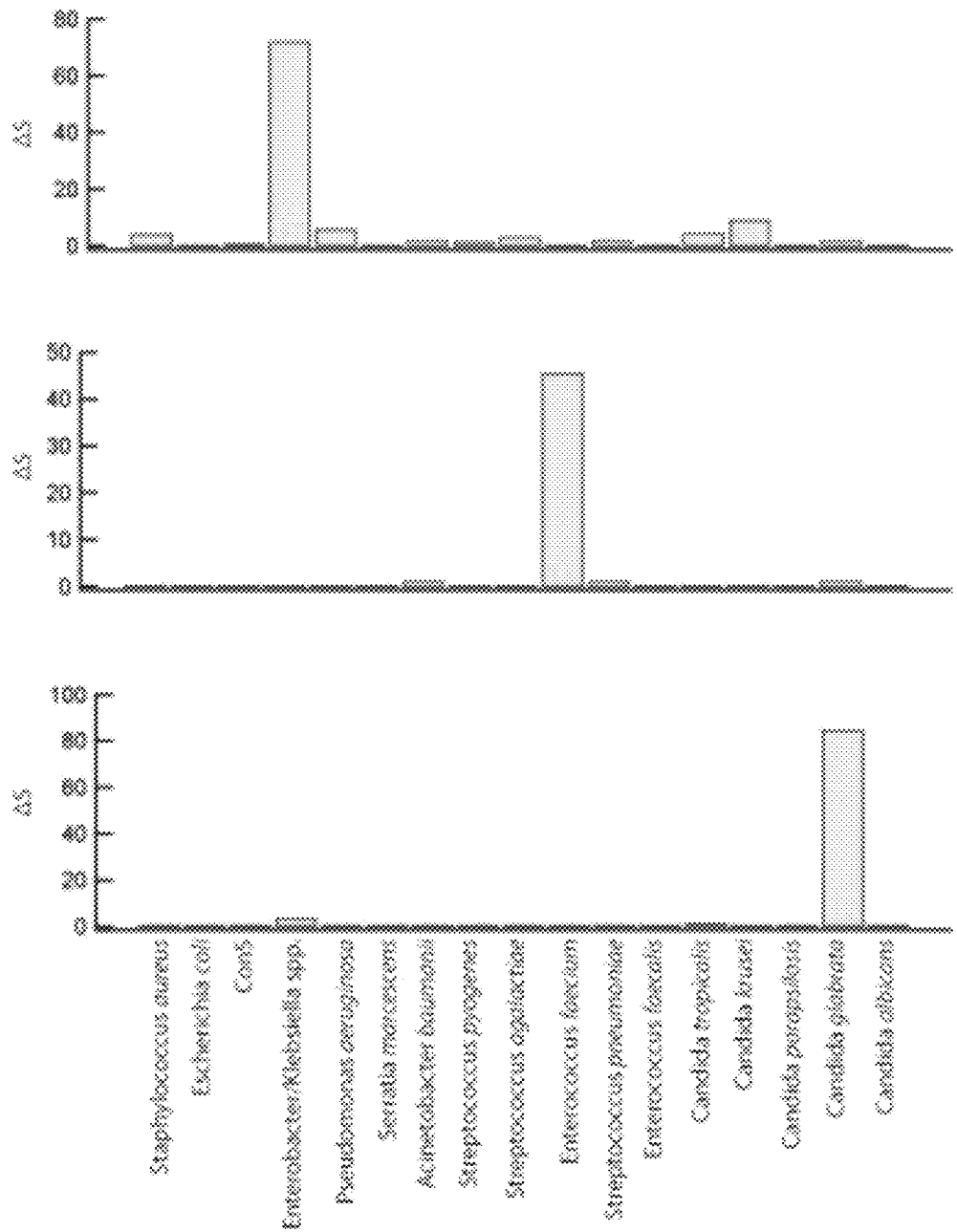
FIG. 8 is a plot of an optical detection of 0.5 fmoles of *E. cloacae* (top), *E. faecium* (middle), or *C. glabrata* (bottom), using the fluidic device described herein, according to one set of embodiments.

Results: A clearly identifiable optical signature was only seen in the *E. cloacae* (top), *E. faecium* (middle), and *C. glabrata* (bottom) channels (which came from the reservoir activated with a gamma-modified PNA probe specific to *E. cloacae*, *E. faecium*, and *C. glabrata*, respectively). See FIG. 8.

These results show that the compositions, methods, and devices disclosed herein can identify at least one specific pathogen amplicon. Accordingly, the compositions and methods disclosed herein are useful for the detection and identification of microbes.

Example 4: Device Based PCR Amplification of Genomic Material

This example shows that microbial genomic material can be amplified with high sensitivity on an automated device which was developed to encompass the first four steps of the previous described multi-step process: 1) Deplete, selectively, select eukaryote DNA from the sample; (2) Lyse one or more of the microbial cells in the inputted sample, wherein the lysing of one or more microbial cells releases a plurality of microbial genomic materials; (3) Isolate the plurality of microbial genomic materials (namely DNA and/or RNA); and (4) Amplify the plurality of microbial genomic materials Methods Previously extracted genomic material derived from *C. albicans* was used as the DNA template in these studies. 50 µl PCR reactions were setup as defined in the manufacturer's protocol (Q5, New England BioLabs) using the following genomic inputs: 130 copies, 26 copies, 5 copies, 1 copy, and no template added (negative control). Primer pairs with the following sequences: CCC CCC CCT CAG TTA TCG TTT ATT TGA TAG TAC C (SEQ ID NO: 38); CCC CCC CCT CAG TTA TCG TTT ATT TGA TAG TTC C (SEQ ID NO: 39); CCC TTC CCA GAG TTT GAT CAT GGC TCA G (SEQ ID NO: 40); CCC TTC CAG AGT TTG ATC CTG GCT CAG (SEQ ID NO: 41); CCC CCC GGT TAC CTT GTT ACG ACT T (SEQ ID NO: 42); CCC CCGG CTA CCT TGT TAC GACT T (SEQ ID NO: 43); CCC TTC CCT GAT GAC TCG TGC CTA CTA (SEQ ID NO: 44); CCC TCT CCC TGA TGA CTT GCG CTT ACT A (SEQ ID NO: 45); were used to amplify the genomic material.

Amplification cycling employed the following protocol: 98° C. for 30 sec; followed by 4 cycles of 98° C. for 10 sec, 62° C. for 30 sec, and 72° C. for 45 sec; followed by 26 cycles of 98° C. for 10 sec, and 72° C. for 45 sec; followed by 72° C. for 2 min.

All process where completed identically both on-device and on-bench in a standard 0.2 ml PCR tube. Following processing, roughly 13% of the sample was loaded and run on a 1% gel, and imaged using SYBR safe intercalating dye on a home-built imaging system.

Figure 9:
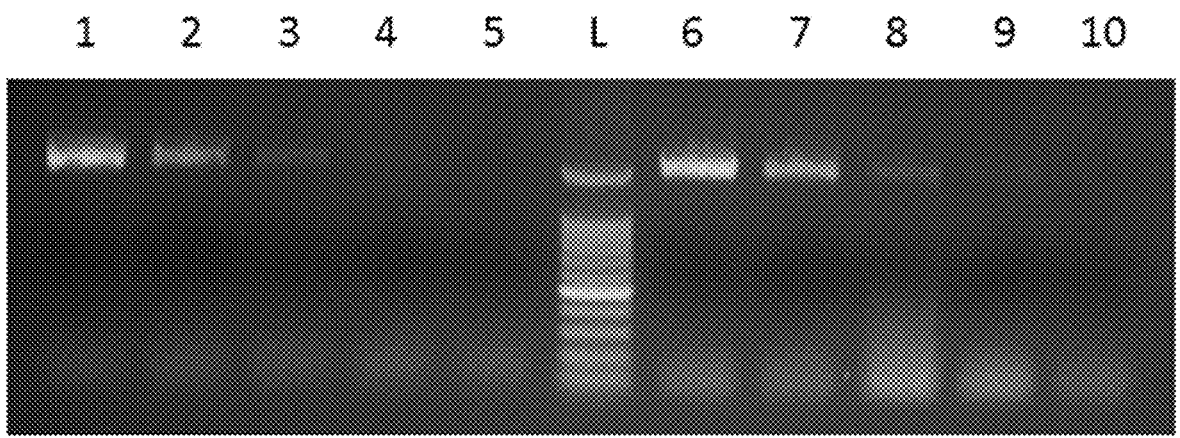
FIG. 9 is a photograph of a gel highlighting the yields of enzymatically amplifying different initial concentrations of microbial genomic material either on-bench (lanes 1-5) or on-device (lanes 6-10), according to one set of embodiments.

Results: A clearly identifiable optical signature was detected down to a single copy where negative control reactions did not yield a quantifiable result. See FIG. 9.

These results show that the compositions, methods, and devices disclosed herein can enzymatically amplify microbial genomic material with high sensitivity with results equivalent to those completed on-bench.

Example 5: Device-Based Extraction of Microbial Genomic Material from Whole-Blood Samples This example show that microbial genomic material can be extracted and isolated from unprocessed whole-human-blood high sensitivity on an automated device which was developed to encompass the first four steps of the previous described multi-step process: 1) Deplete, selectively, select eukaryote DNA from the sample; (2) Lyse one or more of the microbial cells in the inputted sample, wherein the lysing of one or more microbial cells releases a plurality of microbial genomic materials; (3) Isolate the plurality of microbial genomic materials (namely DNA and/or RNA); and (4) Amplify the plurality of microbial genomic materials Methods Fresh human whole-blood drawn into a EDTA vacuette was inoculated with *C. albicans* (ATCC #90028) at 50 CFU/ml and at 16 CFU/ml. 1.5 ml of contrived human blood was extracted and placed into a fresh vial. 1.5 ml of the sample was loaded into the device and pneumatically flowed into a reaction reservoir containing WAX magnetic beads. To the 1.5 ml blood sample, 1.5 ml of a selective or mild lysis solution comprising of Tween-20 (v/v) and Triton-X100 at (v/v) was pneumatically added, flowed from its storage reservoir. After about 5 minutes, NaCl was added to the combined mixture to a final concentration of 150-300 mM and WAX conjugated magnetic particles were added. After about 2 minutes, a rare earth magnet was used to immobilize the magnetic particles to the surface of the vial and about 3 ml of solution was removed and pneumatically flowed into a new reservoir containing cross-linked and affinity purified lysozyme (2-13 mg), mutanolysin (10-350 U), zymolyase (18-200 U), and lysostaphin (65-250 U) in addition to a detergent based reagent containing a glucopyrano side, a cationic detergent, and a sulfobetaine (all of which were at concentrations above their individual CMCs (>10×)). The microbial lysis reaction also included EDTA (at about 10 mM) and 2-Mercaptoethanol (at about 25 mM).

The combined reaction mixture was agitated for about 10 to 15 minutes after which the mixture was pneumatically flowed to a new reservoir containing WAX-modified magnetic beads. In this reservoir, the combined solution-bead mixture was agitated for about 1-5 minutes after which a rare earth magnet was used to immobilize the magnetic particles to the surface of the vial and the solution was pneumatically flowed out of the reservoir.

The beads where then washed repeatedly by flowing a wash solution containing 1 M NaCl which resuspended the beads, agitating them, immobilizing the beads and removing the wash solution. After 2-3 washed, the microbial DNA was eluted off of the beads with an elution reagent buffered to pH 12.5 which was pneumatically flowed to the reservoir from its dedicated storage reservoir. The solution was then removed from the device and processed on-bench.

The microbial DNA was subject to PCR of the full length rDNA with the following primer sequences (5'-3'):

```
                                      (SEQ ID NO: 38)
CCC CCC CCT CAG TTA TCG TTT ATT TGA TAG TAC C;

(SEQ ID NO: 39)
CCC CCC CCT CAG TTA TCG TTT ATT TGA TAG TTC C;

(SEQ ID NO: 40)
CCC TTC CCA GAG TTT GAT CAT GGC TCA G;

(SEQ ID NO: 41)
CCC TTC CAG AGT TTG ATC CTG GCT CAG;

(SEQ ID NO: 42)
CCC CCC GGT TAC CTT GTT ACG ACT T;

(SEQ ID NO: 43)
CCC CCGG CTA CCT TGT TAC GACT T;

(SEQ ID NO: 44)
CCC TTC CCT GAT GAC TCG TGC CTA CTA;

(SEQ ID NO: 45)
CCC TCT CCC TGA TGA CTT GCG CTT ACT A
```

Each primer contains a hapten moiety for subsequent labelling. Post-PCR, the sample was divided equally into 5 reservoirs, each loaded with biotinylated gamma-modified PNA probes with sequences identified in Table 1 for *C. albicans, C. glabrata, C. krusei, C. tropicalis*, and Universal Fungal, with an invasion supporting reagent containing Tween-20, NaCl, and poly-EG-12,000. Each well was heated to 70-95° C. for 1-5 minutes with the addition of 5 ml of stock MyOne C1 Streptavidin coated beads. Post-immobilization of □PNA probes onto the beads, the beads were washed in a solution containing between 150-550 mM NaCl at a temperature at least 75-95° C. Post washing, to each reservoir a solution containing a HRP-conjugate targeting the primer-hapten was added, which binds to the free hapten (if present) on the captured amplicon. After a number of wash steps with a neutral low salt wash, luminol was added to create a distinct optical signature only where the microbial DNA was captured. The optical signatures were read using a Promega GloMax plate reader with an integration time of 2.5 sec/well.

Figure 10A:
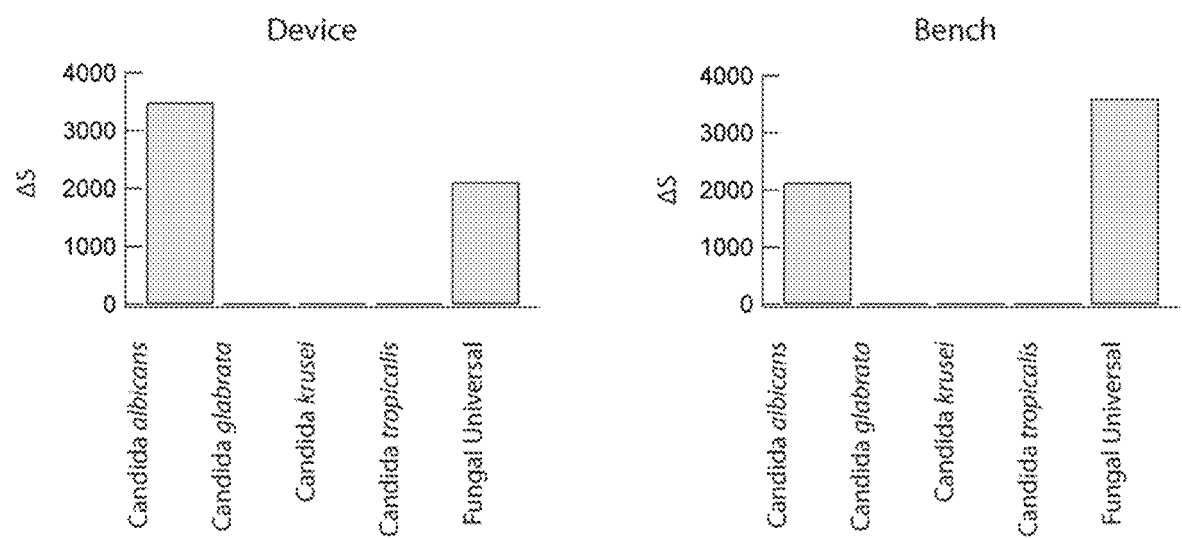
FIG. 10A are plots comparing the on-bench or manual removal of select eukaryote DNA from unprocessed human whole-blood, the lysing of *C. albicans*, and the isolation of the *C. albicans* extracted genomic material to the fluidic device described herein at 50 CFU/ml, according to one set of embodiments.
Figure 10B:
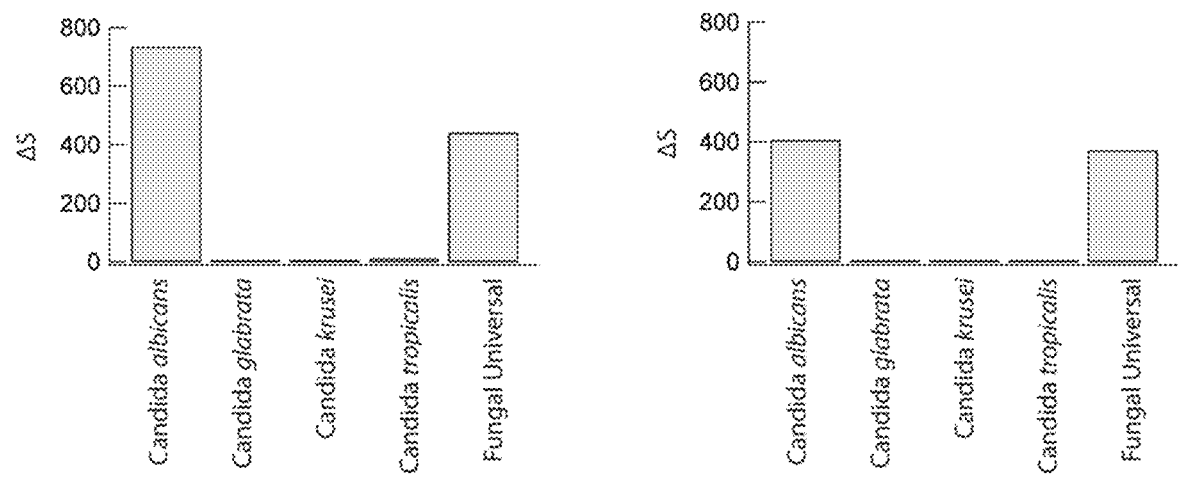
FIG. 10B are plots comparing the on-bench or manual removal of select eukaryote DNA from unprocessed human whole-blood, the lysing of *C. albicans*, and the isolation of the *C. albicans* extracted genomic material to the fluidic device described herein at 16 CFU/ml, according to one set of embodiments.

Results: A clearly identifiable optical signature was only seen in the *C. albicans* and Fungal Universal channel (which came from the reservoir activated with a gamma-modified PNA probe specific to *C. albicans* and Fungal Universal). Comparison studies completed entirely on-bench yielded similar results. See FIG. 10A for the 50 CFU/ml study and FIG. 10B for the 16 CFU/ml study.

Example 6: Mixing/Resuspension

The following example demonstrates an exemplary set of operations using a fluidic device for mixing/resuspension a fluid (e.g., using the portion of the device shown in FIG. 12A).

In one experiment, a reaction took place within a fluidic device as described herein, where DNA was bound to a mass of magnetic beads/particles (e.g., support substrates; mean diameter 1±0.15 μm) resuspended in a 100 μl volume of a Gu-HCl based aqueous solution. One or more wash steps (e.g., to remove non-specific binding to the magnetic beads) may be performed by flowing a reaction mixture at a pressure of 1 psi through a first inlet channel (e.g., channel 1240 in FIG. 12A) associated with a valve (e.g., valve 1245 in FIG. 12A) from an upstream reaction chamber in fluidic communication with the channel (e.g., not shown in FIG. 12A; upstream of fluidic reservoir 1210), to a first fluidic reservoir (e.g., fluidic reservoir 1210 in FIG. 12A) having a volume of approximately 100 μl (e.g., dimensions of 25 mm long×3 mm deep×1.33 mm wide) which is constructed with a semi-permeable membrane as the cover of the reservoir. During the flow process, a valve downstream of the first fluidic reservoir (e.g., valve 1235 in FIG. 12A) and connected to a connecting channel (e.g., connecting channel 1230 in FIG. 12A e.g., having dimensions 3 mm deep, 4 cm long, and 0.15 mm wide) was closed. This caused filling of the first reservoir to completion as the air is removed from this reservoir by passing through the semi-permeable membrane.

A magnet was brought into proximity (for example, as described below) to the first fluidic reservoir to surface immobilize the volume of magnetic beads to the bottom of the first fluidic reservoir. The valve associated with the connecting channel (e.g., valve 1235) was then opened. A gas, e.g., air, at 1 psi, was introduced into the first fluidic reservoir to push the reaction mixture out of the first fluidic reservoir via the connecting channel. After removing the reaction mixture out of the first fluidic reservoir, the valve associated with the connecting channel was closed. The magnet was then moved away from proximity to the first fluidic reservoir (an optional step). A wash solution (for example, 1M NaCl, 10 mM Tris-HCl, pH 7.2) was introduced into the first fluidic reservoir. To resuspend and wash the magnetic beads, after introducing the wash solution, the valve associated with the connecting channel (e.g., valve 1235) was opened, and the wash solution and the magnetic beads were transferred to a second fluidic reservoir (e.g., fluidic reservoir 1220 in FIG. 12A) via the connecting channel (e.g., connecting channel 1230). The second fluidic reservoir was of equal volume and dimensions to that of the first fluidic reservoir (although other configurations are possible) and was likewise constructed with a semi-permeable membrane on/as the roof of the reservoir. The second fluidic reservoir was fluidically connected to a second channel (e.g., channel 1250 in FIG. 12A) and a second valve associated with the second channel (e.g., valve 1255 in FIG. 12A). This second valve was closed during the transfer step.

A wash buffer was introduced into the second fluidic reservoir by way of the connecting channel and first fluidic reservoir. The valves associated with the connecting channel (e.g., valve 1235) and the second channel (e.g., valve 1255) were opened during this step. A gas, e.g., air, at 1 psi, was introduced, pushing, via the second channel, the reaction mixture out of the second fluidic reservoir via the connecting channel back into the first fluidic reservoir. During this step, the valve associated with the first channel (e.g., valve 1245) was closed. By repeating this process of transferring or 'shuttling' the wash solution between the first fluidic reservoir and the second fluidic reservoir, the magnetic beads may be resuspended and/or washed. After completing the washing of the magnetic beads, the beads can be surface immobilized to the first fluidic reservoir and any high salt wash solution can be removed, thus readying the DNA-bound beads for downstream reactions/detection.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "select eukaryote" should be understood to mean either originating from plant/fungal or mammalian sources. In some embodiments, animal (e.g., mammalian) eukaryotic cells are used. In certain embodiments, plant eukaryotic cells are used. In some cases, fungal eukaryotic cells are used. In some embodiments, all eukaryotic cells of a sample are processed (e.g., lysed). In some embodiments, mammalian eukaryotic cells are process and other eukaryotic cells in the sample (e.g., fungi cells) are not processed or lysed.

As used herein in the specification and in the claims, the phrase "genomic" should be understood to mean either DNA and/or RNA.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

A "subject" or a "patient" refers to any mammal (e.g., a human), for example, a mammal that may be susceptible to a disease or bodily condition. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A patient may be a subject diagnosed with a certain disease or bodily condition or otherwise known to have a disease or bodily condition. In some embodiments, a patient may be diagnosed as, or known to be, at risk of developing a disease or bodily condition. In other embodiments, a patient may be suspected of having or developing a disease or bodily condition, e.g., based on various clinical factors and/or other data.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed:

1. A fluidic device, comprising:
a sample inlet;
a fluidic channel in fluidic communication with the sample inlet, wherein the fluidic channel has a length of at least 1 cm and a length-to-width ratio of at least 5:1;
a first lysis region in fluidic communication with the fluidic channel, wherein the first lysis region contains one or more non-ionic detergents that selectively lyses eukaryote cells;
a first isolation region in fluidic communication with first lysis region;
a second lysis region in fluidic communication with the first isolation region, wherein the second lysis region contains one or more reagents that lyses microbial cells;
a second isolation region in fluidic communication with the second lysis region;
at least one reaction region in fluidic communication with the second isolation region;
an amplification region in fluidic communication with at least one of the reaction regions; and
a processing chamber in fluidic communication with the amplification region, wherein the processing chamber contains a duplex DNA Invading Artificial Nucleic Acid (DIANA) for detecting a microbial genomic material from one or more microbial cells.

2. A fluidic device as in claim 1, comprising a fluidic reservoir having an inlet and an outlet, wherein the fluidic reservoir has a volume of at least 0.1 mL.

3. A fluidic device as in claim 2, comprising a gas chamber, wherein the gas chamber is in fluidic communication with the fluidic reservoir.

4. A fluidic device as in claim 2, wherein a longitudinal axis of the fluidic reservoir is substantially perpendicular to, and lies on a different plane than, a longitudinal axis of the fluidic channel, wherein the fluidic reservoir has a height of at least 1 cm and a volume of at least 1 mL, and wherein the fluidic reservoir allows the passage of a gas into the fluidic reservoir to facilitate mixing of a fluid in the fluidic reservoir, the gas exiting the fluidic reservoir via the outlet.

5. A fluidic device as in claim 1, wherein each fluidic channel is in fluidic communication with one or more fluidic reservoirs.

6. A fluidic device as in claim 1, wherein each fluidic channel has a volume of less than 2000 μL.

7. A fluidic device as in claim 1, comprising a first fluidic reservoir having a volume of less than or equal to 500 microliters.

8. A fluidic device as in claim 7, comprising a second fluidic reservoir having a volume of less than or equal to 500 microliters.

9. A fluidic device as in claim 8, wherein the first fluidic reservoir and/or the second fluidic reservoir has a cross-sectional dimension of less than or equal to 2 mm.

10. A fluidic device as in claim 1, wherein the fluidic channel has an average cross-sectional dimension of less than or equal to 1 mm.

11. A fluidic device as in claim 1, wherein the first isolation region contains an anion exchange resin conjugated to a solid-support substrate.

12. A fluidic device as in claim 1, wherein the second isolation region contains an anion exchange resin conjugated to a solid-support substrate.

13. A fluidic device as in claim 1, wherein each processing chamber is in fluid communication with one or more metering channels.

14. A fluidic device as in claim 1, wherein the fluidic device contains a plurality of duplex DIANAs, wherein each DIANA targets one or more amplicons originating from a specific microorganism or group of microorganisms.

15. A fluidic device as in claim 1, wherein the DIANA comprises a peptide nucleic acid, a locked nucleic acid, or a bridged nucleic acid.

16. A fluidic device as in claim 1, wherein the DIANA comprises a peptide nucleic acid oligomer having a chiral stereo-center at the gamma position of the backbone.

17. A fluidic device as in claim 1, wherein the fluidic device contains an invasion buffer comprising one or more crowding agents, one or more DNA denaturants, one or more monovalent salts, and/or one or more surfactants.

18. A fluidic device as in claim 1, wherein the fluidic device contains an invasion buffer comprising a crowding agent, and wherein the crowding agent comprises a polyethylene-glycol, dextran, polyvinyl alcohol, Ficoll, glycerol, glucose, and/or sucrose.

19. A fluidic device as in claim 1, wherein the fluidic device contains an invasion buffer comprising a DNA denaturant agent, and wherein the denaturing agent comprises DMSO, formamide, and/or a betaine.

20. A fluidic device as in claim 1, wherein the first isolation region contains an anion exchange resin conjugated to a solid-support substrate.

21. A fluidic device as in claim 20, wherein the anion exchange resin comprises tertiary and/or quaternary amine functional groups.

22. A fluidic device as in claim 1, wherein the fluidic device contains a wash solution having a pH between 6 and 9.

23. A fluidic device as in claim 1, wherein the fluidic device comprises:
a fluidic hub comprising a hub channel having a length of at least 1 cm and a channel length-to-width ratio of at least 5:1;
at least 10 branching channels branching from the fluidic hub; and
a plurality of valves positioned between the branching channels and the fluidic hub.

24. A fluidic device, comprising:
a sample inlet;
a fluidic channel in fluidic communication with the sample inlet, wherein the fluidic channel has a length of at least 1 cm and a length-to-width ratio of at least 5:1;
a first lysis region in fluidic communication with the fluidic channel, wherein the first lysis region contains one or more detergents that selectively lyses eukaryote cells;
a first isolation region in fluidic communication with first lysis region;
a second lysis region in fluidic communication with the first isolation region, wherein the second lysis region contains one or more reagents that lyses microbial cells;
a second isolation region in fluidic communication with the second lysis region;
a reaction region in fluidic communication with the second isolation region, wherein the reaction region comprises a mixing system, the mixing system, comprising:
   a channel;
   a first valve, wherein the first valve is associated with the channel and can reversibly open and close;
   a fluidic reservoir connected to the channel;
   an outlet channel in fluidic communication with the fluidic reservoir;
   a second valve, where in the second valve is associated with the outlet channel, and wherein the second valve can reversibly open and close; and
   a cover adjacent to the fluidic reservoir, wherein the cover encloses the fluidic reservoir, wherein the cover is a semipermeable membrane, and wherein the semipermeable membrane is hydrophobic, has an air permeability of greater than or equal to 0.4 slpm at 1 psi and less than or equal to 5 slpm at 1 psi,
an amplification region in fluidic communication with the reaction region; and
a processing chamber in fluidic communication with at least one of the reaction regions and/or the amplification region.

25. A fluidic device as in claim 24, wherein the semipermeable membrane has a mean pore size of greater than or equal to 0.02 microns and less than or equal to 0.5 microns.

26. A fluidic device as in claim 24, wherein the semipermeable membrane has a water intrusion pressure of greater than or equal to 2 psi and less than or equal to 120 psi.

27. A fluidic device as in claim 24, wherein the semipermeable membrane is superhydrophobic.

28. A fluidic device as in claim 24, wherein the semipermeable membrane comprises a fluorinated material.

29. A fluidic device as in claim 24, wherein the semipermeable membrane comprises polyvinylidene fluoride.

30. A fluidic device as in claim 24, wherein the semipermeable membrane is configured and arranged to have a liquid loss pressure of less than or equal to 50 psi.

31. A fluidic device as in claim 24, wherein the fluidic reservoir has a volume of less than or equal to 500 microliters.

32. A fluidic device as in claim 24, wherein the cover is configured and arranged to receive a sealing gasket that can be brought into contact with the cover and maintain closure of the cover upon application of a pressure to a fluid entering the fluidic reservoir.

33. A fluidic device as in claim 24, wherein the cover encloses both the fluidic reservoir and the channel connected to the fluidic reservoir.

34. A fluidic device as in claim 24, wherein the fluidic device contains a plurality of duplex DIANAs, wherein each DIANA targets one or more amplicons originating from a specific microorganism or group of microorganisms.

35. A fluidic claim as in claim 24, wherein the mixing system facilitates mixing of a fluid by allowing the fluid to be flowed in a first direction from the first valve to the second valve, and in a second direction different than the first direction from the second valve to the first valve.

* * * * *